US012618074B2

(12) United States Patent
Al-Ogaili et al.

(10) Patent No.: US 12,618,074 B2
(45) Date of Patent: May 5, 2026

(54) CD40 SPECIFIC DNA APTAMERS AS VACCINE ADJUVANTS

(71) Applicants: THE BOARD OF TRUSTEES OF THE UNIVERSITY OF ARKANSAS, Little Rock, AR (US); THE TEXAS A&M UNIVERSITY SYSTEM, College Station, TX (US)

(72) Inventors: Adil Sabr Al-Ogaili, Wasit (IQ); Tieshan Jiang, Fayetteville, AR (US); Christine N. Vuong, Fayetteville, AR (US); Rohana Liyanage, Fayetteville, AR (US); Jackson O. Lay, Jr., West Fork, AR (US); Suresh Kumar Thallapuranam, Fayetteville, AR (US); Luc R. Berghman, College Station, TX (US); Young Min Kwon, Lincoln, AR (US); Billy Hargis, Fayetteville, AR (US)

(73) Assignees: THE BOARD OF TRUSTEES OF THE UNIVERSITY OF ARKANSAS, Little Rock, AR (US); THE TEXAS A&M UNIVERSITY SYSTEM, College Station, TX (US)

( * ) Notice: Subject to any disclaimer, the term of this patent is extended or adjusted under 35 U.S.C. 154(b) by 1233 days.

(21) Appl. No.: 17/602,951

(22) PCT Filed: Apr. 13, 2020

(86) PCT No.: PCT/US2020/027970
§ 371 (c)(1),
(2) Date: Oct. 11, 2021

(87) PCT Pub. No.: WO2020/210817
PCT Pub. Date: Oct. 15, 2020

(65) Prior Publication Data
US 2022/0186224 A1     Jun. 16, 2022

Related U.S. Application Data

(60) Provisional application No. 62/952,802, filed on Dec. 23, 2019, provisional application No. 62/832,725, filed on Apr. 11, 2019.

(51) Int. Cl.
| | |
|---|---|
| *C12N 15/115* | (2010.01) |
| *A61K 39/39* | (2006.01) |
| *A61K 39/00* | (2006.01) |

(52) U.S. Cl.
CPC ............ C12N 15/115 (2013.01); A61K 39/39 (2013.01); A61K 2039/55561 (2013.01); C12N

2310/16 (2013.01); *C12N 2310/17* (2013.01); *C12N 2310/3513* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 6,087,329 | A | 7/2000 | Armitage et al. |
| 6,410,711 | B1 | 6/2002 | Armitage et al. |
| 6,923,958 | B2 | 8/2005 | Xiang et al. |
| 7,238,499 | B2 | 7/2007 | Reddy |
| 7,332,298 | B2 | 2/2008 | Kornbluth |
| 7,371,392 | B2 | 5/2008 | Tripp et al. |
| 7,405,270 | B2 | 7/2008 | Armitage et al. |
| 8,604,178 | B2 | 12/2013 | Bottje et al. |
| 8,956,618 | B2 | 2/2015 | Berghman et al. |
| 8,956,849 | B2 | 2/2015 | Bottje et al. |
| 8,961,990 | B2 | 2/2015 | Hargis et al. |
| 9,125,854 | B2 | 9/2015 | Bottje et al. |
| 9,226,957 | B2 | 1/2016 | Bottje et al. |
| 9,603,915 | B2 | 3/2017 | Barta et al. |
| 9,884,099 | B2 | 2/2018 | Barta et al. |
| 10,016,493 | B2 | 7/2018 | Bottje et al. |
| 10,376,571 | B2 | 8/2019 | Bielke et al. |
| 10,682,398 | B2 | 6/2020 | Faulkner |
| 2003/0099644 | A1 | 5/2003 | Ahuja et al. |
| 2006/0078994 | A1 | 4/2006 | Healey et al. |
| 2006/0246123 | A1 | 11/2006 | Gilboa et al. |
| 2007/0128223 | A1 | 6/2007 | Tang et al. |
| 2007/0237779 | A1 | 10/2007 | Ledbetter et al. |
| 2009/0004194 | A1 | 1/2009 | Kedl |
| 2010/0291109 | A1 | 11/2010 | Kedl |
| 2012/0083521 | A1 | 4/2012 | Sullenger et al. |
| 2013/0040837 | A1 | 2/2013 | Karp et al. |

(Continued)

FOREIGN PATENT DOCUMENTS

| | | |
|---|---|---|
| WO | 1993008207 | 4/1993 |
| WO | 1995014487 | 6/1995 |

(Continued)

OTHER PUBLICATIONS

Zhou et al., Anal. Chem., 2007, 79:7492-7500 (Year: 2007).*

(Continued)

*Primary Examiner* — Stacy B Chen
(74) *Attorney, Agent, or Firm* — Quarles & Brady, LLP

(57) ABSTRACT

The present invention provides immunostimulatory nucleic acids that have an affinity to a specific target protein. The present invention also provides templates and methods for making and using the immunostimulatory nucleic acids. Further, methods for linking the immunostimulatory nucleic acids to antigens and using the resulting complexes to enhance an immune response are provided.

18 Claims, 20 Drawing Sheets

Specification includes a Sequence Listing.

(56) References Cited

U.S. PATENT DOCUMENTS

| | | | |
|---|---|---|---|
| 2016/0299131 A1 | 10/2016 | Hirao et al. | |
| 2016/0319361 A1 | 11/2016 | Spetzler et al. | |
| 2017/0096640 A1 | 4/2017 | Healey et al. | |
| 2017/0196971 A1 | 7/2017 | Berghman et al. | |

FOREIGN PATENT DOCUMENTS

| | | |
|---|---|---|
| WO | 1996026735 | 9/1996 |
| WO | 2001056602 | 8/2001 |
| WO | 2004009615 | 1/2004 |
| WO | 2005058950 | 6/2005 |
| WO | 2007056266 | 5/2007 |
| WO | 2012041635 | 4/2012 |
| WO | 2018213791 | 11/2018 |

OTHER PUBLICATIONS

Abi-Ghanem et al., Phage display selection and characterization of a single-chain antibody against chicken CD40. Poultry Science. 89 (E-Suppl. 1):61. (2010).

Alvarez et al., Mechanisms and consequences of dendritic cell migration. Immunity. 29(3):325-342. (2008).

An et al., Crystallographic and mutational analysis of the CD40-CD154 complex and its implication for receptor activation. J. Biol. Chem. 286(13):11226-11235. (2011).

Armitage et al., B-cell stimulation. Curr. Opin. Immunol. 7:243-247. (1995).

Armitage et al., Molecular and biological characterization of a murine ligand for CD40. Nature. 357(6373):80-82. (1992).

Armstrong et al., Rationally manipulating aptamer binding affinities in stem-loop molecular beacon. Bioconj. Chem. 25(10): 1769-1776. (2014).

Baccam et al., Membrane-bound CD154, but not CD40-specific antibody, mediates NF-κB-independent IL-6 production in B cell. Eur. J. Immunol. 29(12):3855-3866. (1999).

Bajorath et al., Construction and analysis of a detailed three-dimensional model of the ligand binding domain of the human B cell receptor CD40. Proteins: Structure, Function and Genetics. 27(1):59-70. (1997).

Baker, Reproducibility crisis: Blame it on the antibodies. Nature. 521(7552):274-276. (2015).

Banchereau et al., The CD40 antigen and its ligand. Annu. Rev. Immunol. 12(1):881-922. (1994).

Barr et al., Enhanced in vitro immune responses to bacterial lipopolysaccharide by exogenous CD40 stimulation. Infection and Immunity. 67(7):3637-3640. (1999).

Barr et al., Functional activity of CD40 antibodies correlates to the position of binding relative to CD154. Immunology. 102(1):39-43. (2001).

Beatty et al., Cancer immunotherapy: activating innate and adaptive immunity through CD40 agonists. Expert Rev. Anticanc. Ther. 17(2): 175-186. (2017).

Bennett et al., Help for cytotoxic-T-cell responses is mediated by CD40 signalling. Nature. 393(6684):478-480. (1998).

Berens et al., A tetracycline-binding RNA aptamer. Bioorg. Med. Chem. 9(10):2549-2556. (2001).

Björck et al., Antibodies to distinct epitopes on the CD40 molecule co-operate in stimulation and can be used for the detection of soluble CD40. Immunol. 83(3):430-437. (1994).

Bojadzic et al., Toward Small-Molecule Inhibition of Protein-Protein Interactions: General Aspects and Recent Progress in Targeting Costimulatory and Coinhibitory (Immune Checkpoint) Interactions. Curr Top Med Chem. 18 (8):674-699. (2018).

Bosson et al., Interactions of tumor necrosis factor (TNF) and TNF receptor family members in the mouse and human. J. Biol. Chem. 281(20): 13964-13971. (2006).

Caux et al., Activation of Human Dendritic Cells through CD40 Cross-linking. J Experimental Medicine. 180 (4):1263-1272. (1994).

Cella et al., Ligation of CD40 on dendritic cells triggers production of high levels of interkeulin-12 and enhances T cell stimulatory capacity: T-T help via APC activation. J. Exp. Med. 184(2):747-752. (1996).

Centi et al., Aptamer-based detection of plasma proteins by an electrochemical assay coupled to magnetic beads. Anal. Chem. 79(4):1466-1473. (2007).

Chatterjee et al., Internalization and endosomal degradation of receptor-bound antigens regulate the efficiency of cross presentation by human dendritic cells. Blood. 120(10):2011-20. (2012).

Chen et al., Immunization of chickens with an agonistic monoclonal anti-chicken CD40 antibody-hapten complex: rapid and robust IgG response induced by a single subcutaneous injection. J Immunol Methods. 378(1-2):116-120. (2012).

Chen et al., Production and characterization of agonistic monoclonal antibodies against chicken CD40. Dev Comp Immunol. 34(11):1139-1143. (2010).

Chen et al., Production and characterization of an agonistic single-chain antibody against chicken CD40. Poultry Science. 90(E-Suppl. 1):73. (2011).

Chou et al., Significant mucosal sIgA production after a single oral or parenteral administration using in vivo CD40 targeting in the chicken. Res. Vet. Sci. 108:112-115. (2016).

Corthay, A three-cell model for activation of naïve T helper. Scand. J. Immunol. 64(2):93-96. (2006).

Curtsinger et al. Inflammatory cytokines provide a third signal for activation of naïve CD4+ and CD8+ T cells. J. Immunol. 162(6):3256-3262. (1999).

Dahan et al., Therapeutic Activity of Agonistic, Human Anti-CD40 Monoclonal Antibodies Requires Selective FcγR Engagement. Cancer Cell. 29(6):820-831. (2016).

Dollins et al., Aptamers in immunotherapy. Hum. Gene Ther. 19(5), 443-450. (2008).

Elgueta et al., Molecular mechanism and function of CD40/CD40L engagement in the immune system. Immunol. Rev. 229(1):152-172. (2009).

Ellington et al., In vitro selection of RNA molecules that bind specific ligands. Nature. 346(6287):818-822. (1990).

Erf, Cell-mediated immunity in poultry. Poult. Sci. 83(4):580-590. (2004).

Fecteau et al., CD40 Stimulation of Human Peripheral B Lymphocytes: Distinct Response from Naïve and Memory Cells. J Immunol. 171(9):4621-4629. (2003).

Fernandez-Cabezudo et al., Evidence for the requirement for CD40-CD154 interactions in resistance to infections with attenuated *Salmonella*, J. Endotoxin Res. 11(6):395-399. (2005).

Foy et al., Immune regulation by CD40 and its ligand GP39. Annu. Rev. Immunol. 14, 591-617. (1996).

Gardell et al., CD40L is transferred to antigen-presenting B cells during delivery of T-cell help. Eur. J. Immunol. 47 (1):41-50. (2017).

Gares et al., Immunotargeting with CD154 (CD40 ligand) enhances DNA vaccine responses in ducks, Clin. Vaccine Immun. 13(8):958-965. (2006).

Grassmé et al., Clustering of CD40 ligand is required to form functional contact with CD40. J. Biol Chem. 277 (33):30289-30299. (2002).

Grewal et al., CD40 and CD154 in cell-mediated immunity. Annu. Rev. Immunology. 16(1):111-135. (1998).

Han et al., Cellular interaction in germinal centers. Roles of CD40 ligand and B7-2 in established germinal center. J. Immunol. 155(2): 556-567. (1995).

Harcourt et al., CD40 ligand (CD154) improves the durability of respiratory syncytial virus DNA vaccination in BALB/c mice. Vaccine. 21(21-22):2964-2979. (2003).

Hatzifoti et al., CD40-mediated enhancement of immune responses against three forms of influenza vaccine. Immunology. 122(1):98-106. (2007).

Hermann et al., Adaptive recognition by nucleic acid aptamers. Science. 287(5454):820-825. (2000).

Holmgren et al., Mucosal immunity: implications for vaccine development. Immunobiol. 184(2-3):157-179. (1992).

(56) References Cited

OTHER PUBLICATIONS

International Searching Authority, International Search Report and Written Opinion for International Application PCT/US2020/027970, mailed Jul. 24, 2020.

Irvine et al., SELEXION. Systemic evolution of ligands by exponential enrichment with integrated optimization by non-linear analysis. J. Mol. Biol. 222(3):739-761. (1991).

Jayasena, Aptamers: an emerging class of molecules that rival antibodies in diagnostics. 45(9):1628-1650. (1999).

Jeddi et al., Three-dimensional modeling of single stranded DNA hairpins for aptamer-based biosensors. Scientific Reports. 7(1):1178. (2017).

Johne et al., Rolling-circle amplification of viral DNA genomes using phi29 polymerase. Tren. Microbiol. 17 (5):205-211. (2009).

Karpusas et al., 2 Å crystal structure of an extracellular fragment of human CD40 ligand. Structure. 3 (10):1031-1039. (1995).

Kawabe et al., CD40/CD40 ligand interactions in immune responses and pulmonary immunity. Nagoya J. Med. Sci. 73(3-4):69-78. (2011).

Kunii et al., Selection of DNA aptamers recognizing small cell lung cancer using living cell-SELEX. Roy Soc. Chem. 136, 1310-1312. (2011).

Lavelle et al., Delivery systems and adjuvants for oral vaccines. Expert Opin. Drug Deliv. 3(6):747-762. (2006).

Li et al., Inhibitory Fcγ receptor engagement drives adjuvant and anti-tumor activities of agonistic CD40 antibodies. Science. 333(6045):1030-1034. (2011).

Li, Synergistic antibody induction by antigen-CD40 ligand fusion protein as improved immunogen. Immunology. 115 (2):215-222. (2005).

Lv et al., Aptamer and rolling circle amplification-involved sandwich assay for platelet derived growth factor-BB with absorbance analysis. Anal. Methods. 7(5): 1855-1859. (2015).

Ma et al., The role of CD40 and CD40L in dendritic cells. Semin. Immunol. 21(5):265-272. (2009).

Martin et al., Characterization of a broadly reactive anti-CD40 agonistic monoclonal antibody for potential use as an adjuvant. PLoS ONE. 12(1):e0170504. (2017).

McNamara et al., Multivalent 4-1BB binding aptamers costimulate CD8+ T cells and inhibit tumor growth in mice. J. Clin. Invest. 118(1):376-386. (2008).

McWhirter et al., Crystallographic analysis of CD40 recognition and signaling by human TRAF2. Proc. Natl. Acad. Sci. USA. 96(15):8408-8413. (1999).

Merluzzi et al., CD40 stimulation induces Pax5/BSAP and EBF activation through a APE/Ref-1-dependent Redox mechanism. J. Biol. Chem. 279(3):1777-1786. (2004).

Mohsen et al., The discovery of rolling circle amplification and rolling circle transcription. Acc. Chem. Res. 49 (11):2540-2550. (2016).

Monsur Ali et al., Rolling circle amplification: a versatile tool for chemical biology, materials science and medicine. Chem. Soc. Rev. 43, 3324-3341. (2014).

Noelle et al., A 39-kDa protein on activated helper T cells binds CD40 and transduce the signal for cognate activation of B cells. Proc. Natl. Acad. Sci. 89(14):6550-6554. (1992).

Pastor et al., CD28 aptamers as powerful immune response modulators. Molecular Therapy—Nucleic Acids. 2:e98. (2013).

Randrianjatovo-Gbalou et al., Enzymatic synthesis of random sequences of RNA and RNA analogues by DNA polymerase theta mutants for the generation of aptamer libraries. Nucleic Acids Research. 46(12):6271-6284. (2018).

Reis E Sousa, Activation of dendritic cells: translating innate into adaptive immunity. Curr. Opin. Immunol. 16, 21-25. (2004).

Reyes-Moreno et al., CD40/CD40 homodimers are required for CD40-induced phosphatidylinositol 3 kinase-dependent expression of B7.2 by human B lymphocytes. J. Biol. Chem. 279(9):7799-7806. (2004).

Richman et al., Anti-human CD40 monoclonal antibody therapy is potent without FcR crosslinking. OncoImmunol 3 (5): e28610. (2014).

Richman et al., Role of crosslinking for agonistic CD40 monoclonal antibodies as immune therapy of cancer. Cancer Immunol. Res. 2(1): 19-26. (2014).

Sallusto et al., Efficient presentation of soluble antigen by cultured human dendritic cells is maintained by granulocyte/macrophage colony-stimulating factor plus interleukin 4 and downregulated by tumor necrosis factor α. J. Exp. Med. 179(4):1109-1118. (1994).

Schoenberger et al., T-cell help for cytotoxic T lymphocytes is mediated by CD40-CD40L interactions. Nature. 393(6684):480-483. (1998).

Schütze et al., Probing the SELEX process with next-generation sequencing. PLoS One. 6(12):e29604. (2011).

Soldevilla et al., 2-fluoro-RNA oligonucleotide CD40 targeted aptamers for the control of B lymphoma and bone-marrow aplasia. Biomaterials. 67:274-285. (2015).

Song et al., Aptamers and their biological applications. Sensors. 12(1):612-631. (2012).

Stout et al., The many roles of CD40 in cell-mediated inflammatory responses. Immunol. Today. 17(10):487-492. (1996).

Suttles et al., Macrophage CD40 signaling: a pivotal regulator of disease protection and pathogenesis. Semin. Immunol. 21(5):257-264. (2009).

Sypabekova et al., Selection, characterization, and application of DNA aptamers for detection of *Mycobacterium tuberculosis* secreted protein MPT64. Tuberculosis. 104:70-78. (2017).

Tai et al., Human anti-CD40 antagonist antibody triggers significant antitumor activity against human multiple myeloma. Cancer Res. 65(13):5898-5906. (2005).

Tregaskes et al., Conservation of biological properties of the CD40 ligand, CD154 in a non-mammalian vertebrate. Dev. Comp. Immunol. 29(4):361-374. (2005).

Tuerk et al., Systemic evolution of ligand by exponential enrichment: RNA ligands to bacteriophage T4 DNA polymerase. Science. 249(4968):505-510. (1990).

Van Kooten et al., CD40-CD40 ligand. J. Leukoc. Biol. 67(1):2-17. (2000).

Wang et al., Selection and characterization of DNA aptamers for use in detection of avian influenza virus H5N1. J. Virol. Meth. 189(2):362-369. (2013).

Zan et al., CCD40 Engagement Triggers Switching to IgA1 and IgA2 in Human B Cells Through Induction of Endogenous TGF-ß: Evidence for TGF-ß But Not IL-10-Dependent Direct Sμ-→Sα and Sequential Sμ-→Sγ, Sγ-→Sα DNA Recombination. J. Immunol. 161(10):5217-5225. (1998).

Zhang et al., Novel aptamers developed for breast cancer cell internalization. Chem. Med. Chem. 7(1):79-84. (2012).

Zhou et al., Aptamers as targeted therapeutics: current potential and challenges. Nat Rev Drug Discov. 16 (3):181-202. (2017).

* cited by examiner $\Delta G = -1.24$

Fig. 1C $\Delta G = -2.78$

MGRLGLLGLLCALLLGCGQPGDAVNCSDKQYEHKGRCCNRCQPGKKLASECNDTEDSVCTPCENGQYQHSWTKERHCTPH
EICEDNAGLIVKRHGNATHNTVCQCRAGMHCSDASCQTCVENEPCKQGFGFVAAMAEARMTSPCEPCAEGTFSNVSSKTEP
CHFWTSCEEKGLVKVKGTNTSDVICESSRRSSLSVLIPITAAVVTCLVGICIYCLVHTDLRRGPKQAEEAAPRELVTQQPEEVDF
PVQETLLGGQPVAQEDGKESRIAEQEQL (SEQ ID NO: 9)

Region 1

Region 2

Region 3

SEQUENCE LISTING

<160> NUMBER OF SEQ ID NOS: 80

<210> SEQ ID NO 1
<211> LENGTH: 80
<212> TYPE: DNA
<213> ORGANISM: Artificial Sequence
<220> FEATURE:
<223> OTHER INFORMATION: Synthetic- CD40 specific DNA aptamer

<400> SEQUENCE: 1
ccgaattcga aggacaagag cagacaaacg agtattagga cagaacggta gcacgactca      60
tcttttatgc tacgtcccgc      80

<210> SEQ ID NO 2
<211> LENGTH: 80
<212> TYPE: DNA
<213> ORGANISM: Artificial Sequence
<220> FEATURE:
<223> OTHER INFORMATION: Synthetic- CD40 specific DNA aptamer

<400> SEQUENCE: 2
ccgaattcga aggacaagag agaaaaaacg aatcccagga cagaccggcg tgtcgagtcc      60
tcttttatgc tacgtcccgc      80

<210> SEQ ID NO 3
<211> LENGTH: 80
<212> TYPE: DNA
<213> ORGANISM: Artificial Sequence
<220> FEATURE:
<223> OTHER INFORMATION: Synthetic- CD40 specific DNA aptamer

<400> SEQUENCE: 3
ccgaattcga aggacaagag gtggaattgg taatggggtg taaatggagc agtgaattcg      60
tcttttatgc tacgtcccgc      80

<210> SEQ ID NO 4
<211> LENGTH: 80
<212> TYPE: DNA
<213> ORGANISM: Artificial Sequence
<220> FEATURE:
<223> OTHER INFORMATION: Synthetic- CD40 specific DNA aptamer

<400> SEQUENCE: 4
ccgaattcga aggacaagag tagggctaca tggaataggg atcagaagag cagggctagg      60
tcttttatgc tacgtcccgc      80

<210> SEQ ID NO 5
<211> LENGTH: 78
<212> TYPE: DNA

```
<213> ORGANISM: Artificial Sequence
<220> FEATURE:
<223> OTHER INFORMATION: Synthetic- CD40 specific DNA aptamer

<400> SEQUENCE: 5
ccgaattcga aggacaagag taagtgcagt ttgggttttc ttttatgcta cgtcccgctc     60
ttttatgcta cgtcccgc                                                   78

<210> SEQ ID NO 6
<211> LENGTH: 80
<212> TYPE: DNA
<213> ORGANISM: Artificial Sequence
<220> FEATURE:
<223> OTHER INFORMATION: Synthetic- CD40 specific DNA aptamer

<400> SEQUENCE: 6
ccgaattcga aggacaagag gtaagtcacg acgtcctagg atgaccagtt ccgattgttc     60
tcttttatgc tacgtcccgc                                                 80

<210> SEQ ID NO 7
<211> LENGTH: 80
<212> TYPE: DNA
<213> ORGANISM: Artificial Sequence
<220> FEATURE:
<223> OTHER INFORMATION: Synthetic- CD40 specific DNA aptamer

<400> SEQUENCE: 7
ccgaattcga aggacaagag agatgaggga tgctgtcaag tcagtatggt tggtcatctc     60
tcttttatgc tacgtcccgc                                                 80

<210> SEQ ID NO 8
<211> LENGTH: 80
<212> TYPE: DNA
<213> ORGANISM: Artificial Sequence
<220> FEATURE:
<223> OTHER INFORMATION: Synthetic- CD40 specific DNA aptamer

<400> SEQUENCE: 8
ccgaattcga aggacaagag caacatttct tttacccta tcctttgcaa ctaccccat      60 tcttttatgc tacgtcccgc                                                 80

<210> SEQ ID NO 9
<211> LENGTH: 276
<212> TYPE: PRT
<213> ORGANISM: Gallus gallus
<220> FEATURE:
<221> NAME/KEY: MISC_FEATURE
<222> LOCATION: (1)..(276)
<223> OTHER INFORMATION: chicken CD40 extracellular domain (chCD40ED)

<400> SEQUENCE: 9

Met Gly Arg Leu Gly Leu Leu Gly Leu Leu Cys Ala Leu Leu Leu Gly
1               5                   10                  15

Cys Gly Gln Pro Gly Asp Ala Val Asn Cys Ser Asp Lys Gln Tyr Glu
                20                  25                  30

His Lys Gly Arg Cys Cys Asn Arg Cys Gln Pro Gly Lys Lys Leu Ala
            35                  40                  45

Ser Glu Cys Asn Asp Thr Glu Asp Ser Val Cys Thr Pro Cys Glu Asn
        50                  55                  60

Gly Gln Tyr Gln His Ser Trp Thr Lys Glu Arg His Cys Thr Pro His
65                  70                  75                  80
```

-continued

```
Glu Ile Cys Glu Asp Asn Ala Gly Leu Ile Val Lys Arg His Gly Asn
                85                  90                  95

Ala Thr His Asn Thr Val Cys Gln Cys Arg Ala Gly Met His Cys Ser
            100                 105                 110

Asp Ala Ser Cys Gln Thr Cys Val Glu Asn Glu Pro Cys Lys Gln Gly
            115                 120                 125

Phe Gly Phe Val Ala Ala Met Ala Glu Ala Arg Met Thr Ser Pro Cys
        130                 135                 140

Glu Pro Cys Ala Glu Gly Thr Phe Ser Asn Val Ser Ser Lys Thr Glu
145                 150                 155                 160

Pro Cys His Phe Trp Thr Ser Cys Glu Glu Lys Gly Leu Val Val Lys
                165                 170                 175

Val Lys Gly Thr Asn Thr Ser Asp Val Ile Cys Glu Ser Ser Arg Arg
            180                 185                 190

Ser Ser Leu Ser Val Leu Ile Pro Ile Thr Ala Ala Val Val Thr Cys
        195                 200                 205

Leu Val Gly Ile Cys Ile Tyr Cys Leu Val His Thr Asp Leu Arg Arg
        210                 215                 220

Arg Gly Pro Lys Gln Ala Glu Ala Glu Ala Pro Arg Glu Leu Val Thr
225                 230                 235                 240

Gln Gln Pro Glu Glu Val Asp Phe Pro Val Gln Glu Thr Leu Leu Gly
            245                 250                 255

Gly Gln Pro Val Ala Gln Glu Asp Gly Lys Glu Ser Arg Ile Ala Glu
            260                 265                 270

Gln Glu Gln Leu
        275

<210> SEQ ID NO 10
<211> LENGTH: 80
<212> TYPE: DNA
<213> ORGANISM: Artificial Sequence
<220> FEATURE:
<223> OTHER INFORMATION: Synthetic- generic ssDNA library sequence
      comprising 40 random nucleotides (N) flanked by forward and
      reverse primer binding sites
<220> FEATURE:
<221> NAME/KEY: misc_feature
<222> LOCATION: (21)..(60)
<223> OTHER INFORMATION: n is a, c, g, or t

<400> SEQUENCE: 10
ccgaattcga aggacaagag nnnnnnnnnn nnnnnnnnnn nnnnnnnnnn nnnnnnnnnn      60
tcttttatgc tacgtcccgc                                                 80

<210> SEQ ID NO 11
<211> LENGTH: 20
<212> TYPE: DNA
<213> ORGANISM: Artificial Sequence
<220> FEATURE:
<223> OTHER INFORMATION: Synthetic- forward primer for ssDNA library
      amplification

<400> SEQUENCE: 11
ccgaattcga aggacaagag                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic- reverse primer for ssDNA library
```

-continued amplification

<400> SEQUENCE: 12
ccgaattcga aggacaagag                                                      20

<210> SEQ ID NO 13
<211> LENGTH: 67
<212> TYPE: DNA
<213> ORGANISM: Artificial Sequence
<220> FEATURE:
<223> OTHER INFORMATION: Synthetic- forward primer for Illumina
      sequencing comprising barcode sequence (N)
<220> FEATURE:
<221> NAME/KEY: misc_feature
<222> LOCATION: (59)..(63)
<223> OTHER INFORMATION: n is a, c, g, or t

<400> SEQUENCE: 13
aatgatacgg cgaccaccga gatctacact ctttccctac acgacgctct tccgatctnn        60 nnnggtt                                                                    67

<210> SEQ ID NO 14
<211> LENGTH: 24
<212> TYPE: DNA
<213> ORGANISM: Artificial Sequence
<220> FEATURE:
<223> OTHER INFORMATION: Synthetic- reverse primer for Illumina
      sequencing

<400> SEQUENCE: 14
tagagcatac ggcagaagac gaac                                                 24

<210> SEQ ID NO 15
<211> LENGTH: 195
<212> TYPE: DNA
<213> ORGANISM: Artificial Sequence
<220> FEATURE:
<223> OTHER INFORMATION: Synthetic- RCA I template

<400> SEQUENCE: 15
gcatctgaac gcgggacgta gcataaaaga aggagacccg tatgcataac ggtgacacga        60
tcaagtcgaa ctcttgtcct tcgaattcgg gatccaccgg tagcagcggg acgtagcata       120
aaagaggaaa gtattcaagg ttaaaatgta cgtgtggacg cgaatctctt gtccttcgaa       180
ttcggggaac gtctt                                                          195

<210> SEQ ID NO 16
<211> LENGTH: 195
<212> TYPE: DNA
<213> ORGANISM: Artificial Sequence
<220> FEATURE:
<223> OTHER INFORMATION: Synthetic- RCA II template

<400> SEQUENCE: 16
gcatctgaac gcgggacgta gcataaaaga cgaattcact gctccattta caccccatta        60
ccaattccac ctcttgtcct tcgaattcgg gatccaccgg tagcagcggg acgtagcata       120
aaagacctag ccctgctctt ctgatcccta ttccatgtag ccctactctt gtccttcgaa       180
ttcggggaac gtctt                                                          195

<210> SEQ ID NO 17
<211> LENGTH: 193
<212> TYPE: DNA
<213> ORGANISM: Artificial Sequence

```
<220> FEATURE:
<223> OTHER INFORMATION: Synthetic- RCA III template

<400> SEQUENCE: 17
gcatctgaac gcgggacgta gcataaaaga gcgggacgta gcataaaaga aaacccaaac       60
tgcacttact cttgtccttc gaattcggga tccaccggta gcagcgggac gtagcataaa      120
agagaacaat cggaactggt catcctagga cgtcgtgact tacctcttgt ccttcgaatt      180
cggggaacgt ctt                                                         193

<210> SEQ ID NO 18
<211> LENGTH: 195
<212> TYPE: DNA
<213> ORGANISM: Artificial Sequence
<220> FEATURE:
<223> OTHER INFORMATION: Synthetic- RCA IV template

<400> SEQUENCE: 18
gcatctgaac gcgggacgta gcataaaaga cagatgacca accatactga cttgacagca       60
tccctcatct ctcttgtcct tcgaattcgg gatccaccgg tagcagcggg acgtagcata      120
aaagaatggg ggtagttgca aaggataggg gtaaaagaaa tgttgctctt gtccttcgaa      180
ttcggggaac gtctt                                                       195

<210> SEQ ID NO 19
<211> LENGTH: 115
<212> TYPE: DNA
<213> ORGANISM: Artificial Sequence
<220> FEATURE:
<223> OTHER INFORMATION: Synthetic- negative control RCA template

<400> SEQUENCE: 19
gcatctgaac atgggcagtt caaactacga catagcagac caaggtatag gatccaccgg       60
tagcatgatg caggtcctgt aattggactg atcacatacc tagatggaac gtctt          115

<210> SEQ ID NO 20
<211> LENGTH: 20
<212> TYPE: DNA
<213> ORGANISM: Artificial Sequence
<220> FEATURE:
<223> OTHER INFORMATION: Synthetic- RCA primer

<400> SEQUENCE: 20
gttcagatgc aagacgttcc                                                   20

<210> SEQ ID NO 21
<211> LENGTH: 15
<212> TYPE: DNA
<213> ORGANISM: Artificial Sequence
<220> FEATURE:
<223> OTHER INFORMATION: Synthetic- Spacer-complement

<400> SEQUENCE: 21
gatccaccgg tagca                                                        15

<210> SEQ ID NO 22
<211> LENGTH: 16
<212> TYPE: PRT
<213> ORGANISM: Avian influenza virus
<220> FEATURE:
<221> NAME/KEY: MISC_FEATURE
<222> LOCATION: (1)..(16)
<223> OTHER INFORMATION: Ectodomain of matrix protein 2 (M2e)
```

-continued

<400> SEQUENCE: 22

Asn Ala Trp Ser Lys Glu Tyr Ala Arg Gly Phe Ala Lys Thr Gly Lys
1               5                   10                  15

<210> SEQ ID NO 23
<211> LENGTH: 40
<212> TYPE: DNA
<213> ORGANISM: Artificial Sequence
<220> FEATURE:
<223> OTHER INFORMATION: Synthetic- Consensus sequence of SEQ ID NO: 24
      and SEQ ID NO: 25
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 23
nnnanaaacg antnnnagga cagancggnn nnncgantcn                            40

<210> SEQ ID NO 24
<211> LENGTH: 40
<212> TYPE: DNA
<213> ORGANISM: Artificial Sequence
<220> FEATURE:
<223> OTHER INFORMATION: Synthetic- randomized portion of the CD40
      specific DNA aptamer of SEQ ID NO: 1

<400> SEQUENCE: 24
cagacaaacg agtattagga cagaacggta gcacgactca                            40

<210> SEQ ID NO 25
<211> LENGTH: 40
<212> TYPE: DNA
<213> ORGANISM: Artificial Sequence
<220> FEATURE:
<223> OTHER INFORMATION: Synthetic- randomized portion of the CD40
      specific DNA aptamer of SEQ ID NO: 2

<400> SEQUENCE: 25
agaaaaaacg aatcccagga cagaccggcg tgtcgagtcc                            40

<210> SEQ ID NO 26
<211> LENGTH: 182

```
<212> TYPE: PRT
<213> ORGANISM: Gallus gallus
<220> FEATURE:
<221> NAME/KEY: MISC_FEATURE
<222> LOCATION: (1)..(182)
<223> OTHER INFORMATION: Clostridium perfringens antigen

<400> SEQUENCE: 26

Ser Lys Glu Tyr Ala Arg Gly Phe Ala Lys Thr Gly Lys Ser Ile Tyr
1               5                   10                  15

Tyr Ser His Ala Ser Met Ser His Ser Trp Asp Asp Trp Asp Tyr Ala
            20                  25                  30

Ala Lys Val Thr Leu Ala Asn Ser Gln Lys Gly Thr Ala Gly Tyr Ile
        35                  40                  45

Tyr Arg Phe Leu His Asp Val Ser Glu Gly Asn Asp Pro Ser Val Gly
    50                  55                  60

Lys Asn Val Lys Glu Leu Val Ala Tyr Ile Ser Thr Ser Gly Glu Lys
65                  70                  75                  80

Asp Ala Gly Thr Asp Asp Tyr Met Tyr Phe Gly Ile Lys Thr Lys Asp
                85                  90                  95

Gly Lys Thr Gln Glu Trp Glu Met Asp Asn Pro Gly Asn Asp Phe Met
            100                 105                 110

Thr Gly Ser Lys Asp Thr Tyr Thr Phe Lys Leu Lys Asp Glu Asn Leu
            115                 120                 125

Lys Ile Asp Asp Ile Gln Asn Met Trp Ile Arg Lys Arg Lys Tyr Thr
    130                 135                 140

Ala Phe Pro Asp Ala Tyr Lys Pro Glu Asn Ile Lys Val Ile Ala Asn
145                 150                 155                 160

Gly Lys Val Val Val Asp Lys Asp Ile Asn Glu Trp Ile Ser Gly Asn
                165                 170                 175

Ser Thr Tyr Asn Ile Lys
            180

<210> SEQ ID NO 27
<211> LENGTH: 6
<212> TYPE: PRT
<213> ORGANISM: Clostridium perfringens
<220> FEATURE:
<221> NAME/KEY: MISC_FEATURE
<222> LOCATION: (1)..(6)
<223> OTHER INFORMATION: Protective epitope of CPa

<400> SEQUENCE: 27

Ala Arg Gly Phe Ala Lys
1               5

<210> SEQ ID NO 28
<211> LENGTH: 7
<212> TYPE: PRT
<213> ORGANISM: Avian influenza virus
<220> FEATURE:
<221> NAME/KEY: MISC_FEATURE
<222> LOCATION: (1)..(7)
<223> OTHER INFORMATION: Avian Influenza virus m2e

<400> SEQUENCE: 28

Val Glu Thr Pro Ile Arg Asn
1               5

<210> SEQ ID NO 29
<211> LENGTH: 8
<212> TYPE: PRT
```

```
<213> ORGANISM: Avian influenza virus
<220> FEATURE:
<221> NAME/KEY: MISC_FEATURE
<222> LOCATION: (1)..(8)
<223> OTHER INFORMATION: Avian Influenza virus m2e

<400> SEQUENCE: 29

Glu Val Glu Thr Pro Thr Arg Asn
1               5

<210> SEQ ID NO 30
<211> LENGTH: 12
<212> TYPE: PRT
<213> ORGANISM: Avian influenza virus
<220> FEATURE:
<221> NAME/KEY: MISC_FEATURE
<222> LOCATION: (1)..(12)
<223> OTHER INFORMATION: Avian Influenza virus (HA5 UA)

<400> SEQUENCE: 30

Leu Leu Ser Arg Ile Asn His Phe Glu Lys Ile Gln
1               5                   10

<210> SEQ ID NO 31
<211> LENGTH: 19
<212> TYPE: PRT
<213> ORGANISM: Avian influenza virus
<220> FEATURE:
<221> NAME/KEY: MISC_FEATURE
<222> LOCATION: (1)..(19)
<223> OTHER INFORMATION: Avian Influenza virus (HA5 LB)

<400> SEQUENCE: 31

Ala Asn Pro Ala Asn Asp Leu Cys Tyr Pro Gly Asp Phe Asn Asp Tyr
1               5                   10                  15

Glu Glu Leu

<210> SEQ ID NO 32
<211> LENGTH: 16
<212> TYPE: PRT
<213> ORGANISM: Avian influenza virus
<220> FEATURE:
<221> NAME/KEY: MISC_FEATURE
<222> LOCATION: (1)..(16)
<223> OTHER INFORMATION: Avian Influenza virus (NP 54-69)

<400> SEQUENCE: 32

Gly Arg Leu Ile Gln Asn Ser Ile Thr Ile Glu Arg Met Val Leu Ser
1               5                   10                  15

<210> SEQ ID NO 33
<211> LENGTH: 14
<212> TYPE: PRT
<213> ORGANISM: Avian influenza virus
<220> FEATURE:
<221> NAME/KEY: MISC_FEATURE
<222> LOCATION: (1)..(14)
<223> OTHER INFORMATION: Avian Influenza virus (NP 147-160)

<400> SEQUENCE: 33

Thr Tyr Gln Arg Thr Arg Ala Leu Val Arg Thr Gly Met Asp
1               5                   10

<210> SEQ ID NO 34
<211> LENGTH: 19
<212> TYPE: PRT
<213> ORGANISM: Escherichia coli
<220> FEATURE:
```

```
<221> NAME/KEY: MISC_FEATURE
<222> LOCATION: (1)..(19)
<223> OTHER INFORMATION: PAL bis from E. coli

<400> SEQUENCE: 34

Glu Gly His Ala Asp Glu Arg Gly Thr Pro Glu Tyr Asn Ile Ser Leu
1               5                   10                  15

Gly Glu Arg

<210> SEQ ID NO 35
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 35

Gly His Ala Asp Glu Arg
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 36

Asp Glu Arg Gly Thr Pro
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 37

Glu Tyr Asn Ile Ser Leu
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic: peptide

<400> SEQUENCE: 38

Ile Ser Leu Gly Glu Arg
1               5

<210> SEQ ID NO 39
<211> LENGTH: 19
<212> TYPE: PRT
<213> ORGANISM: Vibrio spp.
<220> FEATURE:
<221> NAME/KEY: MISC_FEATURE
<222> LOCATION: (1)..(19)
<223> OTHER INFORMATION: PALbis from vibrio spp.

<400> SEQUENCE: 39

Glu Gly His Ala Asp Glu Arg Gly Thr Pro Glu Tyr Asn Ile Ala Leu
1               5                   10                  15

Gly Glu Arg
```

```
<210> SEQ ID NO 40
<211> LENGTH: 17
<212> TYPE: PRT
<213> ORGANISM: Campylobacter spp.
<220> FEATURE:
<221> NAME/KEY: MISC_FEATURE
<222> LOCATION: (1)..(17)
<223> OTHER INFORMATION: corresponding peptide from Campylobacter spp.

<400> SEQUENCE: 40

Glu Gly Asn Cys Asp Glu Trp Gly Thr Asp Glu Tyr Asn Gln Ala Leu
1               5                   10                  15

Gly

<210> SEQ ID NO 41
<211> LENGTH: 19
<212> TYPE: PRT
<213> ORGANISM: Escherichia coli
<220> FEATURE:
<221> NAME/KEY: MISC_FEATURE
<222> LOCATION: (1)..(19)
<223> OTHER INFORMATION: PAL from E. coli

<400> SEQUENCE: 41

Thr Val Glu Gly His Ala Asp Glu Arg Gly Thr Pro Glu Tyr Asn Ile
1               5                   10                  15

Ser Leu Gly

<210> SEQ ID NO 42
<211> LENGTH: 21
<212> TYPE: PRT
<213> ORGANISM: Campylobacter jejuni
<220> FEATURE:
<221> NAME/KEY: MISC_FEATURE
<222> LOCATION: (1)..(21)
<223> OTHER INFORMATION: Campylobacter jejuni Cj0113

<400> SEQUENCE: 42

Gly Val Ser Ile Thr Val Glu Gly Asn Cys Asp Glu Trp Gly Thr Asp
1               5                   10                  15

Glu Tyr Asn Gln Ala
            20

<210> SEQ ID NO 43
<211> LENGTH: 19
<212> TYPE: PRT
<213> ORGANISM: Vibrio spp.
<220> FEATURE:
<221> NAME/KEY: MISC_FEATURE
<222> LOCATION: (1)..(19)
<223> OTHER INFORMATION: Vibrio spp. alternative PAL epitope

<400> SEQUENCE: 43

Thr Val Glu Gly His Ala Asp Glu Arg Gly Thr Pro Glu Tyr Asn Ile
1               5                   10                  15

Ala Leu Gly

<210> SEQ ID NO 44
<211> LENGTH: 57
<212> TYPE: DNA
<213> ORGANISM: Escherichia coli
<220> FEATURE:
<221> NAME/KEY: misc_feature
<222> LOCATION: (1)..(57)
<223> OTHER INFORMATION: E. coli nucleotide sequence for PAL epitope
```

-continued

```
<400> SEQUENCE: 44
gaaggtcacg cggacgaacg tggtaccccg gaatacaaca tctctctggg tgaacgt          57

<210> SEQ ID NO 45
<211> LENGTH: 9
<212> TYPE: PRT
<213> ORGANISM: Escherichia coli
<220> FEATURE:
<221> NAME/KEY: MISC_FEATURE
<222> LOCATION: (1)..(9)
<223> OTHER INFORMATION: Epitope of PAL from E. coli

<400> SEQUENCE: 45

Glu Tyr Asn Ile Ser Leu Gly Glu Arg
1               5

<210> SEQ ID NO 46
<211> LENGTH: 9
<212> TYPE: PRT
<213> ORGANISM: Vibrio spp.
<220> FEATURE:
<221> NAME/KEY: MISC_FEATURE
<222> LOCATION: (1)..(9)
<223> OTHER INFORMATION: Epitope of PAL from Vibrio spp.

<400> SEQUENCE: 46

Glu Tyr Asn Ile Ala Leu Gly Glu Arg
1               5

<210> SEQ ID NO 47
<211> LENGTH: 16
<212> TYPE: PRT
<213> ORGANISM: Artificial Sequence
<220> FEATURE:
<223> OTHER INFORMATION: Synthetic: composite minimal epitope
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 47

Pro Xaa Xaa Xaa Xaa Xaa Gly Tyr Gly Ala Cys Glu Xaa Asn Leu Gly
1               5                   10                  15

<210> SEQ ID NO 48
<211> LENGTH: 43
<212> TYPE: PRT
<213> ORGANISM: Eimeria maxima
<220> FEATURE:
<221> NAME/KEY: MISC_FEATURE
<222> LOCATION: (1)..(43)
<223> OTHER INFORMATION: Eimeria maxima MPP

<400> SEQUENCE: 48

Pro Ser His Asp Ala Pro Glu Ser Glu Arg Thr Pro Arg Val Ile Ser
1               5                   10                  15

Phe Gly Tyr Gly Ala Cys Glu His Asn Leu Gly Val Ser Leu Phe Arg
            20                  25                  30

Arg Glu Glu Thr Lys Lys Asp Pro Arg Gly Arg
        35                  40

<210> SEQ ID NO 49
```

```
<211> LENGTH: 28
<212> TYPE: PRT
<213> ORGANISM: Neospora canium

<400> SEQUENCE: 49

Pro Arg Ile Val Ser Phe Gly Tyr Gly Ala Cys Glu His Asn Leu Gly
1               5                   10                  15

Met Ser Leu Tyr Asp Arg Gln Gly Leu Gln Arg Gln
            20                  25

<210> SEQ ID NO 50
<211> LENGTH: 21
<212> TYPE: PRT
<213> ORGANISM: Eimeria tenella

<400> SEQUENCE: 50

Glu Ser Gln Arg Ala Pro Met Val Ile Arg Tyr Gly Tyr Gly Ala Cys
1               5                   10                  15

Glu Tyr Asn Leu Gly
            20

<210> SEQ ID NO 51
<211> LENGTH: 10
<212> TYPE: PRT
<213> ORGANISM: Eimeria maxima
<220> FEATURE:
<221> NAME/KEY: MISC_FEATURE
<222> LOCATION: (1)..(10)
<223> OTHER INFORMATION: Eimeria maxima TRAP-1

<400> SEQUENCE: 51

Gly Gly Gly Phe Pro Thr Ala Ala Val Ala
1               5                   10

<210> SEQ ID NO 52
<211> LENGTH: 40
<212> TYPE: PRT
<213> ORGANISM: Eimeria maxima
<220> FEATURE:
<221> NAME/KEY: MISC_FEATURE
<222> LOCATION: (1)..(40)
<223> OTHER INFORMATION: Eimeria maxima TRAP-02

<400> SEQUENCE: 52

Ala Ala Pro Glu Thr Pro Ala Val Gln Pro Lys Pro Glu Glu Gly His
1               5                   10                  15

Glu Arg Pro Glu Pro Glu Glu Glu Glu Lys Lys Glu Glu Gly Gly
            20                  25                  30

Gly Phe Pro Thr Ala Ala Val Ala
        35                  40

<210> SEQ ID NO 53
<211> LENGTH: 40
<212> TYPE: PRT
<213> ORGANISM: Eimeria maxima
<220> FEATURE:
<221> NAME/KEY: MISC_FEATURE
<222> LOCATION: (1)..(40)
<223> OTHER INFORMATION: Eimeria maxima TRAP-03

<400> SEQUENCE: 53

Gly Gly Gly Phe Pro Thr Ala Ala Val Ala Gly Gly Val Gly Gly Val
1               5                   10                  15

Leu Leu Ile Ala Ala Val Gly Gly Gly Val Ala Ala Phe Thr Ser Gly
            20                  25                  30
```

```
Gly Gly Gly Ala Gly Ala Gln Glu
        35                  40

<210> SEQ ID NO 54
<211> LENGTH: 21
<212> TYPE: PRT
<213> ORGANISM: Campylobacter jejuni
<220> FEATURE:
<221> NAME/KEY: MISC_FEATURE
<222> LOCATION: (1)..(21)
<223> OTHER INFORMATION: Campylobacter jejuni Cj0982

<400> SEQUENCE: 54

Lys Asp Ile Val Leu Asp Ala Glu Ile Gly Gly Val Ala Lys Gly Lys
1               5                   10                  15

Asp Gly Lys Glu Lys
            20

<210> SEQ ID NO 55
<211> LENGTH: 35
<212> TYPE: PRT
<213> ORGANISM: Campylobacter jejuni
<220> FEATURE:
<221> NAME/KEY: MISC_FEATURE
<222> LOCATION: (1)..(35)
<223> OTHER INFORMATION: Campylobacter jejuni Cj0420

<400> SEQUENCE: 55

Lys Val Ala Leu Gly Val Ala Val Pro Lys Asp Ser Asn Ile Thr Ser
1               5                   10                  15

Val Glu Asp Leu Lys Asp Lys Thr Leu Leu Leu Asn Lys Gly Thr Thr
            20                  25                  30

Ala Asp Ala
        35

<210> SEQ ID NO 56
<211> LENGTH: 16
<212> TYPE: PRT
<213> ORGANISM: Clostridium perfringens
<220> FEATURE:
<221> NAME/KEY: MISC_FEATURE
<222> LOCATION: (1)..(16)
<223> OTHER INFORMATION: Clostridium perfringens Alpha toxin

<400> SEQUENCE: 56

Asn Ala Trp Ser Lys Glu Tyr Ala Arg Gly Phe Ala Lys Thr Gly Lys
1               5                   10                  15

<210> SEQ ID NO 57
<211> LENGTH: 9
<212> TYPE: PRT
<213> ORGANISM: Avian influenza virus
<220> FEATURE:
<221> NAME/KEY: MISC_FEATURE
<222> LOCATION: (1)..(9)
<223> OTHER INFORMATION: Avian influenza M2e peptide

<400> SEQUENCE: 57

Cys Glu Val Glu Thr Pro Thr Arg Asn
1               5

<210> SEQ ID NO 58
<211> LENGTH: 9
<212> TYPE: PRT
<213> ORGANISM: Clostridium perfringens
<220> FEATURE:
```

-continued

```
<221> NAME/KEY: MISC_FEATURE
<222> LOCATION: (1)..(9)
<223> OTHER INFORMATION: 1-Alpha-31

<400> SEQUENCE: 58

Gly Lys Ile Asp Gly Thr Gly Thr His
1               5

<210> SEQ ID NO 59
<211> LENGTH: 15
<212> TYPE: PRT
<213> ORGANISM: Clostridium perfringens
<220> FEATURE:
<221> NAME/KEY: MISC_FEATURE
<222> LOCATION: (1)..(15)
<223> OTHER INFORMATION: 2-Alpha-51

<400> SEQUENCE: 59

Glu Asn Asp Met Ser Lys Asn Glu Pro Glu Ser Val Arg Lys Asn
1               5                   10                  15

<210> SEQ ID NO 60
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 3-Alpha-71

<400> SEQUENCE: 60

Glu Asn Met His Glu Leu Gln Leu Gly Ser Thr Tyr Pro Asp Tyr Asp
1               5                   10                  15

Lys Asn Ala Tyr
            20

<210> SEQ ID NO 61
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 4-Alpha-81

<400> SEQUENCE: 61

Thr Tyr Pro Asp Tyr Asp Lys Asn Ala Tyr Asp Leu Tyr Gln Asp His
1               5                   10                  15

Phe Trp Asp Pro
            20

<210> SEQ ID NO 62
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 5-Alpha-91

<400> SEQUENCE: 62

Asp Leu Tyr Gln Asp His Phe Trp Asp Pro Asp Thr Asp Asn Asn Phe
1               5                   10                  15

Ser Lys Asp Asn
            20
```

-continued

```
<210> SEQ ID NO 63
<211> LENGTH: 10
<212> TYPE: PRT
<213> ORGANISM: Clostridium perfringens
<220> FEATURE:
<221> NAME/KEY: MISC_FEATURE
<222> LOCATION: (1)..(10)
<223> OTHER INFORMATION: 6-Alpha-117

<400> SEQUENCE: 63

Ile Pro Asp Thr Gly Glu Ser Gln Ile Arg
1               5                   10

<210> SEQ ID NO 64
<211> LENGTH: 10
<212> TYPE: PRT
<213> ORGANISM: Clostridium perfringens
<220> FEATURE:
<221> NAME/KEY: MISC_FEATURE
<222> LOCATION: (1)..(10)
<223> OTHER INFORMATION: 7-Alpha-136

<400> SEQUENCE: 64

Glu Trp Gln Arg Gly Asn Tyr Lys Gln Ala
1               5                   10

<210> SEQ ID NO 65
<211> LENGTH: 23
<212> TYPE: PRT
<213> ORGANISM: Clostridium perfringens
<220> FEATURE:
<221> NAME/KEY: MISC_FEATURE
<222> LOCATION: (1)..(23)
<223> OTHER INFORMATION: 8-Alpha-158

<400> SEQUENCE: 65

Asp Ile Asp Thr Pro Tyr His Pro Ala Asn Val Thr Ala Val Asp Ser
1               5                   10                  15

Ala Gly His Val Lys Phe Glu
            20

<210> SEQ ID NO 66
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 9-Alpha-170

<400> SEQUENCE: 66

Val Asp Ser Ala Gly His Val Lys Phe Glu Thr Phe Ala Glu Glu Arg
1               5                   10                  15

Lys Glu Gln Tyr
            20

<210> SEQ ID NO 67
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 10-Alpha-181

<400> SEQUENCE: 67

Thr Phe Ala Glu Glu Arg Lys Glu Gln Tyr Lys Ile Asn Thr Ala Gly
1               5                   10                  15
```

```
Cys Lys Thr Asn
            20

<210> SEQ ID NO 68
<211> LENGTH: 21
<212> TYPE: PRT
<213> ORGANISM: Clostridium perfringens
<220> FEATURE:
<221> NAME/KEY: MISC_FEATURE
<222> LOCATION: (1)..(21)
<223> OTHER INFORMATION: 11-Alpha-191

<400> SEQUENCE: 68

Lys Ile Asn Thr Val Gly Cys Lys Thr Asn Glu Asp Phe Tyr Ala Asp
1               5                   10                  15

Ile Leu Lys Asn Lys
            20

<210> SEQ ID NO 69
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 12-Alpha-200

<400> SEQUENCE: 69

Glu Asp Phe Tyr Ala Asp Ile Leu Lys Asn Lys Asp Phe Asn Ala Trp
1               5                   10                  15

Ser Lys Glu Tyr
            20

<210> SEQ ID NO 70
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 13-Alpha-210

<400> SEQUENCE: 70

Lys Asp Phe Asn Ala Trp Ser Lys Glu Tyr Ala Arg Gly Phe Ala Lys
1               5                   10                  15

Thr Gly Lys Ser
            20

<210> SEQ ID NO 71
<211> LENGTH: 17
<212> TYPE: PRT
<213> ORGANISM: Clostridium perfringens
<220> FEATURE:
<221> NAME/KEY: MISC_FEATURE
<222> LOCATION: (1)..(17)
<223> OTHER INFORMATION: 14-Alpha-220

<400> SEQUENCE: 71

Ala Arg Gly Phe Ala Lys Thr Gly Lys Ser Ile Tyr Tyr Ser His Ala
1               5                   10                  15

Ser

<210> SEQ ID NO 72
<211> LENGTH: 17
<212> TYPE: PRT
```

<213> ORGANISM: Clostridium perfringens
<220> FEATURE:
<221> NAME/KEY: MISC_FEATURE
<222> LOCATION: (1)..(17)
<223> OTHER INFORMATION: 15-Alpha-233

<400> SEQUENCE: 72

Ser His Ala Ser Met Ser His Ser Trp Asp Asp Trp Asp Tyr Ala Ala
1               5                   10                  15

Lys

<210> SEQ ID NO 73
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 16-Alpha-240

<400> SEQUENCE: 73

Ser Trp Asp Asp Trp Asp Tyr Ala Ala Lys Val Thr Leu Ala Asn Ser
1               5                   10                  15

Gln Lys Gly Thr
            20

<210> SEQ ID NO 74
<211> LENGTH: 16
<212> TYPE: PRT
<213> ORGANISM: Clostridium perfringens
<220> FEATURE:
<221> NAME/KEY: MISC_FEATURE
<222> LOCATION: (1)..(16)
<223> OTHER INFORMATION: 17-Alpha-270

<400> SEQUENCE: 74

Asp Val Ser Glu Gly Asn Asp Pro Ser Val Gly Asn Asn Val Lys Glu
1               5                   10                  15

<210> SEQ ID NO 75
<211> LENGTH: 12
<212> TYPE: PRT
<213> ORGANISM: Clostridium perfringens
<220> FEATURE:
<221> NAME/KEY: MISC_FEATURE
<222> LOCATION: (1)..(12)
<223> OTHER INFORMATION: 18-Alpha-291

<400> SEQUENCE: 75

Ser Thr Ser Gly Glu Lys Asp Ala Gly Thr Asp Asp
1               5                   10

<210> SEQ ID NO 76
<211> LENGTH: 13
<212> TYPE: PRT
<213> ORGANISM: Clostridium perfringens
<220> FEATURE:
<221> NAME/KEY: MISC_FEATURE
<222> LOCATION: (1)..(13)
<223> OTHER INFORMATION: 19-Alpha-309

<400> SEQUENCE: 76

Lys Thr Lys Asp Gly Lys Thr Gln Glu Trp Glu Met Asp
1               5                   10

<210> SEQ ID NO 77
<211> LENGTH: 21

-continued

```
<212> TYPE: PRT
<213> ORGANISM: Clostridium perfringens
<220> FEATURE:
<221> NAME/KEY: MISC_FEATURE
<222> LOCATION: (1)..(21)
<223> OTHER INFORMATION: 20-Alpha-320

<400> SEQUENCE: 77

Asp Asn Pro Gly Asn Asp Phe Met Ala Gly Ser Lys Asp Thr Tyr Thr
1               5                   10                  15

Phe Lys Leu Lys Asp
            20

<210> SEQ ID NO 78
<211> LENGTH: 20
<212> TYPE: PRT
<213> ORGANISM: Clostridium perfringens
<220> FEATURE:
<221> NAME/KEY: MISC_FEATURE
<222> LOCATION: (1)..(20)
<223> OTHER INFORMATION: 21-Alpha-330

<400> SEQUENCE: 78

Ser Lys Asp Thr Tyr Thr Phe Lys Leu Lys Asp Glu Asn Leu Lys Ile
1               5                   10                  15

Asp Asp Ile Gln
            20

<210> SEQ ID NO 79
<211> LENGTH: 16
<212> TYPE: PRT
<213> ORGANISM: Clostridium perfringens
<220> FEATURE:
<221> NAME/KEY: MISC_FEATURE
<222> LOCATION: (1)..(16)
<223> OTHER INFORMATION: 22-Alpha-354

<400> SEQUENCE: 79

Arg Lys Arg Lys Tyr Thr Ala Phe Pro Asp Ala Tyr Lys Pro Glu Asn
1               5                   10                  15

<210> SEQ ID NO 80
<211> LENGTH: 19
<212> TYPE: PRT
<213> ORGANISM: Clostridium perfringens
<220> FEATURE:
<221> NAME/KEY: MISC_FEATURE
<222> LOCATION: (1)..(19)
<223> OTHER INFORMATION: 23-Alpha-379

<400> SEQUENCE: 80

Val Val Asp Lys Asp Ile Asn Glu Trp Ile Ser Gly Asn Ser Thr Tyr
1               5                   10                  15

Asn Ile Lys
```

CD40 SPECIFIC DNA APTAMERS AS VACCINE ADJUVANTS

CROSS-REFERENCE TO RELATED APPLICATIONS

This patent application is a national stage filing under 35 U.S.C. § 371 of International Patent Application No. PCT/US2020/027970, filed Apr. 13, 2020, which claims the benefit of priority of U.S. Provisional Patent Application No. 62/832,725, filed Apr. 11, 2019, and U.S. Provisional Patent Application No. 62/952,802, filed Dec. 23, 2019, all of which are incorporated herein by reference in their entirety.

SEQUENCE LISTING

A Sequence Listing accompanies this application and is submitted as an ASCII text file of the sequence listing named "169946-00549_ST25.txt" which is 28.5 kb in size and was created on Apr. 13, 2020. The sequence listing is electronically submitted via EFS-Web with the application and is incorporated herein by reference in its entirety.

BACKGROUND

Cluster of differentiation 40 (CD40) is a costimulatory receptor that is expressed on antigen presenting cells (APCs) for regulation of the acquired immune response. The ligand for the CD40 receptor (CD40L/CD154) is transiently expressed by activated CD4$^+$ T helper (T$_H$) lymphocytes[15]. Four signals are required to initiate an adaptive immune response. The first signal occurs during an innate immune response when pattern recognition receptors (PRRs) detect cognate pathogen-associated molecular patterns (PAMPs) associated with microbial pathogens, and initiate chemokine signaling and engulfment of foreign peptides by immature dendritic cells (DCs) in peripheral tissues[6, 7]. This first signal initiates DC maturation, in which DCs process and present the foreign peptide on major histocompatibility complex class II (MHC class II) molecules at their surface. Maturing DCs change their cytokine production profile and migrate to T zones at draining lymph nodes, where they exhibit less phagocytic capacity and more antigen-presenting activity. The second signal results from the engagement of a naïve T cell receptor with a processed foreign peptide presented by a DC. This engagement activates the T cell and causes it to transiently express CD40L along with other costimulatory molecules and cytokines. Crosslinking of these costimulatory molecules serves as the third signal, leading to downstream cell signaling in both the DC and T cell. Cytokines produced by the DC, such as interleukin (IL)-1 and IL-2, serve as the fourth signal, stimulating T cell differentiation. At the same time, activated T cells produce cytokines, such as IL-2 and IL-4, which influence the activity of local cells. The type of cytokines generated by the T cells depends on the type of foreign peptide that was initially presented by the DC. Importantly, the second, antigen-specific signal alone is not sufficient to stimulate full differentiation of naïve T cell into effector T$_H$ cells, regulatory T cells, or memory T cells. T cells need all four signals to complete differentiation into the full array of effector cells[8-11].

In addition to this role in T cell activation, the CD40-CD40L interaction is also essential for T-cell-dependent B-cell activation. Moreover, CD40 participates in several other immune processes, including T-lymphocyte-dependent antibody class switching, antibody affinity maturation, development of memory B cells, and formation of the germinal centers[12-16]. Thus, this costimulatory protein plays a central role in initiating an adaptive immune response.

Recent studies have shown that CD40 agonists can be used to induce an enhanced immune response. These agonists, which include both anti-CD40 monoclonal antibodies (mAbs) and soluble CD40L, mimic the outcome of the naturally occurring CD40-CD40L interaction. In previous work, our group demonstrated the ability of a novel anti-chicken CD40 mAb to activate a chicken HD11 macrophage cell line. When this CD40 agonist was conjugated with an antigenic peptide and administered by several routes, it induced a robust immune response and several desired effects, including immunoglobulin class switching[17-19]. These results suggest that this mAb would be useful as a vaccine adjuvant. However, the high cost and the difficulty of producing mAb make it impractical to commercialize this antibody for use in industries with tight profit margins, such as the poultry industry. Further, mAbs are highly immunogenic and have the potential to interfere with vaccine action. Thus, there is a need in the art for alternative CD40-stimulating biomolecules with low-immunogenicity for use as vaccine adjuvants.

SUMMARY

The present invention provides immunostimulatory nucleic acids that comprise a protein-binding sequence having at least 80% identity to any one of SEQ ID NOs: 1-8.

In another aspect, the present invention provides immunostimulatory nucleic acids comprising a plurality of protein-binding units, wherein each of the protein-binding units comprise a first protein-binding sequence, a second protein-binding sequence, and a spacer sequence therebetween, and wherein the second protein-binding sequence is a different sequence than the first protein-binding sequence.

In yet another aspect, the present invention provides methods of binding an immune response signaling protein. The methods involve contacting the protein with the immunostimulatory nucleic acids disclosed herein.

The present invention also provides templates for producing a plurality of protein-binding units. The templates comprise in order from 5' to 3': (i) a 3' end of a primer-binding sequence, (ii) a complement of a second protein-binding sequence, (iii) a complement of a spacer sequence, (iv) a complement of a first protein-binding sequence, and (v) a 5' end of a primer-binding sequence. Importantly, the 5' end of the primer-binding sequence and the 3' end of the primer-binding sequence form a primer-binding site when the template is circularized.

In another aspect, the present invention provides methods of producing an immunostimulatory nucleic acid. The methods comprise (a) providing a template disclosed herein, (b) circularizing the template, and (c) amplifying the circularized template to produce the immunostimulatory nucleic acid.

In yet another aspect, the present invention provides methods of producing an immunostimulatory complex. The methods comprise (a) amplifying the templates disclosed herein to produce an immunostimulatory nucleic acid, (b) tagging the immunostimulatory nucleic acid with a binding tag, and (c) linking the immunostimulatory nucleic acid to an antigen.

In still another aspect, the present invention provides immunostimulatory complexes comprising an adjuvant and an antigen, wherein the adjuvant is an immunostimulatory nucleic acid disclosed herein, and wherein the adjuvant and the antigen are linked.

In a final aspect, the present invention provides methods for enhancing an immune response in a subject. The methods involve administering an effective amount of the immunostimulatory complexes disclosed herein to the subject.

BRIEF DESCRIPTION OF THE DRAWINGS

FIG. 1C shows a prediction of the secondary structure of the selected DNA aptamer candidate SEQ ID NO: 25. The prediction was performed using the UNAFold software found at the Integrated DNA Technologies website.

μg/mL (x-axis) in triplicates. Nitric oxide liberation was measured using a Griess assay. Results were compared to those generated with anti-chicken CD40 mAb, which is known to affect this cell line (Chen et al., 2010), and to negative control RCA (NC-RCA; two sequences randomly picked from the library that were not enriched in the Illumina sequencing results). FIG. 5A shows the results from cells treated with RCA I-IV as compared to cells treated with NC-RCA. FIG. 5B shows the results for RCA-II as compared to NC-RCA and anti-CD40 mAb. Multiple way ANOVA and Tukey's Honest Significant Difference test (HSD) were applied to detect significant differences between the treatments. Different uppercase letters at each concentration represent a difference at p<0.0001 within concentrations.

FIG. 7A shows a cartoon model of chCD40$_{ED}$ with the amino acid sequence depicted above (SEQ ID NO: 9). In FIG. 7B, the three putative aptamer-protein interaction sites (region 1 (bold), region 2 (bold, underlined), and region 3 (bold, double underlined)) identified by MALD-TOF-MS are depicted as space filling models with the amino acid sequence of the protein shown above (SEQ ID NO: 2). Note: Region 1 is the long "flabby" peptide sequence where CD40L binds to the protein. FIG. 7C shows a top view of a 3D model of chCD40$_{ED}$ in a trimer configuration (gray mesh model) with the potential aptamer binding sites shown as space-filling models (R1, R2 and R3). These sites are located in the inner portion of the receptor, resembling the actual ligand binding sites (see below). FIG. 7D shows a model of the human CD40-CD40L interaction, highlighting the anti-CD40-mAb Fc interaction regions. Agonistic activity of the mAb increases proximally over the receptor, whereas antagonistic activity of the anti-CD40 mAb increases distally. FIG. 7A-7C were produced using PyMOL 2.2 software (W. L. Delano, Schrodinger, Inc). FIG. 7D was obtained from Yu, X. et al., 2018.

FIG. 9A shows the results grouped by days after immunization. FIG. 9B shows the results grouped by treatment group.

DETAILED DESCRIPTION

Figure 1A:
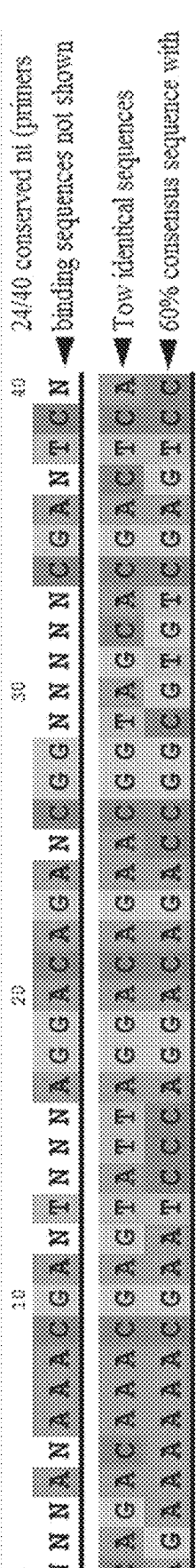
FIG. 1A shows the sequences of two aptamers determined by Sanger sequencing. The aptamers were sequenced after six rounds of SELEX selection against the chCD40$_{ED}$ protein. The top sequence (SEQ ID NO: 23) shows the consensus of the middle sequence (SEQ ID NO: 24) and the bottom sequence (SEQ ID NO: 25). Note: These sequences are the randomized portion of SEQ ID NO: 1 and SEQ ID NO: 2, respectively. (SEQ ID NOs: 1-2 further comprise primer-binding sequences.)

Disclosed herein are immunostimulatory nucleic acids, immunostimularoty complexes, methods of making, and methods of using the same for enhancing an immune response. The flexibility provided by these compositions allow for easier introduction into biological systems. The Examples demonstrate that synthetic immunostimulatory nucleic acids and immunostimularoty complexes are beneficial when loaded with appropriate antigen to act as an adjuvant. Use of these compositions results in elevated antibody titer as early as seven days post immunization and the elevated antibody titer remained high after the initial induction. The action of these complex proves that these compositions and methods have high potency and efficacy in enhancing an immune response.

The present invention provides immunostimulatory nucleic acids that comprise at least one "protein-binding sequence". As used herein, the phrase "protein-binding sequence" refers to a nucleic acid sequence that has affinity for a specific target protein. In the Examples, we describe the production of immunostimulatory nucleic acids selected against CD40 protein and demonstrate that these aptamers can be used as effective adjuvants in vivo.

The nucleic acids of the present invention are preferably single-stranded nucleic acid molecules that can fold into complex three-dimensional structures. The nucleic acids bind to target proteins with high specificity such that they discriminate against molecules closely related to the target molecule. Artificially produced nucleic acids with these properties are commonly referred to as "aptamers". Aptamers bind to their target ligands with high affinity and specificity, sometimes exceeding those of antibodies to the same target molecule. Further, aptamers may be produced in vitro, and do not require animals or cells for production as antibodies do. Other beneficial characteristics of aptamers include thermostability, chemical resistance, reproducibility, and low immunogenicity.

In some embodiments, the nucleic acids comprise a sequence having at least 80% identity to any one of SEQ ID NOs: 1-8. The phrases "% sequence identity," "percent identity," or "% identity" refer to the percentage of nucleotide matches between at least two nucleic acid sequences aligned using a standardized algorithm. The phrase "at least 80% identity" also includes sequences having at least 85%, 90%, 95%, 96%, 97%, 98%, 99% or more percent identity. Methods of nucleic acid sequence alignment are well known. A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known nucleic acid sequence with other nucleic acid sequences from a variety of databases. Nucleic acid sequence identity may be measured over the length of an entire defined nucleic acid sequence, for example, as defined by a particular SEQ ID number, or may be measured over a shorter length, for example, over the length of a fragment taken from a larger, defined nucleic acid sequence, for instance, a fragment of at least 5, at least 10, at least 15, at least 20, or more contiguous residues. Such lengths are exemplary only, and it is understood that any fragment length supported by the sequences shown herein, in the tables, figures or Sequence Listing, may be used to describe a length over which percentage identity may be measured.

In some embodiments, the immunostimulatory nucleic acids comprise a plurality of "protein-binding units", wherein each of the protein-binding units comprise a first protein-binding sequence, a second protein-binding sequence, and a spacer sequence therebetween, and wherein the second protein-binding sequence is suitably a different sequence than the first protein-binding sequence. The protein-binding units may comprise two sequences that each individually target a different protein or that target different portions of the same protein.

The spacer sequence is a series of nucleotides used to separate the protein-binding sequences within the immunostimulatory nucleic acids. The spacer sequence may be any series of nucleotides that does not disrupt the interaction of the protein-binding sequences with the target protein(s). The spacer sequence may be derived from a naturally occurring region of non-coding DNA found between genes, such as the spacer DNA found between the many tandemly repeated copies of the ribosomal RNA genes. In some embodiments, the spacer sequence is greater than or equal to 10 nucleotides in length and is less than or equal to 20 nucleotides in length, including any length between 10 and 20 nucleotides. The immunostimulatory nucleic acids of the present invention may further comprise a complementary sequence (referred to as a "spacer complementary" sequence) that is partially or completely hybridized to the spacer sequence. As used herein, the term "hybridize" refers to a process in which a one single-stranded nucleic acid anneals to another single-stranded nucleic acid based on the well-understood principle of sequence complementarity. In some embodiments, the strands are partially hybridized if at least 80%, 85%, 90%, 95%, or more of the nucleotides are paired to their complement. In the Examples, a spacer complementary sequence is annealed to the immunostimulatory nucleic acids to create rigid regions between the repeated aptamer sequences. The spacer regions used in the Examples were 15 nucleotides long. In the RCA template sequences shown in Table 1, the spacer regions are indicated by a double underline. Note: These spacer sequences are the reverse complement of those included in the RCA product.

The immunostimulatory nucleic acids described in the Examples are combinations of two separate CD40 binding aptamers: RCA I comprises repeating units of SEQ ID NO: 1 and SEQ ID NO: 2 separated by a spacer sequence; RCA II, which demonstrated the best adjuvant function, comprises repeating units of SEQ ID NO: 3 and SEQ ID NO: 4 separated by a spacer sequence; RCA III comprises repeating units of SEQ ID NO: 5 and SEQ ID NO: 6 separated by a spacer sequence; and RCA IV comprises repeating units of SEQ ID NO: 7 and SEQ ID NO: 8 separated by a spacer sequence. However, the eight binding sequences disclosed herein may be used in any combination.

The immunostimulatory nucleic acids of the present invention may comprise ribonucleic acid (RNA), deoxyribonucleic acid (DNA), a mixture of RNA and DNA, or analogs thereof. Analogs are structurally similar to the naturally occurring residues in RNA and DNA, and can be incorporated (e.g., chemically) into an oligonucleotide or nucleic acid by formation of a phosphodiester bond or equivalent with one or two residues. A nucleoside analog differs from a nucleoside by having one or more of its hydroxyl, base or sugar groups altered. In some embodiments, the nucleic acids are DNA.

The immunostimulatory nucleic acids of the present invention may further comprise other chemical modifications. Exemplary chemical modifications include a chemical substitution at a sugar position, a chemical substitution at a phosphate position, and a chemical substitution at a base position of the nucleic acid. Other chemical modifications include incorporation of a modified nucleotide, 3' capping, conjugation to a non-immunogenic compound, conjugation to a lipophilic compound, and incorporation of phosphorothioate into the phosphate backbone. In some embodiments of the present invention, the immunostimulatory nucleic acids include a binding tag. Suitable binding tags include, without limitation, chitin binding protein (CBP), maltose binding protein (MBP), Strep-tag, glutathione-S-transferase (GST), poly(His) tag, FLAG-tag, GFP, V5-tag, Myc-tag, HA-tag, Spot-tag, T7-tag and NE-tag. In certain embodiments, the binding tag is biotin.

The immunostimulatory nucleic acids may be chemically synthesized or transcribed from appropriate nucleic acid templates and modified during or after synthesis, as desired. Nucleic acids can be stored in a variety of forms, including as lyophilized powders. Nucleic acids may be chemically synthesized or generated using polymerase chain reaction (PCR), rolling circle amplification, and/or recombinant DNA technologies. Commercial suppliers such as Integrated DNA Technologies (Coralville, IA) are often employed to generate synthetic nucleic acids.

As is described in the Examples, the immunostimulatory nucleic acids may be identified from large combinatorial libraries of nucleic acids (e.g., libraries comprising $10^{14}$-$10^{15}$ molecules). Identification may be accomplished using in vitro selection or SELEX (Systematic Evolution of Ligands by Exponential Enrichment) to enrich for nucleic acids that target a specific protein or molecule (i.e., aptamers). To perform in vitro selection, nucleic acid libraries are incubated with the target molecule of interest, and unbound sequences are separated from target-bound sequences using methods such as membrane filtration, affinity columns, magnetic beads, or capillary electrophoresis. Then, the target-bound sequences are amplified by PCR (i.e., for DNA aptamers) or reverse transcription PCR (i.e., for RNA aptamers). The reaction products are used as a new aptamer sub-pool for the next round of selection. After a certain number of selection rounds, the identity of the enriched aptamers is determined by sequencing (e.g., using Sanger sequencing or newer high-throughput methods). The affinity of the candidate aptamers for the target molecule can then be tested using conventional assays known in the art. In the Examples, aptamer binding was tested using a dot blot assay.

Immune cells express "immune response signaling proteins", i.e., distinct cell surface receptors or ligands that sense and respond to environmental cues. In some embodiments of the present invention, the immunostimulatory nucleic acids target an immune response signaling protein. Thus, these nucleic acids may induce immune cell signaling upon binding the target protein. In the Examples, the nucleic acids were produced to target CD40. As is detailed in the Background section, CD40 is a costimulatory protein that is found primarily on antigen presenting cells and induces their activation. In some embodiments of the present invention, the nucleic acids induce a CD40 signaling response when bound to CD40, and this signaling response leads to activation of an immune response when it occurs in vivo.

Methods of binding an immune response signaling protein, such as CD40, are also provided by the present invention. The methods involve contacting the protein with the immunostimulatory nucleic acids of the present invention. The contacting may be performed directly or indirectly and may be in vivo, in vitro, or ex vivo. Contacting encompasses administration of the immunostimulatory nucleic acids to a cell, tissue, mammal, patient, or human. The nucleic acids may be introduced or administered by means of any appropriate procedures and/or routes of administration.

In another aspect, the present invention provides templates for producing a plurality of protein-binding units. From 5' to 3', the templates comprise (i) a 3' end of a primer-binding sequence, (ii) a reverse complement of a second protein-binding sequence, (iii) a reverse complement of a spacer sequence, (iv) a reverse complement of a first protein-binding sequence, and (v) a 5' end of a primer-binding sequence. Importantly, the templates are designed such that the 5' end of the primer-binding sequence and the 3' end of the primer-binding sequence form a primer-binding site when the template is circularized. In other words, the templates comprise the reverse complement of a protein-binding unit flanked on each end with a portion of a primer-binding site. As used herein, a "primer-binding site" refers to a region of a nucleotide sequence where an RNA or single-stranded DNA primer binds to start replication, and the term "primer-binding sequence" is used to refer to a portion of the primer-binding site. The templates may be used to produce immunostimulatory nucleic acids comprising any of the protein-binding units disclosed herein. For instance, the protein-binding units may comprise at least one protein-binding sequence having at least 80% identity to any one of SEQ ID NOs: 1-8 and/or having an affinity for an immune response signaling protein. The templates of the present invention may also include additional modifications. For example, in some embodiments the template is phosphorylated to enable its circularization by a ligation reaction.

In another aspect, the present invention provides methods of producing an immunostimulatory nucleic acid. These methods involve (a) providing a template disclosed herein, (b) circularizing the template, and (c) amplifying the circularized template to produce the immunostimulatory nucleic acid. Template amplification may be performed using rolling circle amplification (RCA). RCA is an isothermal process that generates a product consisting of tandemly linked copies of a sequence that is complementary to the template (Mohsen and Kool, 2016). In the methods of the present invention, a circularized template, comprising a sequence that is complementary to the selected protein-binding unit, is used to synthesize RCA products that contain thousands of tandem repeats of the protein-binding unit. Notably, these repeats mimic naturally occurring receptor-ligand oligomerization. One advantage of this design is that the two extremities of the resulting immunostimulatory nucleic acids serve as buffer regions that protect the internal region from nuclease enzymes, improving stability. The immunostimulatory nucleic acids described in the Examples were designed to serve as adjuvants (defined below), and the inventors have demonstrated that the stability of these nucleic acids allows them to be used effectively as adjuvants, even when they are administered more than once.

The methods of the present invention may additionally involve selecting the protein-binding sequences to include in the template. In some embodiments, the methods involve selecting protein-binding sequences that have an affinity for an immune response signaling protein. In the Examples, protein-binding sequences were selected from sequences that were shown to have an affinity for CD40 using SELEX (described above), and the reverse complements of these sequences were included in the template.

The methods may additionally involve phosphorylating the template (i.e., to facilitate ligation), annealing a primer to the template (i.e., to circularize it), performing a ligation reaction on the template, or any combination thereof. The term "ligation" refers to a process by which two ends of DNA or RNA are linked. Ligation is accomplished using an enzyme called a ligase. Any suitable ligase known in the art may be utilized with the present methods.

Additionally, these methods may further comprise partially or completely hybridizing a complementary sequence to the spacer sequence of the immunostimulatory nucleic acid to create rigid regions between the repetitive aptamer sequences. The methods may also further comprise tagging the immunostimulatory nucleic acid with a binding tag (e.g., biotin).

Methods of producing an immunostimulatory complex are also provided. The methods involve (a) amplifying the templates of the present invention to produce an immunostimulatory nucleic acid, (b) tagging the immunostimulatory nucleic acid with a binding tag, and (c) linking the immunostimulatory nucleic acid to an antigen, thereby producing an immunostimulatory complex.

The term "antigen" refers to any substance that induces an immune response in a body. The antigen included in the immunostimulatory complexes of the present invention may comprise the entirety or a portion of a protein, polypeptide, carbohydrate, or vaccine. The antigen may be a bacterial antigen, viral antigen, protozoan antigen, or fungal antigen. In some embodiments, the antigen is a peptide comprising the ectodomain of matrix protein 2 (M2e), a protein that is highly conserved among all influenza virus strains. However, the antigen may be specific to any pathogen including, without limitation, influenza virus, severe acute respiratory syndrome virus (SARS-CoV or SARS-CoV-2), Middle East respiratory syndrome viruse (MERS-CoV), *Salmonella, Clostridium, Campylobacter, Escherichia, Shigella, Helicobacter, Vibrio, Plesiomonas, Edwardia, Clostridia, Klebsiella, Staphylococcus, Streptococcus, Aeromonas*, Foot and Mouth virus, porcine epidemic diarrhea virus (PEDv), and Porcine reproductive, respiratory syndrome virus (PRRSV), *Eimeria, Toxoplasma* and malaria. For example, the antigens or epitopes identified in U.S. Pat. No. 8,604,198, International Publication Nos. WO2009/059018, WO2009/059298, WO2011/091255, WO2011/156619, WO2014070709, WO 2014/127185 or WO 2014/152508 may be used. Antigenic polypeptides may include any one or more of those provided in SEQ ID NOs: 26-80 and include polypeptides identical to, or at least 99% identical, at least 98% identical, at least 95% identical, at least 90% identical, at least 85% identical, or at least 80% identical to those provided in SEQ ID NOs: 26-80. Antigens may be produced or obtained by standard methods known in the art, and may include chemical modifications. For instance, antigens may be commercially produced (i.e., as synthetic peptides), as described in the Examples. Advantageously, the antigen used with the present invention may be highly conserved (e.g., M2e for Influenza) such that it is effective against a broad range of pathogens. Those skilled in the art will also recognize that the antigenic polypeptides may also include additional amino acids or may be linked to each other to form a sort of fusion protein comprising more than one antigenic polypeptide. The linker amino acids may be any amino acids but serine and glycine are most commonly used. The linker may be as short as one or two amino acids, but may be 4, 5, 6, 8, 10, 12, 14, 15 or more amino acids long.

The immunostimulatory complexes disclosed herein may be used as vaccines or as adjuvants for use in combination with established vaccines. As used herein, the term "adjuvant" refers to a substance that can enhance an immune response to an antigen. Adjuvants are commonly added to vaccines to enhance the immunogenicity of the antigen used in the vaccine. Because the immunostimulatory nucleic acids of the present invention are target-specific rather than antigen-specific, they could feasibly be used with vaccines against nearly any pathogen. As "universal adjuvants," these nucleic acids may be of particular value for use with a vaccine against newly arising pathogens and pathogens that are prone to genetic variation, as their use does not require precise identification of target antigens.

Within the immunostimulatory complexes of the present inveniton, the immunostimulatory nucleic acid may be linked to the antigen using any suitable protein-nucleic acid crosslinking agent or bioconjugation reaction. Cross-linking agents include, without limitation, formaldehyde, disuccinimidyl glutarate, UV light, psoralens and their derivatives (e.g., aminomethyltrioxsalen, glutaraldehyde), ethylene glycol bis[succinimidylsuccinate], bissulfosuccinimidyl suberate, 1-Ethyl-3-[3-dimethylaminopropyl]carbodiimide (EDC) bis[sulfosuccinimidyl] suberate (BS3) and other compounds known to those skilled in the art, including those described in the Thermo Scientific Pierce Crosslinking Technical Handbook, Thermo Scientific (2009). Common linkages for site-specific bioconjugation rely on cysteine, lysine, tryptophan or tyrosine residues, while newer methods target non-natural functional groups (e.g., olefins). However, many other bioconjugation methods are known to those skilled in the art, including those described in the Thermo Fisher Scientific Bioconjugation Technical Handbook, Thermo Fisher Scientific (2018). In some embodiments, the immunostimulatory nucleic acids and antigens are each labeled with a biotin binding tag and streptavidin is used as a linker. In the Examples, the immunostimulatory complex comprises two biotinylated aptamer molecules and two biotinylated M2e peptides conjugated by one streptavidin molecule.

The present invention also provides immunostimulatory complexes including, but not limited to, those produced by the methods described above. The immunostimulatory complexes comprise an adjuvant (i.e., an immunostimulatory nucleic acid disclosed herein) linked to an antigen. In some embodiments, the antigen is derived from the Influenza M2e protein. For instance, the antigen may comprise an amino acid sequence having at least 80% identity to SEQ ID NO: 22.

The present invention also provides methods for enhancing an immune response in a subject. The methods involve administering an effective amount of an immunostimulatory complex of the present invention to the subject. As used herein, an "effective amount" or a "therapeutically effective amount" refers to the amount of the adjuvant or vaccine that, when administered to a subject for treating a state, disorder or condition is sufficient to effect a treatment (i.e., an enhanced immune response). The effective amount will vary depending on the exact composition and its formulation, the disease or pathogen being targeted by the vaccine and its severity and the age, weight, physical condition and responsiveness of the subject to be treated.

The immunostimulatory complexes may be administered with a pharmaceutically acceptable carrier. A pharmaceutically acceptable carrier is any carrier suitable for in vivo administration. Suitable pharmaceutically acceptable carriers include, but are not limited to, water, buffered solutions, glucose solutions, oil-based solutions, or bacterial culture fluids. A pharmaceutically acceptable carrier may further comprise excipients such as stabilizers, preservatives, diluents, emulsifiers and lubricants. Suitable stabilizers include carbohydrates (e.g., sorbitol, mannitol, starch, sucrose, glucose, or dextran), proteins (e.g., albumin or casein), protein-containing agents (e.g., bovine serum or skimmed milk), and buffers (e.g., phosphate buffer).

The immunostimulatory complexes may be administered by any means known in the art, including by, e.g., mucosal, oral, topical, intranasal, intraperitoneal, parenteral, intravenous, intramuscular, subcutaneous, intrathecal, transcutaneous, nasopharyngeal, cloacal, ocular, or transmucosal routes. To this end, the immunostimulatory complexes may be formulated as an ingestible, injectable, topical, or suppository formulation. The complexes may also be delivered by a liposomal or time-release vehicle. In some embodiments, the immunostimulatory complex is administered by a subcutaneous route.

The subject treated by the present methods may be any vertebrate including, without limitation, a chicken, a turkey, a cow, a pig, a fish, a goat, a sheep, a dog, a cat, a human, or another animal. In the Examples, a CD40-targeting immunostimulatory complex is used to treat chickens. However, the methods would also be useful for the vaccination of any meat producing animals. Suitably, the CD40 aptamers used with the methods are selected based on their affinity for a host-specific CD40 protein.

The immunostimulatory complexes disclosed herein are designed to increase the magnitude of a systemic immune response to a vaccine or to increase the speed at which an immune response to a vaccine develops. The immune response may comprise a T cell or B cell response. In some embodiments, the immune response is an IgG response. Suitably, the immune response is measurable within seven days.

The specific dosage of immunostimulatory complexes administered in any given case will be adjusted in accordance with the compositions being administered, the condition of the subject, and other relevant medical factors that may alter the activity of the compositions or the response of the subject. As is known in the art, the dosage used for a particular subject may need to be adjusted based on factors such as age, body weight, general state of health, diet, the timing and mode of administration, the rate of excretion, and medicaments used in combination. Dosages for a given patient can be determined using conventional methods, e.g., by comparing the activity of the compositions to that of a known agent (e.g., a similar vaccine) using an appropriate pharmacological or prophylactic protocol. Suitable effective dosage amounts of the compositions may be determined by those of skill in the art, but typically range from about 1 microgram to about 1,000 micrograms per kilogram of body weight or per dose, although they are typically about 10 to 100 micrograms or less per kilogram of body weight or per dose. Commonly, a single dose is followed by a "boost", which may comprise the same or a distinct composition, at least two weeks after the first administration. The boost may be administered, for example, 2-6, 2-4, or 2-3 weeks after the initial dose.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

In Example 1, the inventors describe the production of the immunostimulatory nucleic acids of the present invention. First, DNA aptamers were selected using systemic evolution of ligands by exponential enrichment (SELEX)[20, 21]. Then, the aptamer candidates were paired and used to produce rolling circle amplification (RCA) products[27-29]. These RCA products, termed aptamer-based RCA (or aptamer RCA), consist of thousands of tandemly repeated sequences of the selected aptamers, as to mimic naturally occurring receptor-ligand binding. The inventors demonstrated that all four aptamer RCAs have the ability to activate chicken macrophage HD11 cells.

In Example 2, the inventors demonstrate that the aptamer RCAs can serve as vaccine adjuvants in chickens. Aptamer RCA II, which showed the strongest macrophage stimulation, was then conjugated with a hapten to form an adjuvant-antigen immunostimulatory complex. The inventors used the influenza virus M2e peptide as the antigen in the complex. Notably, the M2e peptide has low immunogenicity,[54] and was previously used by the inventors to evaluate a monoclonal antibody (mAb)-adjuvant immunostimulatory complex. The immunostimulatory complex was subcutaneously injected into broiler chickens at two doses (25 µg/bird and 50 µg/bird of aptamer RCA II). At the higher dose, the immunostimulatory complex induced a robust immune response as early as 7 days post-injection, and both doses induced a robust response after 21 days. These data suggest that the aptamer RCAs disclosed herein may be broadly useful as universal adjuvants that can be conjugated with any antigen.

Example 1—In Vitro Selection of CD40 Aptamers

Materials and Methods:

Preparation of the target protein: The chicken CD40 extracellular domain (chCD40$_{ED}$) was used for aptamer selection. The chCD40$_{ED}$ protein was recombinantly expressed in HEK293 Freestyle cells in a protein-free medium and was purified by Antagene (Santa Clara, CA) at a concentration of According to a mass spectrometry analysis, the protein had a molecular weight around 25,712 Da. The protein stock was diluted with sterile 1× phosphate buffer saline (1×PBS, w/v) to the concentration of 15 µg/L and was stored at −80° C.

Single-stranded DATA library and primers: A randomized single-stranded DNA (ssDNA) library and forward and reverse primers were purchased from Integrated DNA Technologies (IDT, Coralville, Iowa, USA). The ssDNA library comprised randomized sequences that were 40 nt in length, flanked by 20 nucleotide (nt) forward and reverse primer binding sites. The randomized region consisted of bases (A, T, G and C) that were randomly incorporated in equal ratio at each position. The reverse primer was phosphorylated at the 5' end to facilitate digestion of double-stranded DNA by lambda exonuclease in the later steps of the enrichment cycles. The library had a theoretical diversity of $1 \times 10^{24}$ random sequences (Table 1).

In vitro aptamer selection: Aptamer selection was performed using a procedure that has been described elsewhere[20, 21]. For the first round of selection, 35 µl of the ssDNA library (1 µg/µl) was denatured at 95° C. for 10 min, cooled down to 4° C. for 5 min, and incubated at room temperature (RT) for 10 min. The SELEX procedure was performed as previously described[46, 47]. To gradually increase the stringency of selection, each subsequent round of SELEX used only 75% of the volume of the target protein that was used in the previous round.

PCR enrichment and dsDNA digestion into ssDNA: After each round of SELEX, the resulting ssDNA was amplified via 25 cycles of polymerase chain reaction (PCR). PCR was conducted using G2 Hot Start Green Master Mix (Promega). The reaction mix consisted of 1 µl (10 µM) of the DNA library, 2 µl of forward and phosphorylated reverse primers (4 µM), and 12.5 µl of 2× master mix (pH 8.5). Nuclease-free water was added to adjust the final reaction volume to 25 µl. Each PCR thermal cycle consisted of: denaturation at 95° C. for 5 min, followed by 25 cycles of 95° C. for 30 sec, 56° C. for 15 sec, and 72° C. for 15 sec, followed by a final extension at 72° C. for 5 min. The PCR products were detected on a 1% agarose gel stained with SYBR Safe dye (Thermo Fisher Scientific, USA). The resulting double-stranded DNA (dsDNA) was digested with λ exonuclease (Cat #M0262S, NEB, USA), which converted the dsDNA into ssDNA for use in the next round (Table 1). The digestion reaction was performed as instructed by the manufacturer.

Sanger sequencing: After six rounds of selection, the PCR product was cloned and sequenced using Sanger sequencing. The cloning process utilized the pGEM-T and pGEM-T easy vector systems (Cat #A1360, Promega). As instructed by the manufacturer, the PCR product was inserted into the vector in ligation buffer. The insert-containing plasmid was transformed into electrocompetent TOP 10 E. coli (Invitrogen, Carlsbad, CA, USA) by pulsed, high-voltage electroporation (1750V for 5 msec using the ECM™ 830 electroporation generator, Fisher Scientific). After transformation, 500 µL of SOC media (Invitrogen, Carlsbad, CA) was added and the bacteria were incubated for 2 hrs at 37° C. with shaking. Medium containing the bacteria was streaked onto Luria-Bertani medium plates containing ampicillin (100 µl/plate, Cat #R110846, ThermoFisher Scientific), IPTG (Calbiochem, San Diego, CA), and 5-bromo-4-chloro-3-indolyl-β-D-galactoside (X-Gal). After overnight incubation, 15 white colonies were harvested. One extra blue colony was included as a positive control for the assay. The selected colonies were lysed and DNA was purified using QIAprep Miniprep kit (Qiagen, Hilden, Germany) and submitted for Sanger sequencing (Eurofins, Louisville, KY, USA).

Illumina sequencing: Samples from SELEX rounds 1, 6, 8 and 10 were prepared for Illumina sequencing. The ssDNA from each round was barcode-tagged and amplified by PCR using Illumina sequencing primers (Table 2). Twenty-five PCR cycles were applied using KOD hot start DNA polymerase and buffer (Cat #71086-3, Sigma-Aldrich, CA, USA). All PCR products were submitted for sequencing at the University of Wisconsin Biotechnology Center (UWBC, WI, USA). High throughput Illumina sequencing was performed as previously described[46]. The resulting sequencing reads were analyzed using free software, Galaxy Bioinformatics and FastQC version 0.11.5[49-51].

Illumina sequencing produced ~16 million total reads. About 5% of the total reads were removed due to their insufficient length or quality. For the most abundant aptamers, the free energy change (ΔG[kcal·mole$^{-1}$]) of the aptamer's three-dimensional structure was analyzed using the online OligoAnalyzer 3.1 Tool (Integrated DNA technologies), and the most reliable aptamers were subjected to further testing.

Dot blot hybridization assay: A dot blot assay was used to determine the affinity of the candidate aptamers to the target protein, as described elsewhere[46, 47]. The candidate aptamers were ordered from a commercial supplier (IDT, Coralville, Iowa, USA) as 5' biotinylated DNA. Immune-Blot PVDF membrane (0.2 μm, Cat #162-0174, Bio Rad laboratories, Ca.) was cut into 8 strips of 6 cm² (1 cm²/trt) and 10 μl (15 μg/mL) of the target protein was applied to the center of 5 of the test squares. After drying, the stripes were blocked with KPL blocking buffer for 30 min and washed (3×) with 1×KPL washing buffer (Cat #50-63-00, KPL, Gaithersburg, MD). Aptamers were then applied to the center of the test squares at concentrations of 12, 25 and 50 μM. The membranes were air dried and washed three times with 1×KPL washing buffer. Streptavidin-conjugated alkaline phosphatase (Cat #475-300, KPL, Gaithersburg, MD, diluted 1:500) was applied to the membrane for 30 min and another round of washing was performed. Finally, color was developed by adding 5-bromo-4-chloro-3-indoxyl-phosphate and nitro blue tetrazolium (BCIP/NBT) substrate (Cat #50-81-07, KPL, Gaithersburg, MD, USA). The reaction was stopped by washing the membrane thoroughly with tap water.

Figure 2:
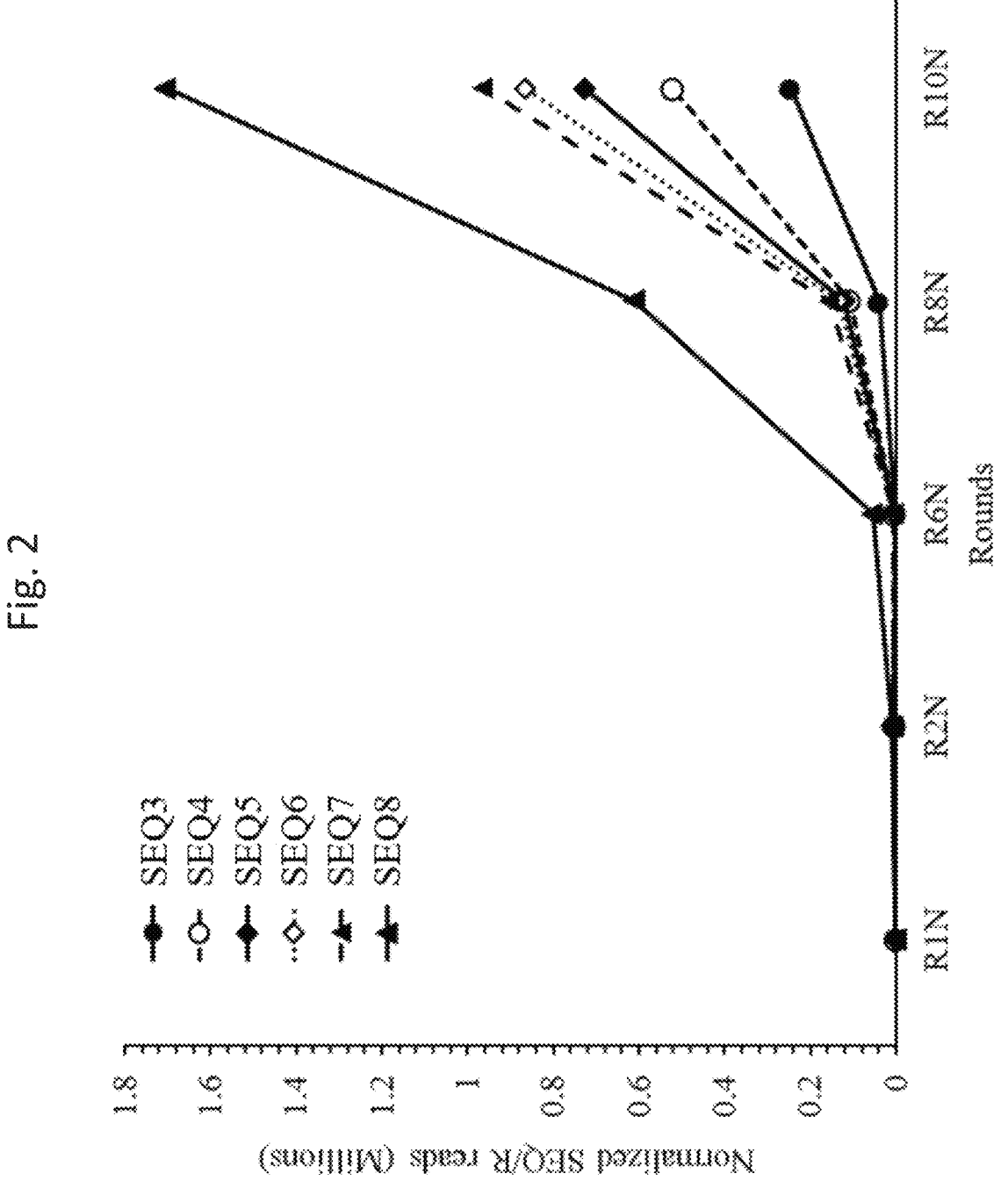
FIG. 2 shows a visual representation of the frequency of six highly enriched aptamer sequences over 10 rounds of SELEX (R1-R10). The frequency was based on the normalized number of Illumina sequencing reads, determined using the following calculation: (frequency of aptamer sequence X 100/total no. of reads)/(% the aptamer sequence in the first round of SELEX selection as this hypothetically represents expression of all sequences). Round 1 is the reference round in which all sequences are expected to be present in equal amount in theory.

Rolling circle amplification: To improve the ability of the aptamers to remain bound to the CD40 receptor in vivo, the aptamers that that bound to the target protein in the dot blot assay were further subjected to rolling circle amplification (RCA). Eight candidate aptamers were grouped into four pairs, forming four complementary templates for RCA. The two aptamers that were most highly enriched (according to the Illumina sequencing) were paired to form the first template. The second template included the second two most highly enriched aptamers, and so forth (FIG. 2, Table 2). The 5' end of all templates was phosphorylated to facilitate ligation. The RCA primers were designed to be complementary to the upstream and the downstream extremities of the template. Finally, a spacer complementary sequence was added between repeats to provide rigid regions among the repetitive aptamer sequences. To perform the RCA procedure, 15-20 pmol of primer (equivalent to 132 ng/μl) were allowed to anneal to the primer binding site on the template (1-2 pmol, equivalent to 129 ng/μl). Binding of the primer to each end of the template forms a circularized template containing a nick. The primer-template mixture was heated to 95° C. for 10 min, heated to 56° C. for 5 min, and then cooled to RT in 50 μl TE buffer. To ligate the nicked template, a ligation assay was perfumed using T4 DNA ligase (Cat #M0202S, NEB, USA) and following the reaction conditions recommended by the manufacturer.

φ29 DNA polymerase (Cat #M0269L, NEB, USA) was used for the polymerization step. Polymerization reactions were performed using manufacturer recommended conditions, except that the reaction was held for 16 hr and then heat-inactivated at 65° C. for 10 min. After each enzymatic treatment, the DNA was purified by ethanol precipitation. After the spacer complementary sequence was added, the quality and quantity of the RCA products were evaluated using a microplate reader (BioTeck). Spacer complementary sequence was mixed with the RCA products (RCA-p) at a molecular ratio of 2:1, and the mixture was held for 10 min at 95° C., for 5 min at 50° C., and was then cooled on ice to allow annealing.

Measuring activation of chicken HD11 macrophage cell line: The chicken HD11 macrophage cell line was propagated on 96-well plate at 37° C. in a humidified atmosphere having 5% $CO_2$ in Dulbecco's modification of eagle's medium (DMEM; Mediatech, Manassas, VA). The medium was enriched with 8% fetal bovine serum (Atlanta Biologicals, Lawrenceville, GA) and 5% chicken serum (Sigma, St. Louis, MO). All treatments were applied when the cells reached 80% confluence. After the treatment, the plate was incubated at the same conditions for an extra four hours. After incubation, the contents of every well were collected and centrifuged, and then the supernatant was subjected to a Griess assay to detect the nitric oxide liberation from the macrophages in the medium. All cell line work was carried out in Dr. Berghman's laboratory at Texas A&M University.

MALDI-TOF-MS and LC-MS mass-spectrometry: Protein and individual ssDNA aptamers were subjected to matrix-assisted laser desorption ionization time of flight mass spectrometry (MALDI-TOF-MS) using a MALDI relex III time of flight instrument (Bruker Daltonics) to confirm the expected molecular weights. Then, to verify the protein's identity as the CD40 ligand from *Gallus gallus*, the protein was subjected to full trypsin digestion followed by liquid chromatography tandem mass spectrometry (LC-ESI-MS/MS) using an Amazon-SL (Agilent Bruker Daltonics) and standard methods described elsewhere[52]. To understand the aptamer-protein binding process, a limited proteolysis liquid chromatography electrospray ionization mass spectrometry (LC-ESI-MS) experiment was conducted using Bruker ESQUIR-LC quadrupole ion trap (QIT) without MS/MS. Intensities of the extracted ion chromatograms corresponding with each tryptic peptide were used to determine the relative inhibition for the enzyme activity toward the CD40 protein due to aptamer binding. LC-ESI-MS was operated using standard methods described elsewhere[52, 53]. One microgram of the $chCD40_{ED}$ protein was subjected to digestion with 20 ng of trypsin (Promega) containing 25 mM $NH_4HCO_3$~7.5 pH buffer at 37° C. for 1 hr, with and without the candidate aptamers. In addition, random sequence ssDNA aptamers were included as a negative control. After the incubation period, the enzyme was chemically inactivated by adding 5% FA in 60% acetonitrile (ACN), and the resulting digestion product was subjected to LC-ES-MS.

Statistical analysis: A statistical analyses of the RCA-products dose response was performed based on variance using a completely randomized design. For the nitric oxide liberation assay, Multiway Analysis of Variance (ANOVA) was performed to determine the variation between treatments, using the General Linear Models procedure of the SAS software (JMP Pro 13). For all data sets, the mean±standard deviation and p value were calculated. Tukey's Honest Significant Difference test (HSD) was used to identify significant differences among the means at p<0.001.

Results and Discussion:

In vitro selection of DNA aptamers: SELEX was used to identify aptamers with an affinity for the chicken CD40 receptor within a random ssDNA library (Table 1). This procedure was repeated for 10 enrichment cycles, as described elsewhere[20, 21]. Following each enrichment cycle, PCR was to amplify the enriched aptamers for use in the next round. To resume the SELEX process, the amplified dsDNA was then digested with λ exonuclease to produce single-stranded DNA (ssDNA) aptamers. To enrich for aptamers with increasingly higher affinity to the target protein, the molar ratio of protein to ssDNA library was decreased gradually over the 10 enrichment cycles such that the amount of target protein was reduced by 25% in each subsequent round[31].

TABLE L

DNA Library, primers, RCA templates, and complementary sequences.

| Description | DNA Sequence (5' to 3') |
|---|---|
| Library | CCG AAT TCG AAG GAC AAG AG (N) †40 TCT TT TAT GCT ACG TCC CGC (SEQ ID NO: 10) |
| Forward primer (FB) | CCG AAT TCG AAG GAC AAG AG (SEQ ID NO: 11) |
| Reverse primer (RB) | CCG AAT TCG AAG GAC AAG AG (SEQ ID NO: 12) |
| Phosphorylated RB | Phosph/CCG AATT CGA AGG ACA AGA G (SEQ ID NO: 12) |
| Illumina FP | AAT GAT ACG GCG ACC ACC GAG ATC TAC ACT CTT TCC CTA CAC GAC GCT CTT CCG ATC TNN NNN GG(BC)‡TT- (Library FP) (SEQ ID NO: 13) |
| Illumina RP | (Library RP)- TAG AGC ATA CGG CAG AAG ACG AAC (SEQ ID NO: 14) |
| RCA I template | Phosph/GCA TCT GAA C GCG GGA CGT AGC AT A AAA GAA GGA GAC CCG TAT GCA TAA CGG TGA CAC GAT CAA GTC GAA CTC TTG TCC TTC GAA TTC GG GAT CCA CCG GTA GCA GCG GGA CGT AGC ATA AAA GAG GAA AGT ATT CAA GCT TAA AAT GTA CGT GTG GAC GCG AAT CTC TTG TCC TTC GAA TTC GG GGA ACG TCT T (SEQ ID NO: 15) |
| RCA II template | Phosph/GCA TCT GAA C GCG GGA CGT AGC ATA AAA GAC GAA TTC ACT GCT CCA TTT ACA CCC CAT TAC CAA TTC CAC CTC TTG TCC TTC GAA TTC GG GAT CCA CCG GTA GCA GCG GGA CGT AGC ATA AAA GAC CTA GCC CTG CTC TTC TGA TCC CTA TTC CAT GTA GCC CTA CTC TTG TCC TTC GAA TTC GG GGA ACG TCT T* (SEQ ID NO: 16) |
| RCA III template | Phosph/GCA TCT GAA C GCG GGA CGT AGC ATA AAA GAG CGG GAC GTA GCA TAA AAG AAA CCA ACT GCA CTT ACT CTT GTC CTT CGA ATT CGG GAT CCA CCG GTA GCA GCG GGA CGT AGC ATA AAA GAG AAC AAT CGG AAC TGG TCA TCC TAG GAC GTC GTG ACT ACC TC TTG TCC TTC GAA TTC GG GGA ACG TCT T (SEQ ID NO: 17) |
| RCA IV template | Phosph/GCA TCT GAA C GCG GGA CGT AGC AT A AAA GAC AGA TGA CCA ACC ATA CTG ACT TGA CAG CAT CCC TCA TCT CTC TTG TCC TTC GAA TTC GG GAT CCA CCG GTA GCA GCG GGA CGT AGC ATA AAA GAA TGG GGG TAG TTGC AAA GGA TAG GGG TAA A AG AAA TGT TGC TCT TGT CCT TCG AAT TCG G GGA ACG TCT T (SEQ ID NO: 18) |
| NC RCA template | Phosph/GCA TCT GAA C ATG GGC AGT TCA AAC TAC GAC ATA GCA GAC CAA GGT ATA G GAT CCA CCG GTA GCA TGA TGC AGG TCC |

TABLE L-continued

DNA Library, primers, RCA templates, and complementary sequences.

| Description | DNA Sequence (5' to 3') |
|---|---|
| | TGT AAT TGG ACT GAT CAC ATA CCT AGA T GGA ACG TCT T (SEQ ID NO: 19) |
| RCA primer | GTT CAG ATG CAA GAC GTT CC (SEQ ID NO: 20) |
| Spacer-complement | GAT CCA CCG GTA GCA (SEQ ID NO: 21) |

†Random sequence
‡Barcode sequence
*Single underline represents the primer-binding site and the double underline represents the spacer region.

Figure 1B:
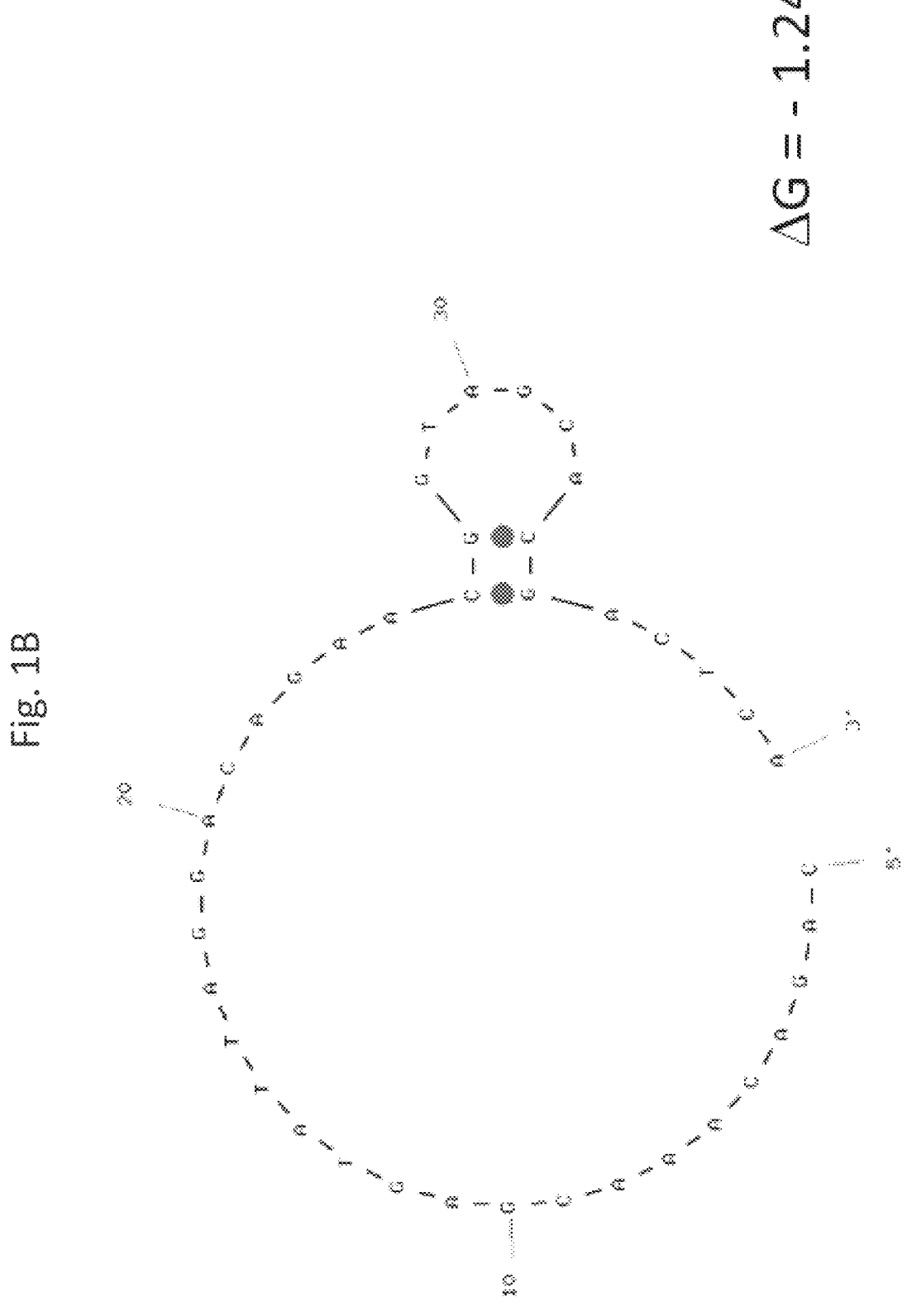
FIG. 1B shows a prediction of the secondary structure of the selected DNA aptamer candidate SEQ ID NO: 24. The prediction was performed using the UNAFold software found at the Integrated DNA Technologies web site.
Figure 1C:
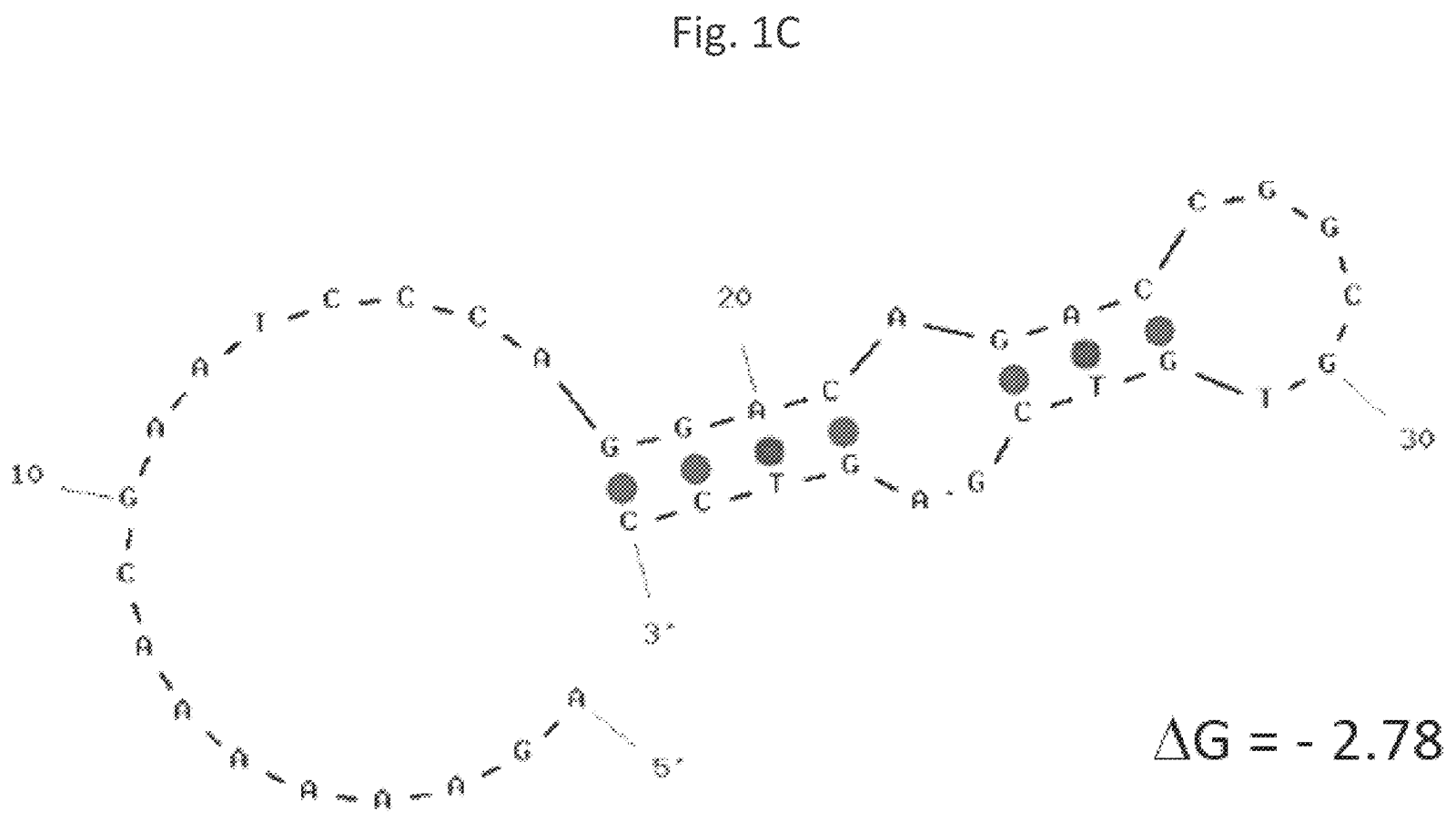

Characterization of selected aptamers by cloning and sequencing: To evaluate the selection process, DNA products from the 6th enrichment cycle were cloned and sequenced using the Sanger sequencing method[32]. One aptamer sequence (SEQ ID NO: 1) was found twice among the 15 clones sequenced, and another sequence (SEQ ID NO: 2) was determined to have 60% homology with SEQ ID NO: 1 (FIG. 1A, Table 2). These aptamer sequences were analyzed by UNAFold software (Integrated DNA Technologies) to predict the secondary structure and the free energy change (ΔG) as shown in FIG. 1B. Aptamers with very low ΔG value contain more inter-Watson-Crick base pairing, resulting in a more rigid hairpin structure with less vulnerable hydrogen bonding, which affects the aptamer-target interaction (Armstrong and Strouse, 2014).

TABLE 2

Selected aptamer sequences.

| Description | Aptamers | Aptamer RCA |
|---|---|---|
| SEQ ID NO: 1 (Sanger) | CCGAATTCGAAGGACAAGAG CAGACAAACGAGTATTAGGA CAGAACGGTAGCACGACTCA TCTTTTATGCTACGTCCCGC | RCA I |
| SEQ ID NO: 2 (Sanger) | CCGAATTCGAAGGACAAGAG AGAAAAAACGAATCCCAGGA CAGACCGGCGTGTCGAGTCC TCTTTTATGCTACGTCCCGC | |
| SEQ ID NO: 3 (Illumina) | CCGAATTCGAAGGACAAGAG GTGGAATTGGTAATGGGGTG TAAATGGAGCAGTGAATTCG TCTTTTATGCTACGTCCCGC | RCA II |
| SEQ ID NO: 4 (Illumina) | CCGAATTCGAAGGACAAGAG TAGGGCTACATGGAATAGGG ATCAGAGAGCAGGGCTAGG TCTTTTATGCTACGTCCCGC | |
| SEQ ID NO: 5 (Illumina) | CCGAATTCGAAGGACAAGAG TAAGTGCAGTTTGGGTTTTC TTTTATGCTACGTCCCGCTC TTTTATGCTACGTCCCGC | RCA III |
| SEQ ID NO: 6 (Elumina) | CCGAATTCGAAGGACAAGAG GTAAGTCACGACGTCCTAGG ATGACCAGTTCCGATTGTTC TCTTTTATGCTACGTCCCGC | |
| SEQ ID NO: 7 (Illumina) | CCGAATTCGAAGGACAAGAG AGATGAGGGATGCTGTCAAG TCAGTATGGTTGGTCATCTC | RCA IV |

TABLE 2-continued

Selected aptamer sequences.

| Descrip-tion | Aptamers | Aptamer RCA |
|---|---|---|
| | TCTTTTATGCTACGTCCCGC | |
| SEQ ID NO. 8 (Illumina) | CCGAATTCGAAGGACAAGAG CAACATTTCTTTTACCCCTA TCCTTTGCAACTACCCCCAT TCTTTTATGCTACGTCCCGC | |

High throughout Illumina sequencing: For a more comprehensive characterization of the enriched aptamers, the aptamers from the cycles 1, 2, 6, 8 and 10 were sequenced using Illumina sequencing. There were around $4 \times 10^6$ reads from each cycle. After quality filtering, about 95% of the reads were retained as high-quality sequencing reads. The analyzed data showed that there were six sequences (SEQ ID NOs: 3-8; Table 2) that were highly enriched in the aptamer pool over the SELEX enrichment cycles (Table 3). When these six sequences were plotted against each selection round, SEQ ID NO: 8 was determined to be the most abundant sequence, followed by SEQ ID NO: 7 (FIG. 2).

TABLE 3

Aptamers proportion and relative frequency at each enrichment SELEX round. The DNA from each round of SELEX was tagged with a particular barcode to ensure accurate sample assignment during data analysis. The proportion of total sequences and the relative frequency after each round has been estimated for six highly enriched aptamer sequences.

| Round | Barcode | No. of seq/ round | SEQ ID NO: | % of total seq reads | % relative fre-quency within SEQ ID NOs: 3-8 |
|---|---|---|---|---|---|
| 1 | TAGATCGC | $4.438 \times 10^6$ | 3 | 0.00006 | 2.80 |
| | | | 4 | 0.00011 | 4.67 |
| | | | 5 | 0.00155 | 64.49 |
| | | | 6 | 0.00048 | 19.62 |
| | | | 7 | 0.00018 | 7.50 |
| | | | 8 | 0.00002 | 0.95 |
| 2 | CTCTCTAT | $3.9 \times 10^6$ | 3 | 0.00231 | 9.45 |
| | | | 4 | 0.00198 | 8.09 |
| | | | 5 | 0.01408 | 57.66 |
| | | | 6 | 0.00408 | 16.70 |
| | | | 7 | 0.00139 | 5.68 |
| | | | 8 | 0.00059 | 2.43 |
| 6 | TATCCTCT | $4.368 \times 10^6$ | 3 | 0.00104 | 4.42 |
| | | | 4 | 0.00133 | 5.69 |
| | | | 5 | 0.00319 | 13.64 |
| | | | 6 | 0.00591 | 25.31 |
| | | | 7 | 0.00053 | 2.26 |
| | | | 8 | 0.01136 | 48.67 |
| 8 | AGAGTAGA | $4.038 \times 10^6$ | 3 | 0.02725 | 5.30 |
| | | | 4 | 0.07678 | 14.89 |
| | | | 5 | 0.21052 | 40.83 |
| | | | 6 | 0.05697 | 11.04 |
| | | | 7 | 0.04211 | 8.17 |
| | | | 8 | 0.10194 | 19.77 |
| 10 | ACTGCATA | $2.739 \times 10^6$ | 3 | 0.16631 | 5.29 |

TABLE 3-continued

Aptamers proportion and relative frequency at each enrichment SELEX round. The DNA from each round of SELEX was tagged with a particular barcode to ensure accurate sample assignment during data analysis. The proportion of total sequences and the relative frequency after each round has been estimated for six highly enriched aptamer sequences.

| Round | Barcode | No. of seq/ round | SEQ ID NO: | % of total seq reads | % relative fre-quency within SEQ ID NOs: 3-8 |
|---|---|---|---|---|---|
| | | | 4 | 0.31121 | 6.52 |
| | | | 5 | 3.20593 | 67.12 |
| | | | 6 | 0.66189 | 13.85 |
| | | | 7 | 0.17813 | 3.74 |
| | | | 8 | 0.16631 | 3.49 |

Figure 3:
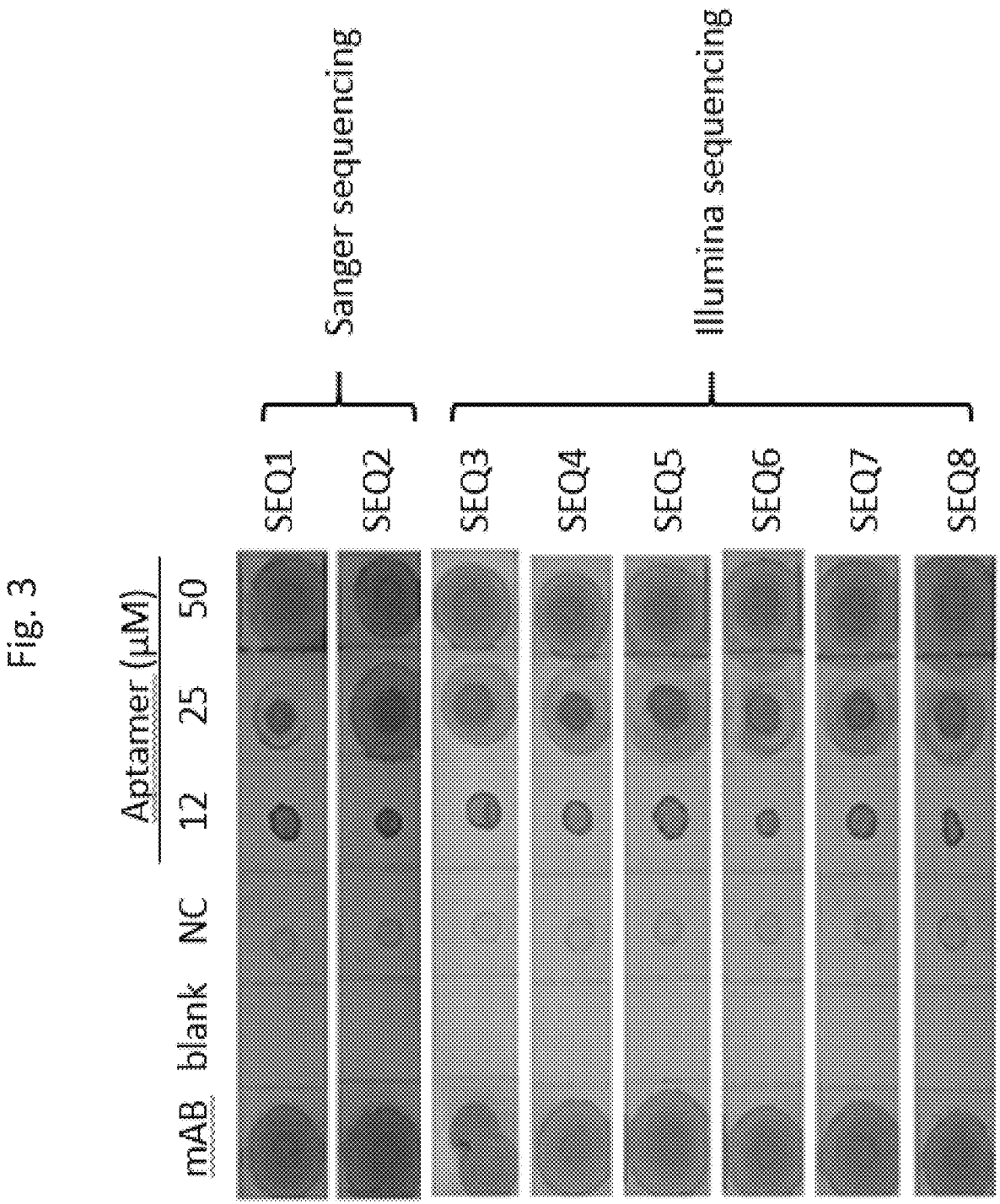
FIG. 3 shows photographs of eight membranes following a dot blot assay in which the DNA aptamer candidates were evaluated for target binding capability using 5' biotinylated synthesized oligonucleotides. The chCD40$_{ED}$ protein (15 m/mL) was fixed on an Immune-Blot PVDF membrane and incubated with the candidate aptamers at the indicated concentrations. Streptavidin was added followed by the BCIP/NBT substrate. The biotinylated anti-chicken CD40 mAb (10 μg/mL) was included as the positive control (1st column 1) and 1× imidazole phosphate buffer saline-tween was included as a negative control (NC, third column).

Dot-blot hybridization assay: To assess the ability of the candidate aptamers to bind to the target protein, a dot blot assay was performed using each of the eight aptamer candidates (SEQ ID NOs: 1-8; Table 2). All aptamer candidates demonstrated significant binding to the target protein at a concentration of 25 μM or higher (FIG. 3). It is important to note that the aptamer sequences evaluated here contained the primer binding sequences because it is possible that these sequences were important for aptamer structure and interaction with the target protein.

Figure 4A:
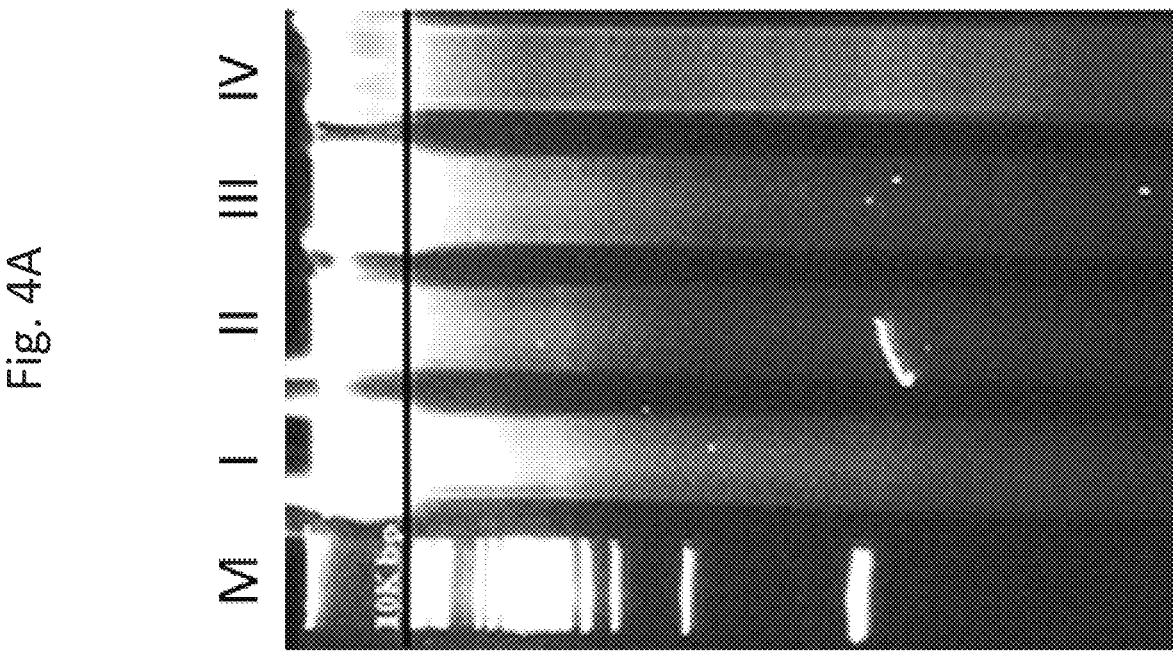
FIG. 4A shows amplified RCA products run on a 15% TBE (Tris Borate EDTA) denaturing urea gel. The complementary sequences of the eight aptamer candidates were used to prepare four RCA templates, which were amplified using single primers.
Figure 4B:
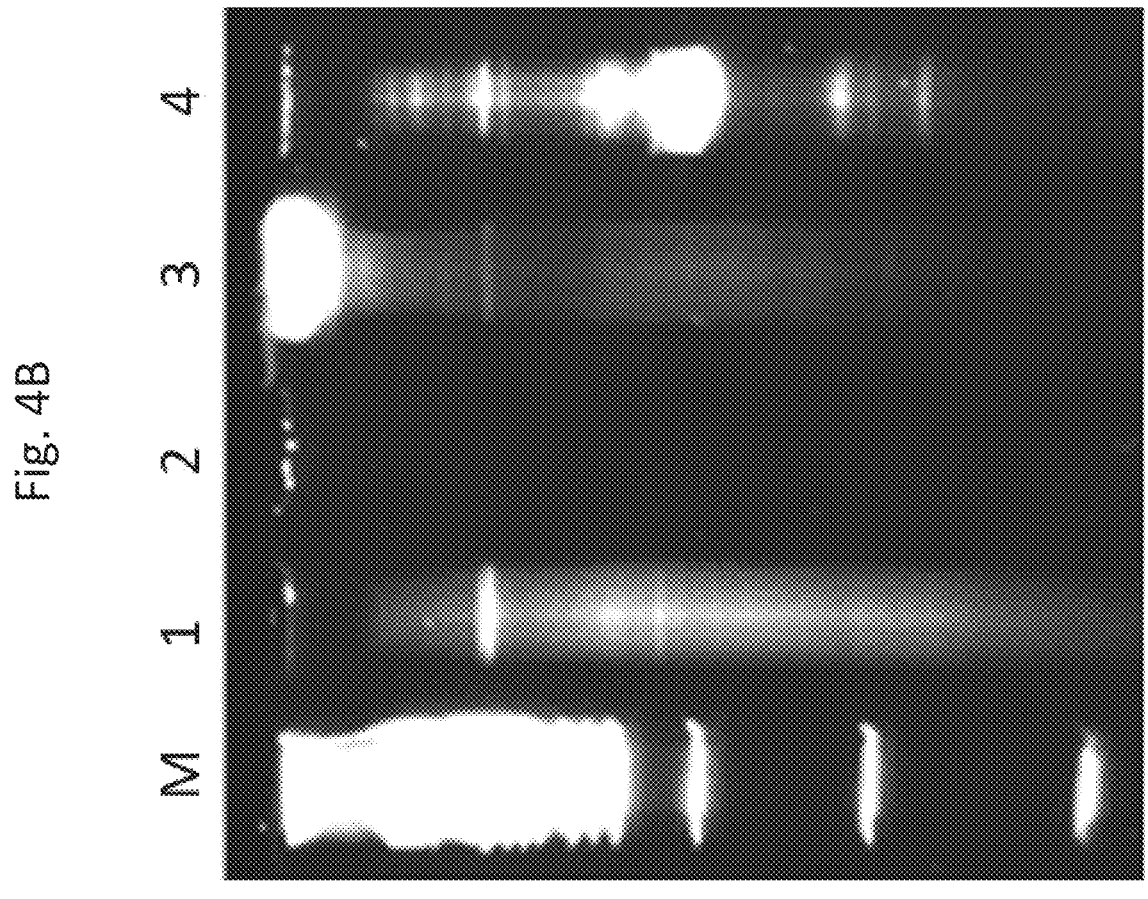
FIG. 4B shows the RCA products digested with Age I restriction enzyme. The linear single-stranded template DNA containing the spacer region was circularized using a primer and ligation by T4 DNA ligase. After incubation with φ29 DNA polymerase, the resulting RCA products were purified and precipitated. Finally, a sequence that is complementary to the spacer sequence was annealed thermally. M: 2-log DNA ladder; 1: Circularized template; 2: empty; 3: aptamer RCA II; 4: aptamer RCA digested with Age I.

Rolling circle amplification: As stated earlier, the smaller size of DNA aptamers in comparison to the target protein could prohibit adequate interaction between the aptamers and CD40. To enhance the ability of the aptamers to form a proper interaction with CD40, we produced rolling circle amplification (RCA) products that consist of these aptamer sequences. To produce these products, the reverse complementary sequences of the eight candidate aptamer sequences were used to design four templates for the RCA procedure with each RCA template consisting of reverse complementary sequences of two distinct aptamers (Table 1). Each template was composed of a primer binding site, spacer, and two aptamer sequences, enzymatically circularized with the aid of a primer. RCA produces long tandemly repeated (i.e., several hundred times) single-stranded DNA sequences, which are reverse complementary to the original circular single-stranded DNA template[28, 29]. This reaction produces RCA products of high molecular weight (FIG. 4A). To confirm the molecular configuration of the aptamer RCAs, we digested aptamer RCA II products with the restriction enzyme Age I in the presence of an oligonucleotide that is reverse complementary to the spacer region in the template, which contains the Age I recognition sequence (Table 1). This oligonucleotide is referred to as the "spacer-complement" or the "spacer complementary sequence" herein. Digestion of the aptamer RCA II products with Age I restriction enzyme predominately produced a single band, 195 nt in length (FIG. 4B). This result confirms that the aptamer RCA products consist of tandem repeats of two candidate aptamer sequences separated by a spacer region. Notably, a spacer that contains the Age I recognition site was included in the design of the aptamer RCA for two purposes: (1) to allow efficient characterization of aptamer RCA products through digestion with Age I, as described above, and (2) to facilitate folding and stability of the aptamer structure in the resulting aptamer RCA products through the formation of partially double stranded DNA in the spacer region with the addition of the spacer-complement oligo- nucleotide. This stabilizing effect is evidenced by our obser- vation that while the aptamer RCA products precipitated as aggregates in solution, these aggregates disappeared when spacer-complement was added to aptamer RCA products.

Figures 5A, 5B:
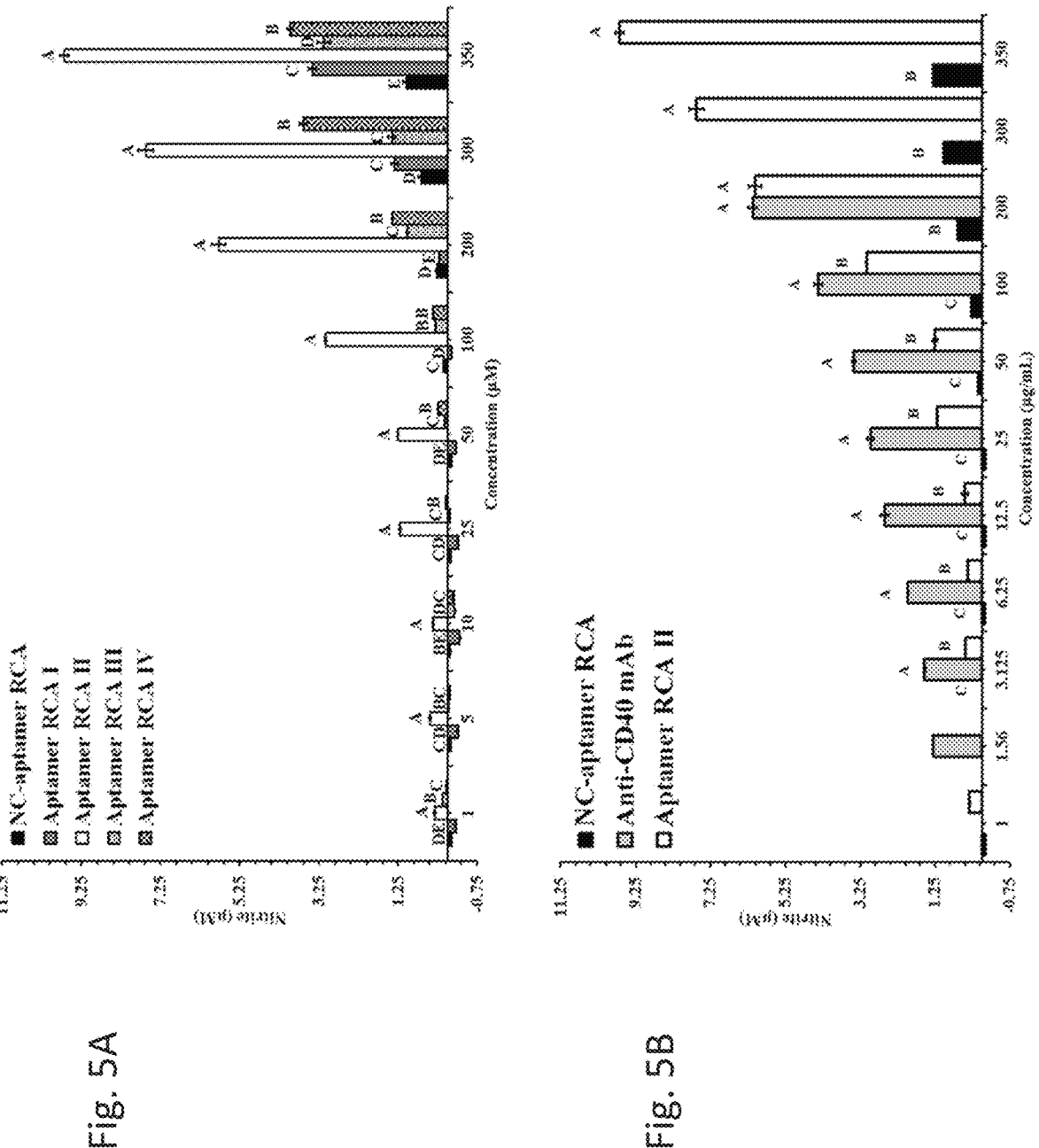
FIG. 5A-5B show bar graphs representing the concentration of nitrite released from chicken HD11 macrophage cells after treatment with the RCA products. The RCA products were incubated for 4 hours with the HD11 macrophage cells in concentrations of 1, 50, 100, 150, 200, 250, 300 and 350

Measuring the activation of macrophage cells: The aptamer RCAs were stabilized by addition of the spacer complementary sequence and were used to treat the chicken HD11 macrophage cell line[30]. The four templates (Table 1) were circularized by ligation and were used to produce four aptamer RCAs, referred to as RCA I-RCA IV. A Griess assay showed that there was elevated nitric oxide (NO) liberation in the media after the chicken macrophages were incubated with any of the four aptamer RCAs. However, there was significant variability in the efficacy and potency among the aptamer RCAs (FIG. 5A). The response was dose-depen- dent, and the aptamer RCA II demonstrated significantly higher responses as compared to all other aptamers at all concentrations evaluated (FIG. 5A). In contrast, the negative control aptamer RCA formed from two DNA sequences from the aptamer library that were not enriched in the aptamer pool (based on the Illumina sequencing results) showed no activation of the cell line. The aptamer RCA II was also compared with the anti-chicken CD40 mAb (mAb 2C5) that was previously shown to stimulate the chicken HD11 cells[19] (FIG. 5B), and was shown to stimulate the cells to a comparable level.

MALDI-TOF MS and LC-ESI-MS: MALDI-TOF mass spectrometry (MS) was used to characterize the $chCD40_{ED}$ recombinant protein. The results showed that the molecular weight of this protein was 25,712 Dalton (data not shown).[36] LC-ESI-MS was used to identify the binding sites of CD40 that were protected by the DNA aptamers of SEQ ID NO: 3 and SEQ ID NO: 4, which were used for form aptamer RCA II. Trypsin is a serine protease that catalyzes the hydrolysis of proteins at lysine and arginine residues. Thus, proteolysis experiments performed under physiological conditions coupled with LC-ESI-MS analysis can be used to identify solvent accessible surface residues, as previously demon- strated by Sides et al.[54] When CD40 forms complexes with DNA aptamers, some of the solvent accessible lysine and arginine residues near the attachment site become less accessible to trypsin. Hence, the LC-ESI-MS intensities of tryptic peptides are expected to be lower in signal intensity at such residues, as compared to control chCD40ED without the aptamers.

Figure 6A:
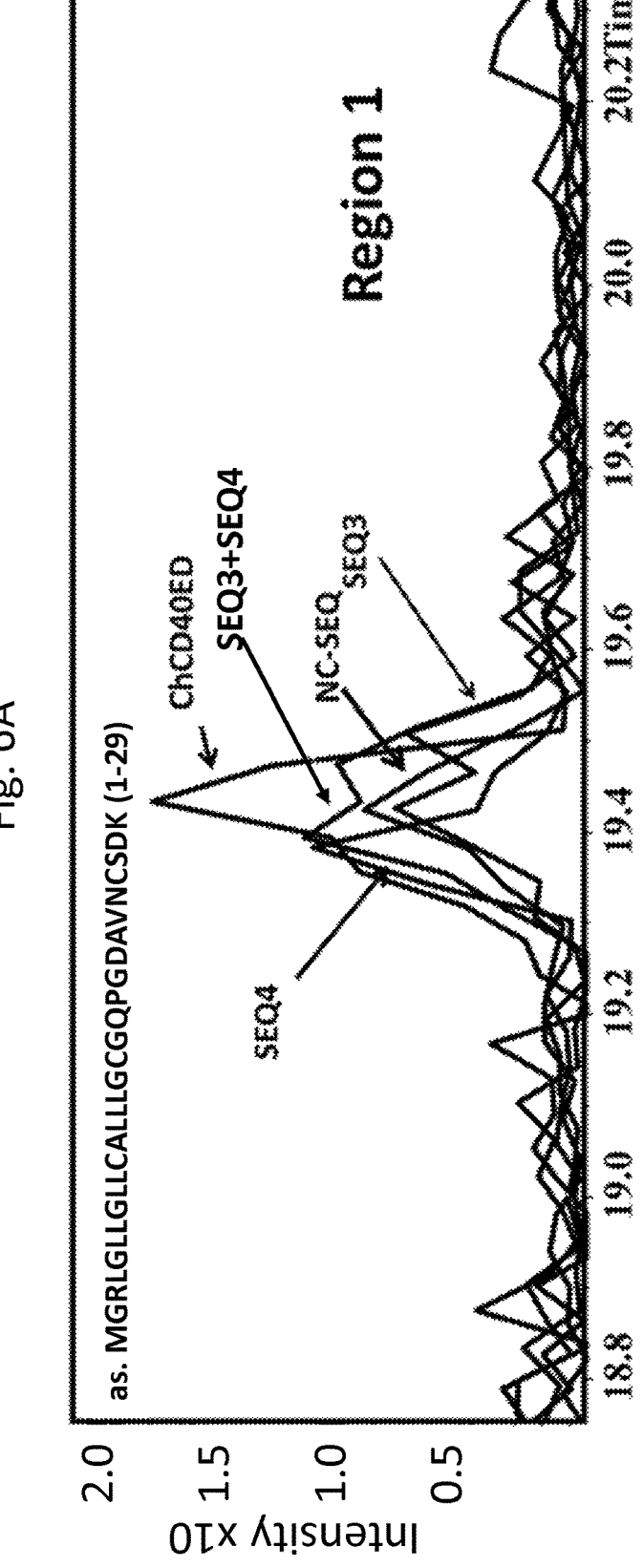
FIG. 6A-6E show line graphs representing Matrix-Assisted Laser Desorption/Ionization-Time Of Flight (MALDI-TOF) mass spectrometry (MS) readings taken after incubating recombinant chCD40$_{ED}$ protein (25,712 Daltons) with the aptamers (SEQ ID NO: 3 only, SEQ ID NO: 4 only, both SEQ ID NO: 3 and SEQ ID NO: 4, or a negative control (NC-SEQ)) and subjecting the protein to trypsin digestion overnight. Three distinct regions on the protein sequence were protected from digestion: region 1 is shown in FIG. 6A (amino acids 1-29 of SEQ ID NO: 9), region 2 is shown in FIG. 6B (amino acids 30-34 of SEQ ID NO: 9), and region 3 is shown in FIG. 6C (amino acids 37-40 of SEQ ID NO: 9). The data are reported as intensity (y-axis) over time (in seconds, x-axis). A fourth region (FIG. 6D; amino acids 172-176 of SEQ ID NO: 9) and a fifth region (FIG. 6E; amino acids 177-191 of SEQ ID NO: 9) demonstrated little protection.
Figure 6B:
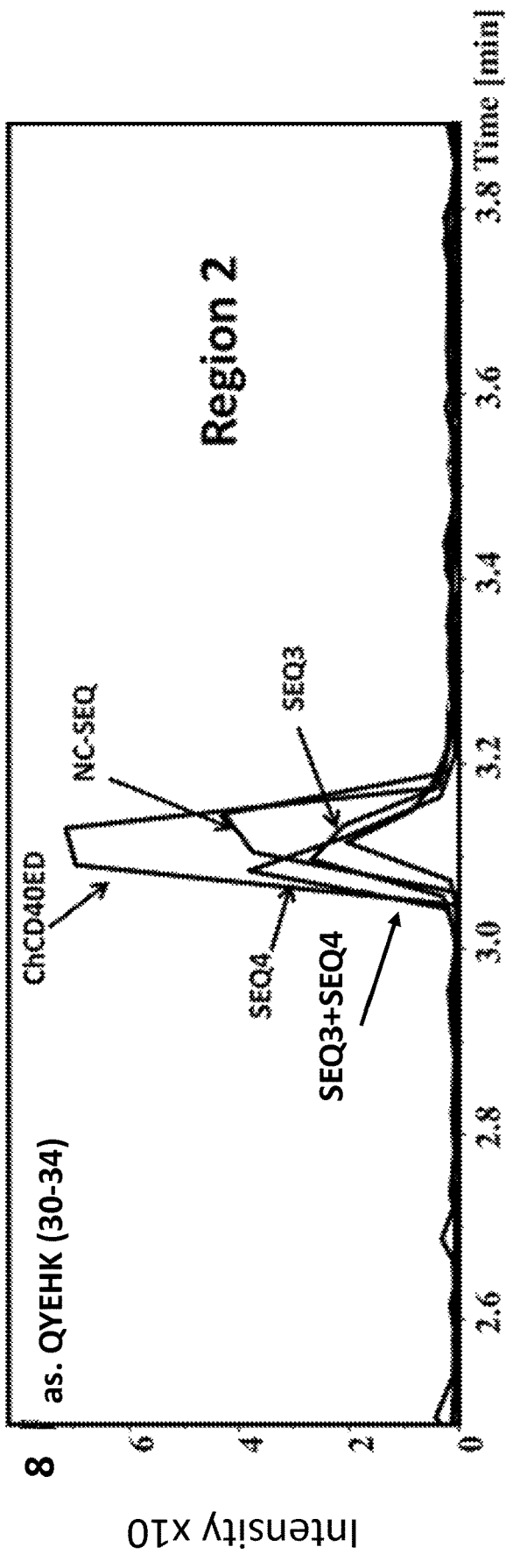
Figure 6C:
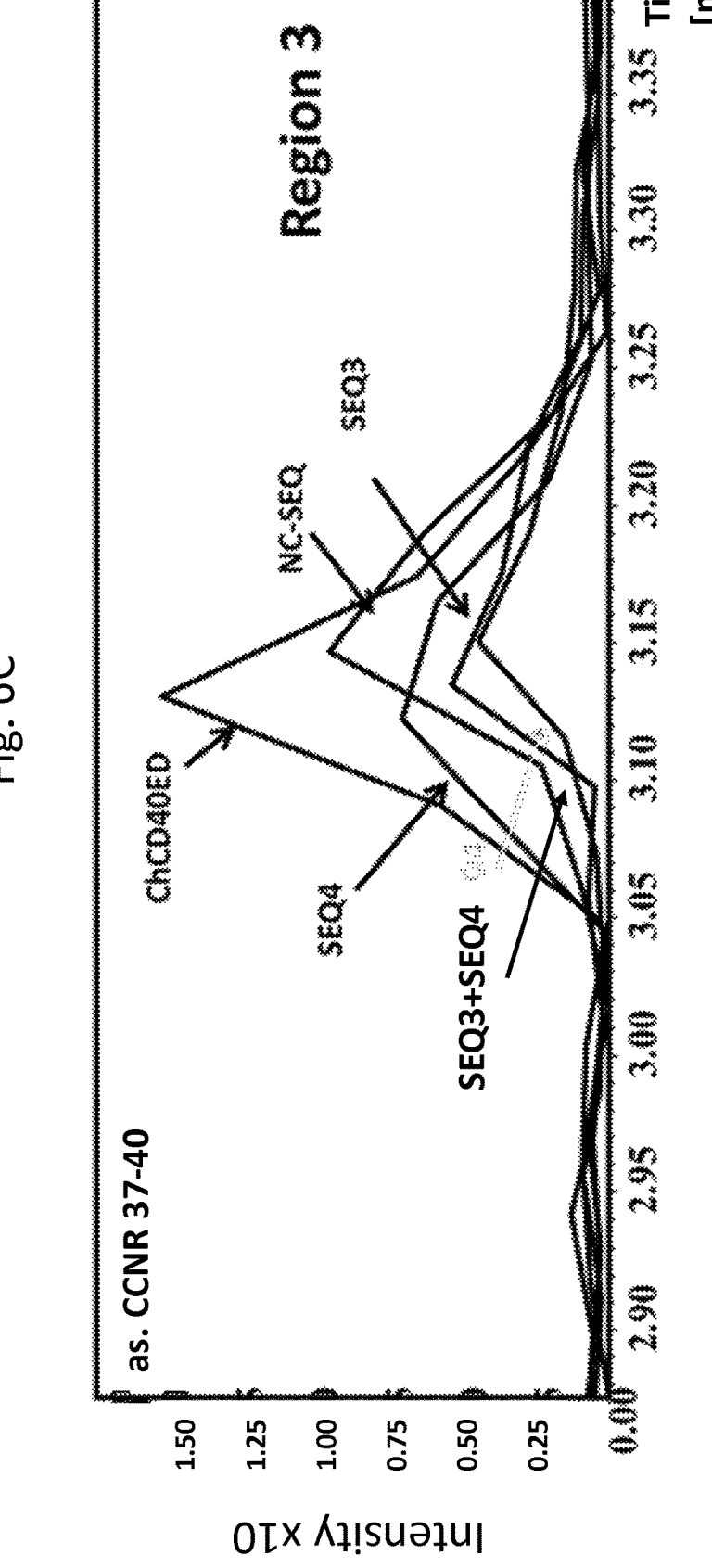
Figure 6D:
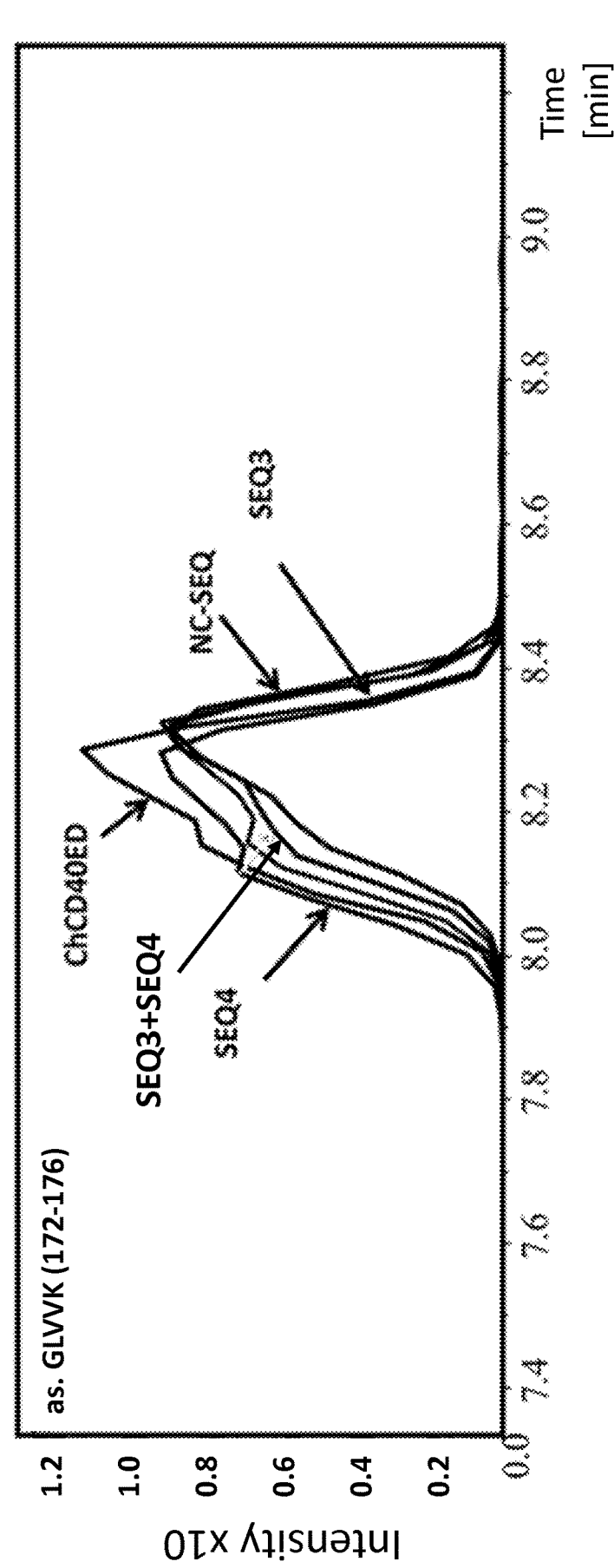
Figure 6E:
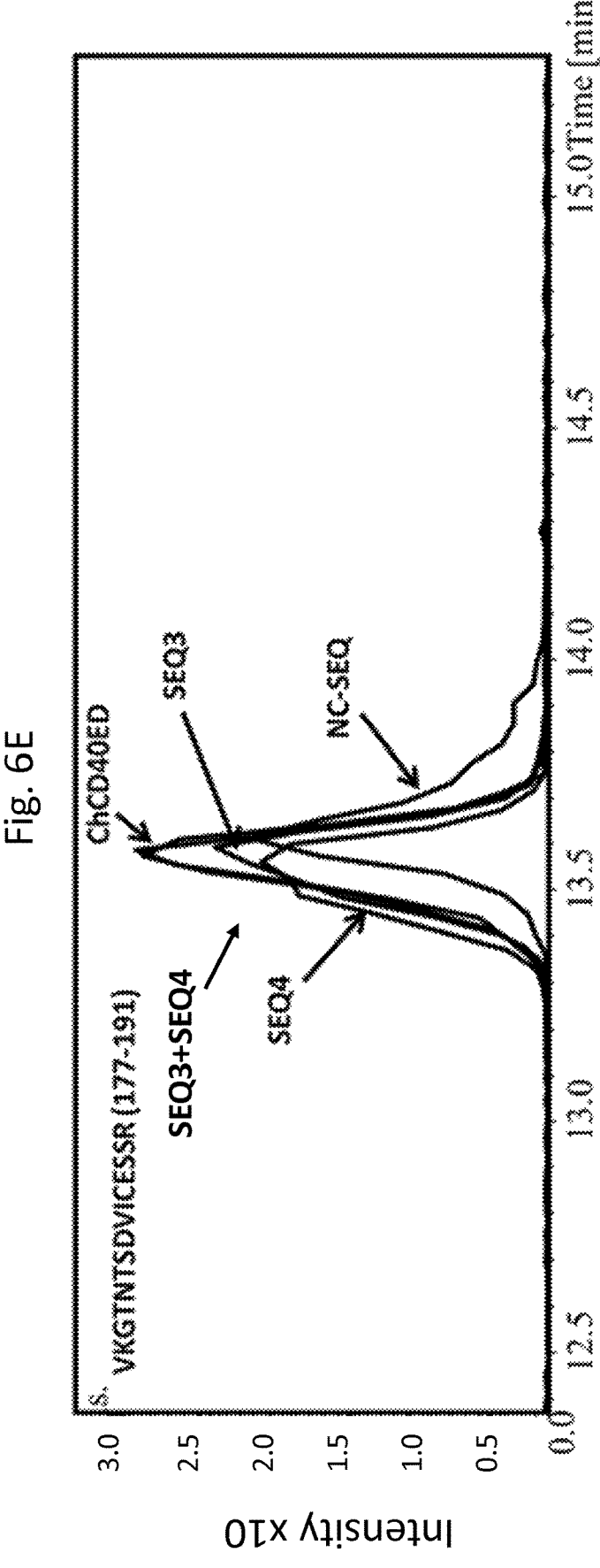
Figure 6E:
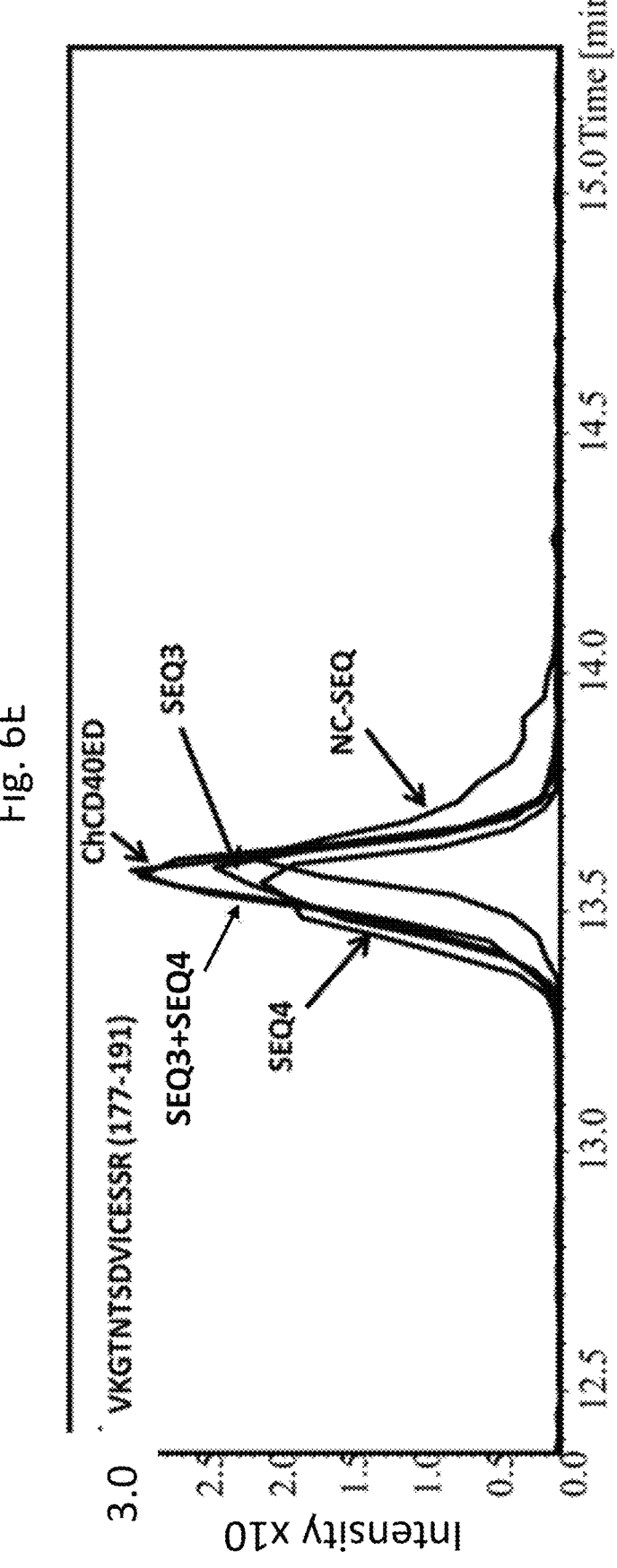
Figure 7A:
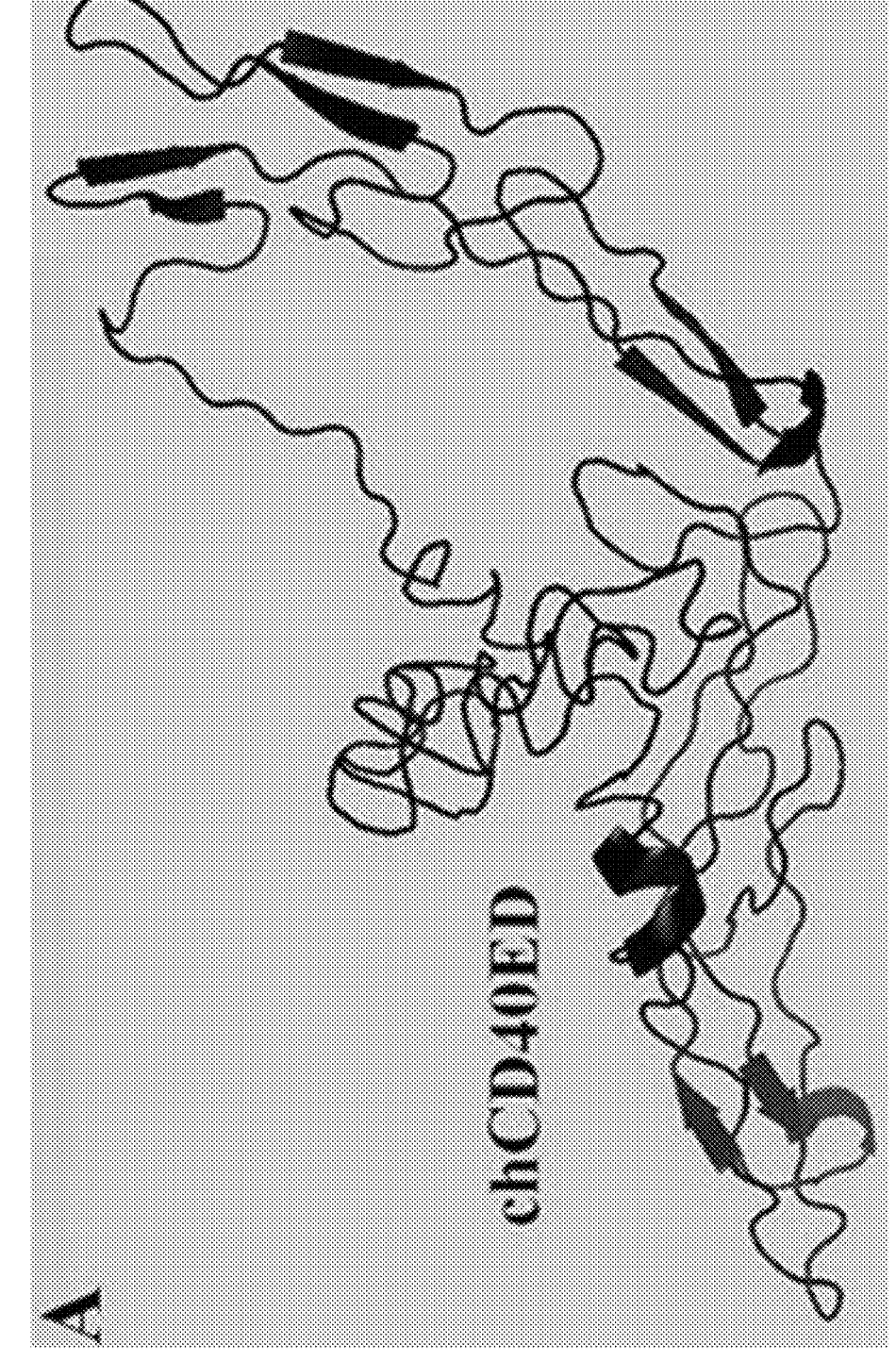
FIG. 7A-7D show virtual tertiary structures of chCD40$_{ED}$, highlighting potential aptamer interaction sites.
Figure 7B:
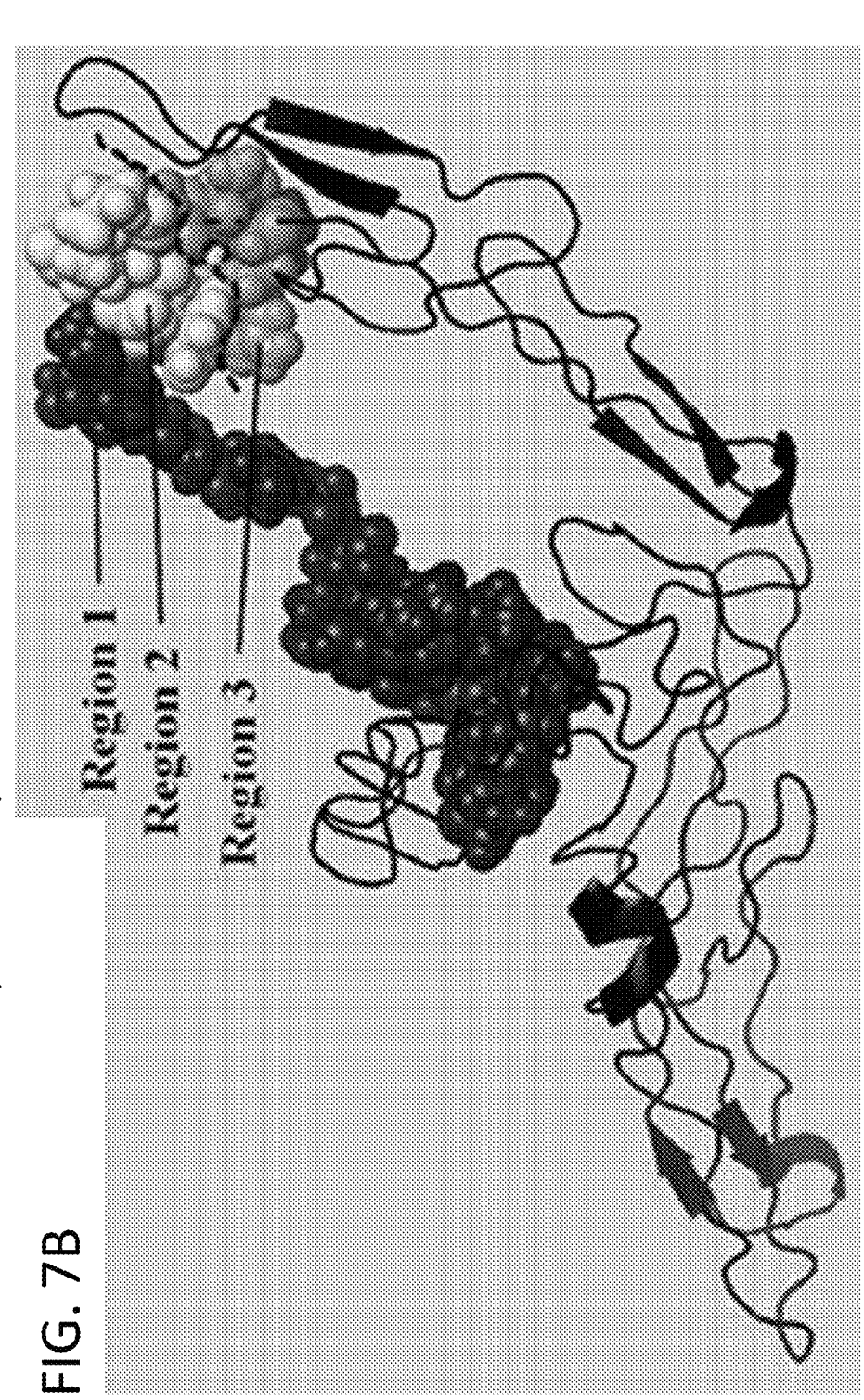
Figures 7C, 7D:
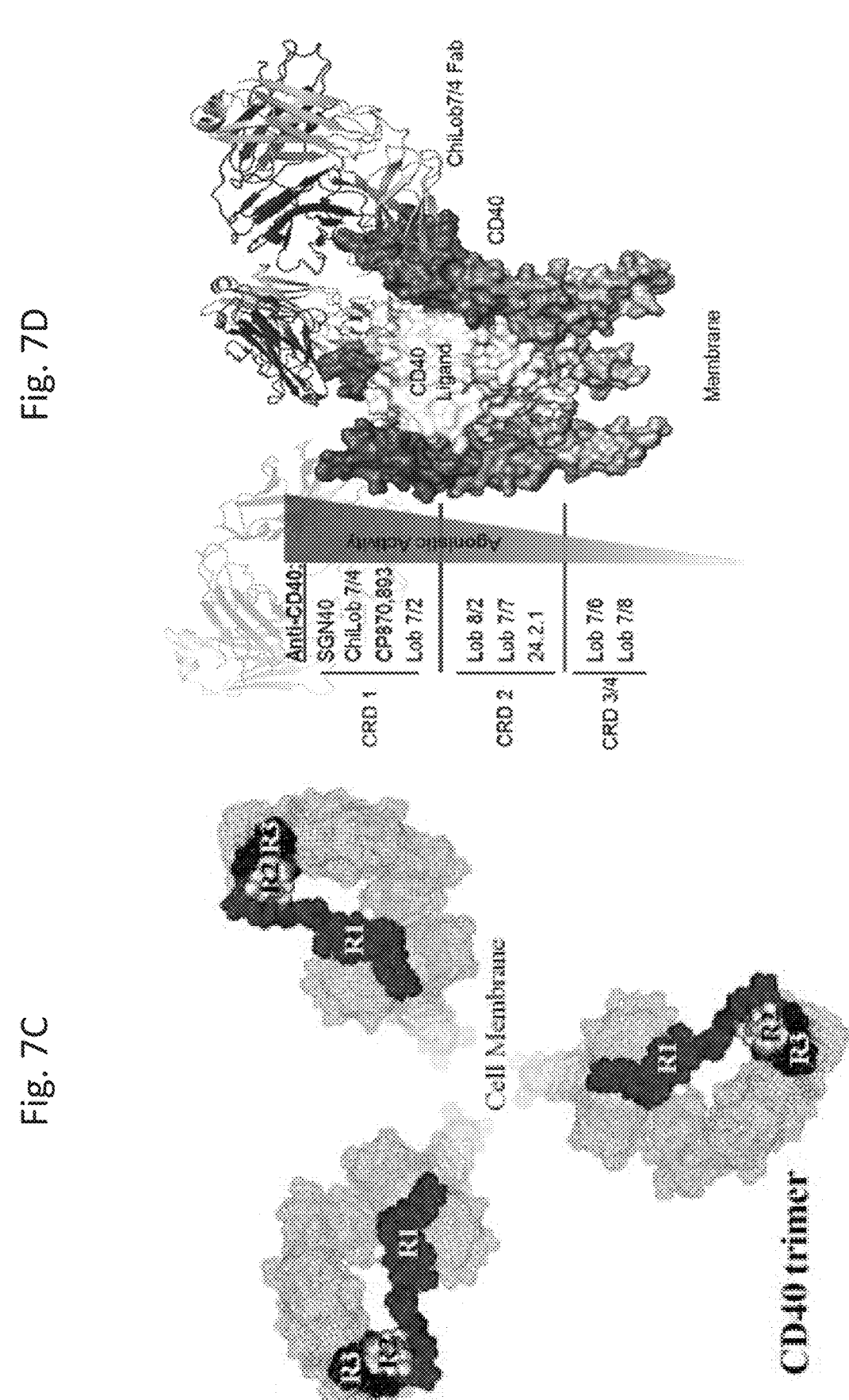

Extraction ion chromatograms corresponding to tryptic peptides shown in FIG. 6A-6C suggest that binding of the aptamers to CD40 blocked trypsin digestion at three differ- ent peptide segments: residues 1-29 (region 1), residues 30-34 (region 2), and residues 37-40 (region 3) at the N-terminus of CD40. Each peak indicates a sequence within the protein that was protected by the binding of the aptamers of SEQ ID NO: 3 and SEQ ID NO: 4, separately or in combination (FIG. 7A-7C). Further, FIG. 6D-6E show regions (covering residues 172-176 and 177-191, respec- tively) that had almost no change in extracted ion chromato- gram intensity as compared to the protein only control. Consistent with the results of the Griess assay, where the negative control aptamer (NC-aptamer) RCA was able to stimulate NO liberation at a low level (FIG. 5A-5B), the NC-aptamer also showed low, yet detectable, protection activity against the action of trypsin enzyme. However, SEQ ID NO: 3 and SEQ ID NO: 4 showed higher and more consistent protection in regions 2 and 3 as compared to the NC-aptamer (FIG. 6B and FIG. 6C, respectively). In con- trast, the other two regions show little protection (FIG. 6D-6E), indicating that the aptamers did not bind these regions. In addition, to determine the site(s) where the aptamers bind the target protein, the data from the LC-ESI- MS were subjected to virtual protein tertiary structure analy- sis using the Phyre2 Protein Fold software. According to this analysis, SEQ ID NO: 3 and SEQ ID NO: 4 interact with the N-terminus of the target protein (FIG. 7B) and bind to it in a synergistic fashion (FIG. 6A-6C). In the tertiary structure of our target protein, significant peptide regions could not be constructed by the software we tested. This could be attrib- uted to the fact that this region is flabby (highly resonant) and could not be predicted reliably. Interestingly, the three predicted aptamer-protein binding sites are included in this region (FIG. 7A). It is important to note that in the actual CD40-CD40L interaction, the ligand spans the inner parts of the receptor, pulling the extra domains inward and leading to oligomerization of the receptor (FIG. 7D).[37] In our receptor- aptamer interaction model, the receptor is bound apically by the aptamer RCA II. Clustering of CD40 receptor trimers at the solvent-exposed flexible regions of the aptamer appears to be a critical step that causes the same effect as the receptor-ligand clustering and oligomerization (FIG. 7C).

Example 2—In Vivo Assessment of Vaccines Based on CD40 Aptamers

In Example 1, we developed DNA aptamers selected against the extracellular domain of the chicken CD40 recep- tor ($chCD40_{ED}$) and demonstrated that these aptamers stimulate macrophages in vitro (FIG. 5A, 5B). In the fol- lowing example, we performed an immunization trial in chickens using an immune complex comprising a DNA aptamer-based RCA adjuvant conjugated with a peptide antigen. The results of this trial showed that the immune complex could induce a significant IgG antibody response, which was sustained for four weeks post-immunization.

Materials and Methods:

Chickens: The conditions for animal use in this study were met and approved by the Institutional Animal Care and Use Committee (IACUC) of the University of Arkansas. A total of 120 broiler one-day-old chicks were tag-divided into six groups (n=20) in comingle pen. The chicks were single gender Cobb-Vantress off-sex obtained on the day-of-hatch from the Fayetteville hatchery, Fayetteville, AR The chicks were mechanically block randomized by moving ⅓ of each of the chicks from three boxes to a single new chick box, thus, equally re-mixing each of the boxes. This was done in case the boxes were derived from different hatchers or different breeder sources (this variability has historically been critical for randomization effects). Broiler management protocols from Cobb were used in raising the birds (cobb- ventress.com).

Rolling circle amplification products: Aptamer develop- ment and RCA preparation are described in Example 1. Importantly, the RCA products were synthesized as bioti- nylated DNA using biotinylated primers (IDT, Coralville, Iowa, USA) to facilitate conjugation with streptavidin in later steps.

Peptide immunogen: A commercially produced, synthetic M2e peptide was ordered with N-terminal biotinylation (GenScript Inc. Piscataway, IL). This peptide, NAWSKE- YARGFAKTGK (SEC) ID NO: 22), represents the ectodo- main of the influenza virus matrix protein 2. To form an immune complex, two biotinylated RCA molecules and two biotinylated M2e peptide were conjugated by one streptavidin molecule (see below).

Figure 8:
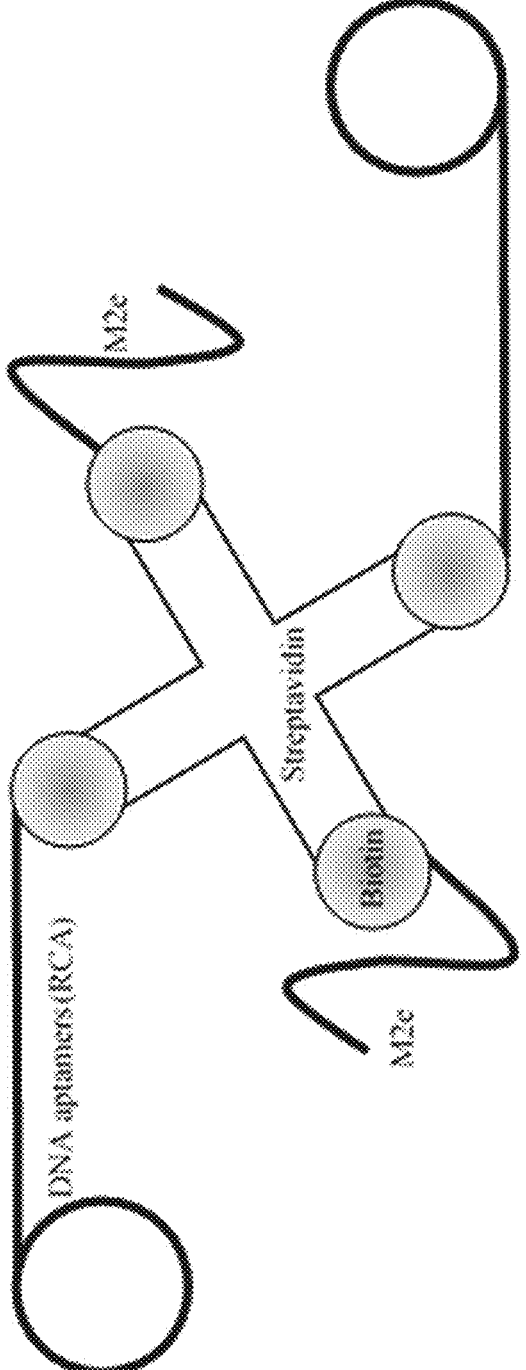
FIG. 8 shows a schematic of an exemplary vaccine complex. Streptavidin is a central molecule that may coordinate biotinylated components of the vaccine. The biotinylated aptamer RCA and biotinylated M2e peptide were mixed together at a 1:1 molar ratio, which was then mixed with streptavidin at a 2:1 molar ratio to form the conjugated vaccine complex.

Immunizing complex preparation and administration: Immunization complexes were prepared as described elsewhere[19]. Briefly, streptavidin (Thermo Fisher Scientific Inc., Rockford, IL) was used as the central conjugating molecule (FIG. 8). The peptide was ordered in a biotinylated form (GenScript Inc. Piscataway, IL), whereas biotinylation of the RCA products was accomplished using biotinylated primers in the RCA procedure. The biotinylated peptide (0.2 µg) was mixed with the biotinylated RCA products (RCA-p, 50 µg) at a 1 to 1 molecular ratio in 1×PBS with rotation at RT for 3 hrs. The peptide-RCA-p mixture was then added to streptavidin in a 2 to 1 ratio with stirring at 4° C. for 3 hrs. The same procedure was followed when preparing the immune complexes comprising anti-CD40 monoclonal antibody, the peptide alone, or the RCA-p alone. Similarly, the ratio of the peptide/RCA-p alone to streptavidin was 2 to 1.

Immunization doses and timing are described in Table 4. Chickens were divided randomly into 6 groups in a comingle pen (n=20/group) and immunized with two different doses of RCA-streptavidin-peptide immune complex (low: 25 µg/bird and high: 50 µg/bird). Birds were immunized twice: primed at 7 days of age and boosted at 21 days of age by the subcutaneous route. The results of this treatment were compared to those generated with an anti-chicken CD40 monoclonal antibody-based adjuvant that was given twice at 50 µg/bird, and with three negative control groups. The total administered volume for either immunizing formula was 0.4 mL/bird. The excipient of the vaccine was emulsified PBS [5% (v/v) squalene, 0.4% (v/v) Tween 80 (Sigma-Aldrich, St. Louis, MO) in PBS].

Blood sampling: Blood sampling was performed at weekly intervals. Blood was collected from the jugular vein at week 1 and from the wing vein for the next four weeks. Sera was separated from whole blood by centrifugation, and then stored at −20° C. until use.

Quantification of peptide-specific IgG by ELISA: The level of anti-M2e IgG in the sera was quantified by ELISA. All serum samples were tested in duplicate. First, the biotinylated peptide was incubated with 5 µg/mL goat anti-biotin antibody (ThermoFisher Scientific Inc., Rockford, IL) in 0.05M carbonate-bicarbonate buffer (pH 9.6) in a 1 to 1 molar ratio for 2 hrs at RT with rotation. The resulting M2e-antibody complex was then coated onto a 96-well microliter plate (MaxSorb, Thermo Fisher Scientific Inc.) overnight at 4° C. Next, the un-absorbed supernatant was removed and the plate was washed with PBS-T and blocked with 100 uL commercial blocking buffer (SuperBlock, ThermoFisher Inc.) for 1 h at RT. After a series of washes with PBS-T, the plate was incubated with the investigated sera [(100 uL/well), diluted 1:500 in PBS to blocking buffer (1:1), 1% normal goat serum (v/v) and 1% normal rabbit serum (v/v)] overnight at 4° C. After another series of washes, the plate was loaded with 100 uL of horseradish peroxidase-conjugated, affinity-purified, isotype-specific rabbit anti-chicken IgY antibody (ThermoScientific Inc.). Secondary antibody was diluted to 1:30,000 in PBS containing 5% bovine serum albumin (BSA) and 1% normal goat serum (v/v). The plate was incubated for 1 h at RT, followed by a course of five washes. For color development, OptEIA™ TMB substrate (BD, Lakes, NJ) was applied following the manufacturer instructions. Color development was terminated after 5 minutes by adding 1N sulfuric acid (50 µL/well). Absorbance was measured by using a BioTeK microplate reader (BioTek Instruments, Inc., Winooski, VT, USA) at 450 nm and Gen5™ data analysis software (BioTek Inc.).

Statistical analysis: The relative level of anti-peptide antibody in the sera was normalized by calculating the mean value of each group, using the mean of the non-immunized group as the negative control (S-N) baseline. One-way analysis of variance (ANOVA) with least significant differences (LSD) of the means of the S-N values and student's t-test were used to determine the significant differences between the treatments. All data were analyzed using JMP software (SAS institute Inc., Cary, NC, software by the University of Arkansas). Statistical differences of the RCA-peptide immunized group were determined at a significance level of p=0.0001.

Figure 9A:
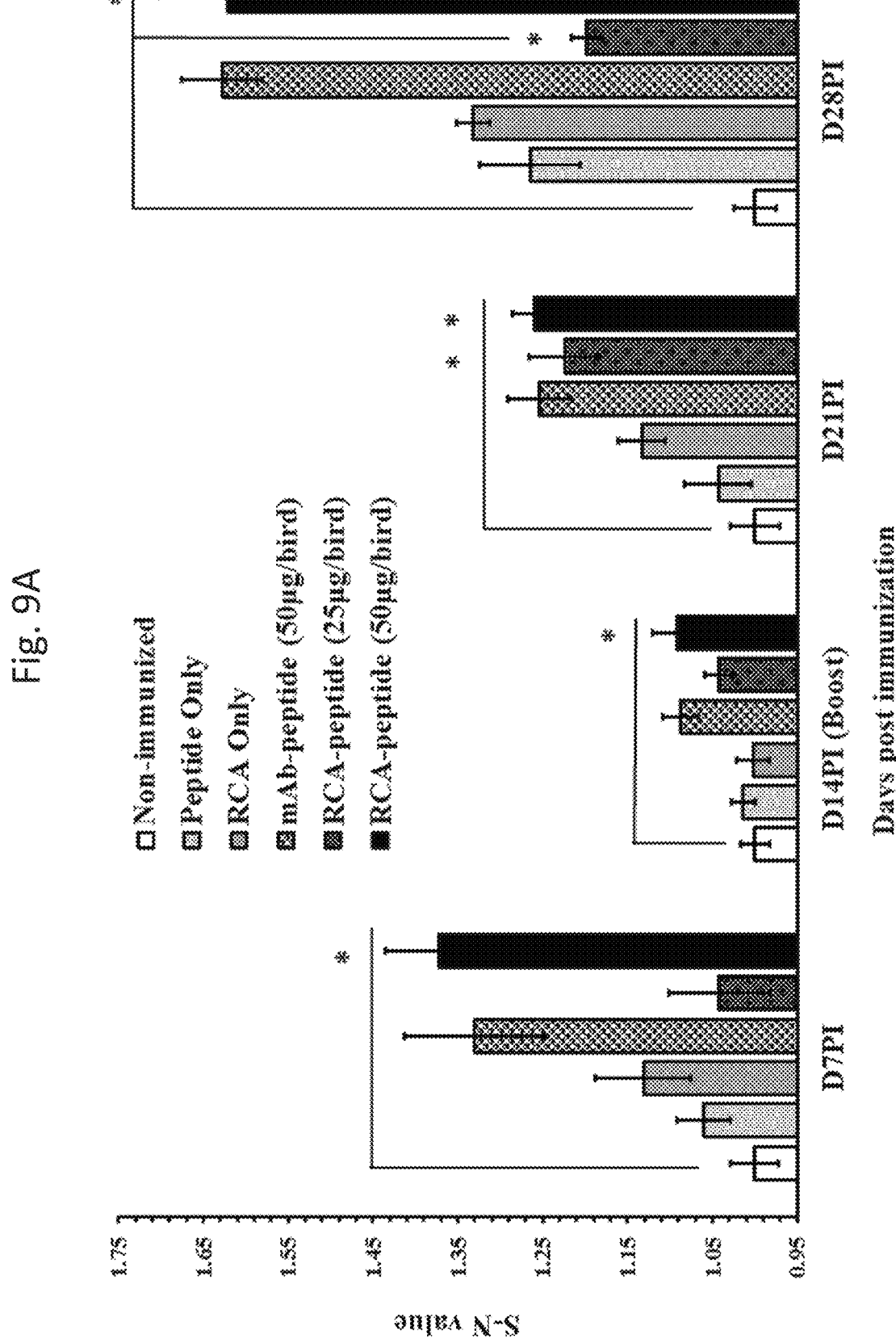
FIG. 9A-9B show bar graphs representing normalized levels of the anti-M2e IgG in chicken sera measured by ELISA at weekly intervals following immunization. Birds were immunized at day 7 and day 21 by the subcutaneous route with (1) negative control (non-immunized), (2) M2e peptide (peptide only), (3) aptamer RCA II (RCA only), (4) mAb-SA-M2e (mAb-peptide), (5) aptamer RCA II-SA-M2e complex (RCA-peptide) at 25 μg/bird, or (6) RCA-peptide at 50 μg/bird (n=20/group). The data was normalized using the following calculation: S-N value=(any read−mean reads of the non-immunized group). Results are shown as the mean±SE and differences were determined using ANOVA and student t-test. Asterisks represent statistically significant differences (p=0.0001) as compared to the non-immunized control group.

Results and Discussion:

Evaluation of the novel immunization complex in the chicken model: As discussed in the Background section, activation of the CD40 receptor plays a central role in mounting an adaptive immune response. In this study, tested the ability of CD40 aptamer RCA products conjugated to an influenza M2e peptide to act as an adjuvant. Specifically, we evaluated the ability of immune complexes comprising aptamer RCA II (which induced the most robust activation of HD11 macrophage cell line in Example 1) to elicit a M2e-specific immune response at two different doses (aptamer RCA-SA-M2e, FIG. 8). These results were compared to those generated with several negative controls (no-vaccination group, SA-M2e, and aptamer SA-RCA) and with our previously tested immune complex comprising mAb 2C5 (mAb-SA-M2e) (Table 4). As reported previously, mAb 2C5 conjugated with M2e peptide induced a high antibody titer directed against M2e peptide in immunized chickens[19]. Our results show that the anti-M2e IgG antibody titer was detected as early as 7 days post-immunization. When given at the high dose, the aptamer RCA II-SA-M2e complex showed a significantly higher response as compared to the no-immunization control (FIG. 9A). This high titer was sustained to the end of the experiment. These results are comparable with those obtained with mAb-SA-M2e. The administration of 50 µg/bird of aptamer RCA II-SA-M2e complex induced significant level of anti-M2e IgG titer for a long-term period (p=0.0001, FIG. 9B).

Table 4. Experimental design of in vivo immunogenicity trial: Six groups (n=20) were raised in a comingle pen and immunized twice with two different doses of RCA-SA-M2e immune complex (i.e., low: 25 µg/bird and high: 50 µg/bird). This immune complex composition was compared with anti-chicken CD40 monoclonal antibody-based immune complex that has been given twice at 50 µg/bird. In addition, the tested immune complex was compared with three negative control groups.

| Group | Vaccine | Description of the vaccine‡ | Dose/ bird* | prime/ route | boost/ route |
|---|---|---|---|---|---|
| 1 | Negative-negative control | No vaccination | NA | NA | NA |
| 2 | Negative control | SA-M2e | 0.2 µg | D7/SC | D21/SC |

-continued

| Group Vaccine | Description of the vaccine‡ | Dose/ bird* | prime/ route | boost/ route |
|---|---|---|---|---|
| 3 Negative control | SA-aptamer RCA II | 50 μg | D7/SC | D21/SC |
| 4 mAb-based vaccine | 2C5-SA-M2e | 50 μg | D7/SC | D21/SC |
| 5 Aptamer RCA-based vaccine | aptamer RCA II-SA-M2e | 25 μg | D7/SC | D21/SC |
| 6 Aptamer RCA-based vaccine | aptamer RCA II-SA-M2e | 50 μg | D7/SC | D21/SC |

Figure 9B:
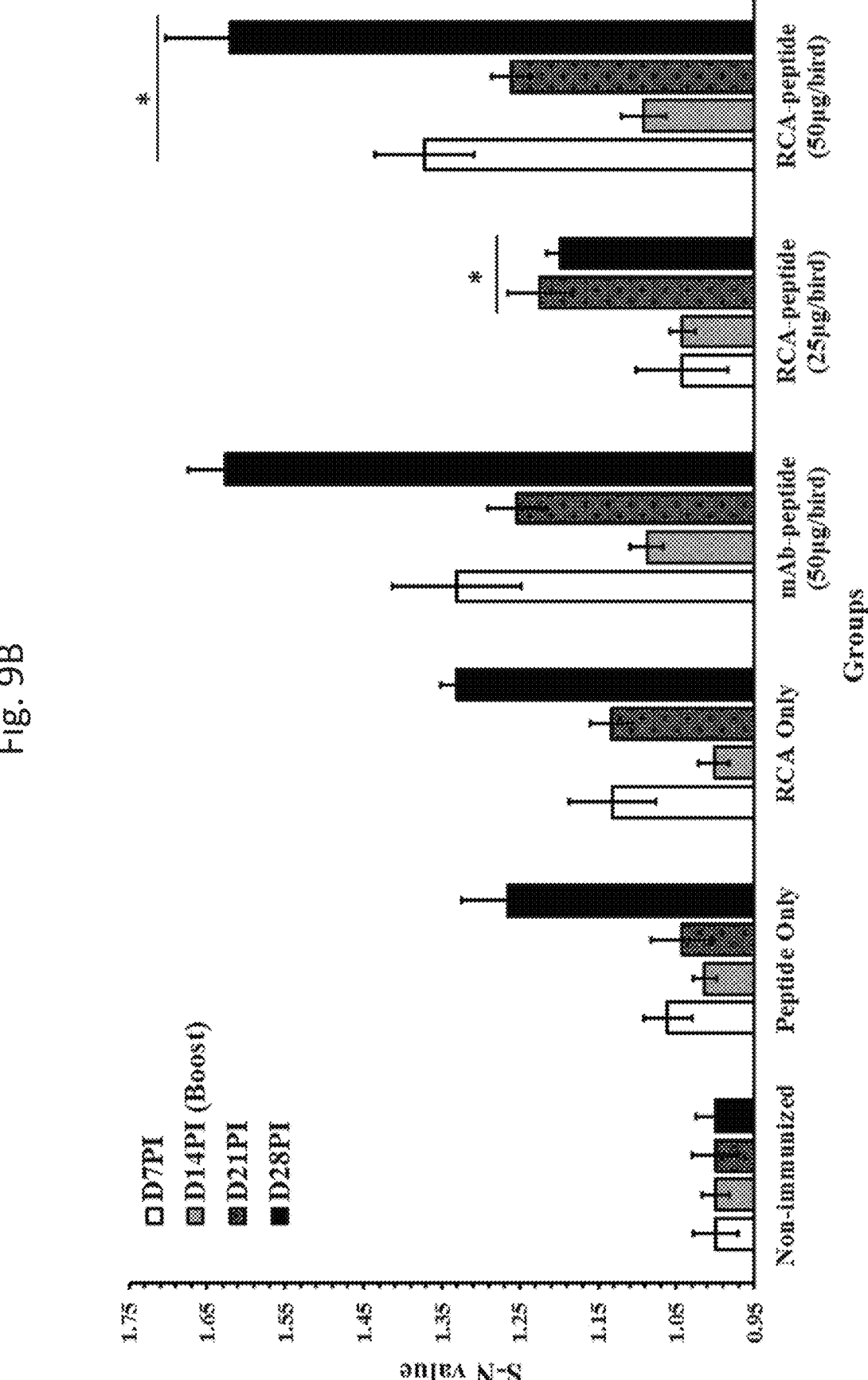

At the lower dose (25 μg/bird), the same immune complex failed to induce significant level of anti-M2e IgG in the sera at 7- or 14-days post first immunization. However, when this immune complex was used for boosting at day 14, it induced significant level of the antibody titer at 28 days post the first immunization (FIG. 9A-9B). All birds showed retarded immune response at day 14 post immunization. Our record showed some management issues during the day before the onset of blood sampling. This might have caused stress in the birds at that particular timepoint. However, it appears that the birds compensated via immune response against the antigen in later weeks.

CONCLUSIONS AND SIGNIFICANCE

In recent years, aptamers and aptamer-based molecules have been used in place of mAbs in many areas of molecular biology and biotechnology. However, expansion in this field is yet to overcome the limitations of the use of the aptamers due to poorly understood molecular properties of these molecules. The foregoing examples demonstrate that aptamer RCAs are capable of activating chicken macrophage HD11 cell line via interaction with the CD40 receptor. We report the first description of the use of aptamer RCAs as an agonist for a receptor for the purpose of enhancing immune response, including chCD40$_{ED}$. The synthetic aptamers in the form of aptamer RCA mimic the naturally occurring receptor/ligand interaction, leading to receptor oligomerization. We also characterized the aptamer binding sites on chCD40$_{ED}$ by demonstrating that DNA aptamers can block the action of the trypsin enzyme on the target protein by using LC-ESI-MS experiment. Herein, we determined the peptide regions where the aptamers bind to the protein. In this study, we used monomer chCD40$_{ED}$ instead of the trimer as our target protein for aptamer selection. However, our protein was expressed in eukaryotic cell line system, which should support the post-translation modification. In naturally occurring CD40-CD40L interaction stoichiometry, upon initial physical contact of the ligand with its cognate receptor, the receptor undergoes clustering at the extracellular domain, and signal transduction occurs through the cytoplasmic domain[40]. The receptor's extracellular crosslinking is what leads to receptor oligomerization and this observation was recorded with the natural and artificial agonists of the CD40; i.e., CD40L and anti-chicken CD40 MAb[40, 41]. The ligand has to interact with the receptor in a specific manner to induce the response. Interestingly, soluble CD40L was not able to induce the expected receptor signaling nor many other anti-chicken CD40 mAbs. The results suggest that there are specific patterns and sites for ligand binding to allow efficient signal transduction[42]. Our aptamers did not show any agonistic activity when administered to the macrophage cell line as an individual nor combined aptamers (data not shown). The stimulation only occurred with aptamer RCA. Similarly, we have proven that not all the aptamers we have selected were able to significantly oligomerize the receptor; only those that were able to link specific receptor sites were successful[43-45].

The Examples demonstrate the creation of synthetic molecules that are beneficial when loaded with appropriate antigen to act as an adjuvant. The flexibility we provide with the use of aptamer-based RCA makes it easier to introduce the aptamers into the biological systems. Indeed, the aptamer RCAs are naturally protected against any nuclease enzyme activity at the downstream due to the attached circular template (data not shown).

In the chicken study, despite the use of relatively low concentration of the hapten, our aptamer RCA II-M2e complex successfully induced high level of anti-M2e IgG antibody titer in the chicken sera at the dose of 50 μg/bird. With this dose, the elevation of the antibody titer started to increase as early as seven days post immunization and remained high to the end of the experiment. The action of this immune complex proves that this complex has high potency and efficacy. These results are comparable to the result with mAb-SA-M2e complex. However, lower dose of the same complex (25 μg/bird) yielded only low level of the antibody titer and needed a booster dose to sustain relatively acceptable level of the same antibody titer at the end of the experiment.

Our immune adjuvant might work as well as universal adjuvant with any short soluble antigenic peptide. The immune response course with this DNA aptamer-based RCA immunogenic adjuvant would work via APCs-T$_H$ cells interaction pathway.

Finally, targeting the CD40 receptor with DNA aptamers as cheaper molecules, easier to prepare and more stable, would improve the effectiveness of many vaccines not only in the agricultural animal field but also in the development of human vaccines in general.

REFERENCES

1. Ma, D. Y. & E. A. Clark. The role of CD40 and CD40L in dendritic cells. Semin. Immunol. 21(5), 265-272. (2009).
2. Suttles, J. & R. D. Stout. Macrophage CD40 signaling: a pivotal regulator of disease protection and pathogenesis. Semin. Immunol. 21(5), 257-264. (2009).
3. van Kooten, C. & J. Banchereau. Functions of CD40 on B cells, dendritic cells and other cells. Current Opinion in Immunol. 9, 330-337. (1997).
4. Amitage, R. J. et al. Molecular and biological characterization of a murine ligand for CD40. Nature. 357, 80-82. (1992).
5. Kawabe, T. et al. CD40/CD40 ligand interactions in immune responses and pulmonary immunity. Nagoya J. Med. Sci. 73, 69-78. (2011).
6. Kagan, J. Signaling organelles of the innate immune system. Cell. 151(6), 1168-1178. (2012).

7. Sousa, C. R. Activation of dendritic cells: translating innate into adaptive immunity. Curr. Opin. Immunol. 16, 21-25. (2004).

8. Thaiss, C. A. et al. Chemokines: a new dendritic cell signal for T cell activation. Front. Immunol. 2, 31. (2011). doi: 10.3389/fimmu.2011.00031.

9. Corthay, A. A three-cell model for activation of naïve T helper. Scand. J. Immunol. 64, 93-96. (2006).

10. Curtsinger, J. M. et al. Inflammatory cytokines provide a third signal for activation of naïve CD4+ and CD8+ T cells. J. Immunol. 162, 3256-3262. (1999).

11. Erf, G. F. Cell-mediated immunity in poultry. Poult. Sci. 83, 580-590. (2004).

12. Noelle, R. J. et al. A 39-kDa protein on activated helper T cells binds CD40 and transduce the signal for cognate activation of B cells. Proc. Natl. Acad. Sci. 89, 6550-6554. (1992).

13. Elgueta, R. et al. Molecular mechanism and function of CD40/CD40L engagement in the immune system. Immunol. Rev. 229(1), 1-32. (2009).

14. Alvarez, D. et al. Mechanisms and consequences of dendritic cell migration. Immunity. 29(3), 1-31. (2008).

15. Stavnezer, J. et al. Mechanism and regulation of class switch recombination. Annu. Rev. Immunol. 26, 261-292. (2008).

16. Wu, C. et al. Soluble CD40 ligand-activated human peripheral B cells as surrogated antigen presenting cells: a preliminary approach for anti-HBV immunotherapy. Viorol. J. 7, 370. (2010).

17. Chen, C. et al. Production and characterization of agonist monoclonal antibodies against chicken CD40. Develop. Comp. Immunol. 34, 1139-1143. (2010).

18. Chen, C. et al. Immunization of chicken with an agonistic monoclonal anti-chicken CD40 antibody-hapten cpmlex: Rapid and Robust IgG response induced by a single subcutaneous injection. J. Immunol Methods. 378, 116-120. (2012).

19. Chou, W. et al. Significant mucosal sIgA production after a single oral or parenteral administration using in vivo CD40 targeting in the chicken. Res. Vet. Sci. 108, 112-115. (2016).

20. Tuerk, C. & L. Gold. Systemic evolution of ligand by exponential enrichment: RNA ligands to bacteriophage T4 DNA polymerase. Science. 249, 505-510. (1990).

21. Ellington, A. D. & J. W. Szostak. In vitro selection of RNA molecules that bind specific ligands. Nature. 346, 818-822. (1990).

22. Irvine, D. et al. SELEXION. Systemic evolution of ligands by exponential enrichment with integrated optimization by non-linear analysis. J. Mol. Biol. 222(3), 739-761. (1991).

23. Hermann, T. & D. J. Petel. Adaptive recognition by nucleic acid aptamers. Science. 287(5454), 820-825. (2000).

24. Jeddi, I. & L. Saiz. Three-dimensional modeling of single stranded DNA hairpins for aptamer-based biosensors. Scientific Reports. 1-13. (2017).

25. Baker, M. Blame it on the antibodies. Nature. 521, 274-276. (2015).

26. Bradbury, A. & A. Pluckthun. Reproducibility: standardize antibodies used in research. 518(7537), 27-29. (2015).

27. Mohsen, M. G. & E. Kool. The discovery of rolling circle amplification and rolling circle transcription. Acc. Chem. Res. 49(11), 2540-2550. (2016).

28. Ali, M. et al. Rolling circle amplification: a versatile tool for chemical biology, materials science and medicine. Chem. Soc. Rev. 43, 3324-3341. (2014).

29. Lv, L. et al. Aptamer and rolling circle amplification-involved sandwich assay for platelet-derived growth factor-BB with absorbance analysis. Anal. Methods. 7, 1855-1859. (2015).

30. Crippen, T. L. et al. Differential nitric oxide production by chicken immune cells. Develp. Compar. Immunol. 27, 603-610. (2003).

31. Berens, C. et al. A tetracycline-binding RNA aptamer. Bioorg. Med. Chem. 9, 2549-2556. (2001).

32. Sanger, F. et al. DNA sequencing with chain-terminating inhibitors. Proc. Natl. Acad. Sci. USA. 74(12), 5463-5467. (1977).

33. Armstrong, R. E. & G. F. Strouse. Rationally manipulating aptamer binding affinities in stem-loop molecular beacon. Bioconj. Chem. 25, 1769-1776. (2014).

34. Hussein, I. & M. A. Qureshi. Nitric oxide synthase activity and mRNA expression in chicken macrophage. Poult. Sci. 76, 1524-1530. (1997).

35. Brightbill, H. D. & R. L. Modlin. Toll-like receptors: molecular mechanisms of the mammalian immune response. Immunology. 101, 1-10. (2000).

36. Bonk, T. & A. Humney. MALDI-TOF-MS analysis of protein and DNA. The Neuroscientist. 7, 6-12. (2001).

37. An, H. J. et al. Crystallographic and mutational analysis of the CD40-CD154 complex and its implication for receptor activation. J. Biol. Chem. 286(13), 11226-11235. (2011).

38. Merluzzi, S. et al. CD40 stimulation induces Pax5/BSAP and EBF activation through a APE/Ref-1-dependent Redox mechanism. J. Biol. Chem. 279(3), 1777-1786. (2004)

39. Amitage, R. J. & M. R. Alderson. B-cell stimulation. Curr. Opin. Immunol. 7, 243-247. (1995).

40. Grassme, H. et al. Clustering of CD40 ligand is required to form functional contact with CD40. J. Biol Chem. 277(33), 30289-30299. (2002).

41. Bjorck, O. et al. Antibodies to distinct epitopes on the CD40 molecule co-operate in stimulation and can be used for the detection of soluble CD40. Immunol. 83, 430-437. (1994).

42. Maccam, M. & G. A. Bishop. Membrane-bound CD154, but not CD40-specific antibody, mediates NF-κB-independent IL-6 production in B cell. Eur. J. Immunol. 29, 3855-3866. (1999).

43. Dollins, C. M. et al. Aptamers in immunotherapy. Hum. Gene Ther. 19(5), 443-450. (2008).

44. Pastor, F. et al. CD28 aptamers as powerful immune response modulators. Molecular Therapy-Nucleic Acids. 2, (2013). e98; doi:10.1038/mtna.2013.26.

45. McNamara, J. O. et al. Multivalent 4-1BB binding aptamers costimulate CD8+ T cells and inhibit tumor growth in mice. J. Clin. Invest. 118(1), 376-386. (2007).

46. Wang, R. et al. Selection and characterization of DNA aptamers for use in detection of avian influenza virus H5N1. J. Virol. Meth. 189, 362-369. (2013).

47. Sypabekova, M. et al. Selection, characterization, and application of DNA aptamers for detection of *Mycoplasma* tuberculosis secreted protein MPT64. Tuberculosis. 104, 70-78. (2017).

48. Schutz, T. et al. Probing the SELEX process with next-generation sequencing. PLoS One. 6(12), e29604. doi:10.1371/journal.pone.0029604. (2011).

49. Thiel, W. H. & P. H. Giangrande. Analyzing HT-SELEX data with the Galaxy project tools—a web based bioinformatics platform for biomedical research. Methods. 15(97), 3-10. (2016). doi:10.1016/j.ymeth.2015.10.008.

50. Thiel, W. H. Galaxy workflows for web-based bioinformatics analysis of aptamers high-throughput sequencing data. Mol. Ther. Nuc. Aci. (2016). http://doi:10.1038/mtna.2016.54

51. Randrianjatovo-Gbalou, I. et al. Enzymatic synthesis of random sequences of RNA and RNA analogues by DNA polymerase theta mutants for the generation of aptamer libraries. Nuc. A. Res. 46(12), 6271-6284. (2018).

52. Kannan, L. et al. Identification and characterization of thymosin (30-4 in chicken macrophages using whole cell MALDI-TOF. Ann. N.Y. Acad. Sci. 1112, 425-434. (2007). http://doi:10.1196/annals.1415.028.

53. Kannan, L. et al., Evaluation of beta defensin 2 production by chicken heterophils using direct MALDI mass spectrometry. Mol. Immunol. 46(15), 3151-3156. (2009).

54. Vuong, C. N. et al., Crude Inactivated Influenza A Virus Adjuvated with a Bispecific Antibody Complex Targeting Chicken CD40 and AIV M2e Confers Protection Against Lethal HPAI Challenge in Chickens. Monoclon Antib Immunodiagn Immunother. 37(6):245-251. (2018).

55. Sides, C. R. et al., Probing the 3-D Structure, Dynamics, and Stability of Bacterial Collagenase Collagen Binding Domain (apo- versus holo-) by Limited Proteolysis MALDI-TOF MS. J. Am. Soc. Mass. Spectrom. 23:505-519. (2012).

We claim:

1. An immunostimulatory nucleic acid comprising a protein-binding sequence having at least 95% identity to any one of SEQ ID NOs: 1-8, wherein the immunostimulatory nucleic acid binds to CD40.

2. An immunostimulatory nucleic acid comprising a plurality of protein-binding units; wherein each of the protein-binding units comprise a first protein-binding sequence, a second protein-binding sequence, and a spacer sequence therebetween; wherein the second protein-binding sequence is a different sequence than the first protein-binding sequence; wherein (a) the first protein-binding sequence has at least 95% identity to any one of SEQ ID NOs: 1-8, (b) the second protein-binding sequence has at least 95% identity to any one of SEQ ID NOs: 1-8, or (c) both the first protein-binding sequence and the second protein-binding sequence have at least 95% identity to any one of SEQ ID NOs: 1-8; and wherein the immunostimulatory nucleic acid binds to CD40.

3. The immunostimulatory nucleic acid of claim 2, wherein the first and the second protein binding sequence are selected from SEQ ID NO: 3 and SEQ ID NO: 4.

4. The immunostimulatory nucleic acid of claim 2, wherein the immunostimulatory nucleic acid induces a CD40 signaling response when it is bound to CD40.

5. The immunostimulatory nucleic acid of claim 2, further comprising a binding tag.

6. A method of binding CD40, the method comprising contacting CD40 with the immunostimulatory nucleic acid of claim 1.

7. A template for producing a plurality of protein-binding units comprising in order from 5' to 3': i) a 3' end of a primer-binding sequence, ii) a reverse complement of a second protein-binding sequence, iii) a reverse complement of a spacer sequence, iv) a reverse complement of a first protein-binding sequence, and v) a 5' end of a primer-binding sequence, wherein the 5' end of the primer-binding sequence and the 3' end of the primer-binding sequence form a primer-binding site when the template is circularized.

8. The template of claim 7, wherein the first protein-binding sequence comprises a sequence having at least 95% identity to any one of SEQ ID NOs: 1-8, wherein the second protein-binding sequence comprises the sequence having at least 95% identity to any one of SEQ ID NOs: 1-8, or wherein both the first protein-binding sequence and the second protein-binding sequence comprise the sequence having at least 8095% identity to any one of SEQ ID NOs: 1-8, and wherein the plurality of protein-binding sequences bind to CD40.

9. The template of claim 7, wherein both the first protein-binding sequence and the second protein-binding sequence have an affinity for an immune response signaling protein.

10. The template of claim 9, wherein the immune response signaling protein is CD40.

11. A method of producing an immunostimulatory nucleic acid comprising (a) providing the template of claim 7, (b) circularizing the template, and (c) amplifying the circularized template to produce the immunostimulatory nucleic acid.

12. The method of claim 11, further comprising partially or completely hybridizing a complementary sequence to the spacer sequence of the immunostimulatory nucleic acid.

13. The method of claim 11, wherein step (a) comprises (i) identifying two or more protein-binding sequences with an affinity for an immune response signaling protein and (ii) selecting the complement of the first protein-binding sequence and the complement of the second protein-binding sequence from the identified sequences.

14. A method of producing an immunostimulatory complex comprising: (a) amplifying the template of claim 7 to produce an immunostimulatory nucleic acid, (b) tagging the immunostimulatory nucleic acid with a binding tag, and (c) linking the immunostimulatory nucleic acid to an antigen.

15. An immunostimulatory complex comprising an adjuvant and an antigen, wherein the adjuvant is the immunostimulatory nucleic acid of claim 1, and wherein the adjuvant and the antigen are linked.

16. The immunostimulatory complex of claim 15, wherein the antigen is a bacterial antigen, viral antigen, or fungal antigen.

17. The immunostimulatory complex of claim 15, wherein the antigen is a peptide.

18. A method for enhancing an immune response in a subject comprising administering an effective amount of the immunostimulatory complex of claim 15 to the subject.

* * * * *